United States Patent
Zhang et al.

(10) Patent No.: US 9,809,822 B2
(45) Date of Patent: Nov. 7, 2017

(54) TRIPTOLIDE DERIVATIVES AND PREPARATION METHOD AND USE THEREOF

(71) Applicant: Hong Kong Baptist University, Kowloon (HK)

(72) Inventors: Ge Zhang, Kowloon (HK); Aiping Lu, Kowloon (HK); Cheng Wang, Kowloon (HK); Cheng Lu, Kowloon (HK); Jun Lu, Kowloon (HK); Biao Liu, Kowloon (HK)

(73) Assignee: HONG KONG BAPTIST UNIVERSITY, KOWLOON TONG, KOWLOON (HK)

( * ) Notice: Subject to any disclaimer, the term of this patent is extended or adjusted under 35 U.S.C. 154(b) by 0 days.

(21) Appl. No.: 15/100,092

(22) PCT Filed: Dec. 11, 2013

(86) PCT No.: PCT/CN2013/001551
§ 371 (c)(1),
(2) Date: May 27, 2016

(87) PCT Pub. No.: WO2015/085447
PCT Pub. Date: Jun. 18, 2015

(65) Prior Publication Data
US 2016/0362691 A1 Dec. 15, 2016

(51) Int. Cl.
*C12N 15/115* (2010.01)
*A61K 47/48* (2006.01)
*A61K 31/7088* (2006.01)
*A61K 31/585* (2006.01)
*C07J 73/00* (2006.01)

(52) U.S. Cl.
CPC .......... *C12N 15/115* (2013.01); *A61K 31/585* (2013.01); *A61K 31/7088* (2013.01); *A61K 47/48092* (2013.01); *C07J 73/003* (2013.01); *C12N 2310/16* (2013.01); *C12N 2310/351* (2013.01); *C12N 2320/30* (2013.01)

(58) Field of Classification Search
CPC .............. C12N 15/115; C12N 2320/30; C12N 2310/16; C12N 2310/351; A61K 31/585; A61K 47/48092; A61K 31/7088; C07J 73/003
See application file for complete search history.

(56) References Cited

FOREIGN PATENT DOCUMENTS

| CN | 102716494 A | 10/2012 |
|---|---|---|
| CN | 102786576 A | 11/2012 |

OTHER PUBLICATIONS

Guo, J., "Aptamer-functionalized PEG—PLGA nanoparticles for enhanced anti-glioma drug delivery." Biomaterials 32.31 (2011): 8010-8020.*
English Translation of International Search Report (ISR), International Application No. PCT/CN2013/001551, mailed Sep. 11, 2014, 3 pages.
English Abstract of CN 102786576 A, 2 pages.
English Abstract of CN 102716494 A, 2 pages.

* cited by examiner

*Primary Examiner* — Matt Mauro
(74) *Attorney, Agent, or Firm* — Idea Intellectual Limited; Margaret A. Burke; Sam T. Yip

(57) ABSTRACT

Tripyolide-nucleic acid aptamer derivatives, a preparation method and use thereof are shown. The structure of the triptolide-nucleic acid aptamer derivatives is as shown by formula I, wherein the definitions of $R_1$-$R_7$, G, A, B, M, Z and X are described. The present invention uses a nucleic acid aptamer and triptolide or modified compounds thereof as the starting materials, and introduces a linking group A at the C-14 hydroxyl group, epoxy groups and five-membered ring lactones in triptolide, then connects it to a nucleic acid aptamer B, and obtains the triptolide-nucleic acid aptamer derivatives. The triptolide-nucleic acid aptamer derivatives of the present invention have the characteristics of good targeting, a high anti-cancer activity, low toxicity and side effects, good water solubility and high bioavailability, and the preparation method of the present invention is scientific and reasonable and has a controllable quality and good repeatability, and is thereby suitable for production.

19 Claims, 15 Drawing Sheets

<Chromatogram>

TRIPTOLIDE DERIVATIVES AND PREPARATION METHOD AND USE THEREOF

TECHNICAL FIELD

The present invention relates to the pharmaceutical field, and more particularly triptolide derivatives, a method for preparing the same and a use thereof.

BACKGROUND

Thunder god vine, a woody vine of Celastraceae Tripterygium, is distributed at the south of Yangtze River or southwest region. It is cold in nature, bitter and toxic. Triptolide (TP) is an epoxidized diterpene lactone compound separated from a traditional Chinese medicine *Tripterygium wilfordii* Hook f, and is one of the main active ingredients in *T. wilfordii* Hook f Triptolide is in the form of white crystals. It is not soluble in water but soluble in various organic solvents.

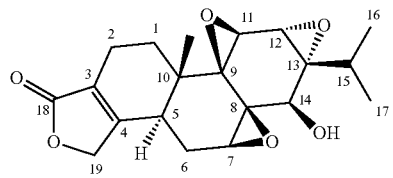

Triptolide is a diterpenoid compound with an abietane skeleton. It has three epoxy structures and an α,β-unsaturated five-membered lactone ring. Triptolide has various activities such as anti-inflammatory, immunosuppressive, anti-fertility and anti-cancer activities. It can be used to treat rheumatoid arthritis, systemic lupus erythematosus, ankylosing spondylitis and cancer etc. Studies show that triptolide is a broad-spectrum cancer suppressor and can induce apoptosis of a variety of cancers cell in in vitro, including ovarian cancer, breast cancer, colon cancer, oral cancer, stomach cancer and so forth. It can also inhibit tumor growth and metastasis of cancer cells in vivo, including hematological cancers, malignancies and solid cancers. The anti-cancer activity of triptolide is better than that of the traditional anti-cancer drugs such as cisplatin, doxorubicin and paclitaxel. Triptolide can effectively inhibit the growth of the cancer cells at an extremely low concentration (2-10 ng/ml). Further, triptolide can overcome the drug resistance of cancer cells and at the same time increases the sensitivity of cancer cells to other anti-cancer drugs. Triptolide further has synergistic effect when combining with chemotherapeutic drugs and ionizing radiation.

Currently, many studies have focused on investigating the anti-cancer mechanism of triptolide. Triptolide can inhibit the expression of heat shock protein 70 (HSP 70). As an inhibitor of heat shock protein response, triptolide can effectively inhibit the expression of HSP 70 genes and induce cell apoptosis. Triptolide can inhibit nuclear factor kappaB (NF-κB, NF-κB does not only promote cancer cell proliferation but also activate oncogene and anti-apoptotic genes) which lowers the sensitivity of cancer cells towards apoptosis. In one hand, triptolide inhibits the combination of NF-κB and a specific DNA sequence at the target gene and further interferes the transcription activity of NF-κB; on the other hand, triptolide can prevent nuclear kinase from performing phosphorylation on NF-κB trans-activating region or interfere the nuclear accumulation of auxiliary protein of NF-κB, i.e. cAMP response element binding protein, as well as interfere the interaction between P65 and RNA polymerase and further inhibits the transcription activity of NF-κB to promote apoptosis. In addition to the above mechanism, triptolide can further exhibit its anti-cancer effect through various ways such as inhibiting ubiquitin-proteasome, affecting the activity of RNA polymerase, affecting the expression of p53 gene, activating caspase etc. Thus, triptolide is a potent candidate of anticancer drug.

Although triptolide has significant anti-tumor activity, the low bioavailability due to its poor water solubility and the high toxicity limit its clinical application.

Researchers of the technical field have modified the structure of triptolide, and some of the studies show that:

1. When $C_{14}$ hydroxyl is replaced by an electron withdrawing group, the cytotoxicity of the derivatives increases, as shown in FIG. 1-1; the cytotoxicity of M-1 and M-2 are greater than TP, however, the activity of M-1 is greater than M-2, i.e. the steric effect at C-14 is significant.

FIG. 1-1

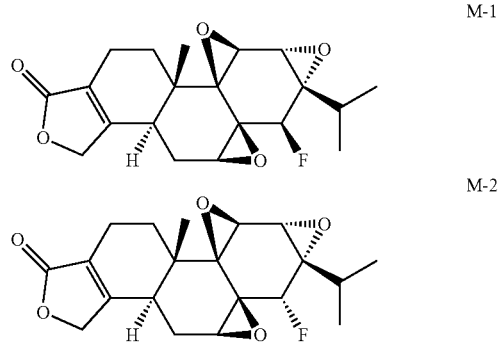

2. When $C_{14}$ hydroxyl forms a structure of three-membered epoxy, the bioactivity increases and the toxicity decreases because it cannot form intra-molecular hydrogen bond. However, when it forms a five-membered ring, the activity decreases. This may be because of the steric effect which causes the combination of the receptor and the drug, as shown in FIG. 1-2.

FIG. 1-2

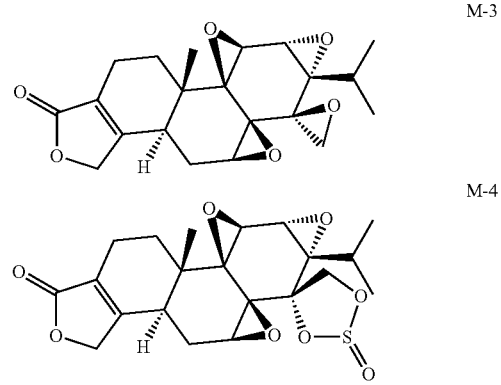

3. When epoxy at $C_{12,13}$ position opens the ring structure, the formed structure has a certain stability in vivo and that the immunosuppressive activity of such a derivative is diminished while the anti-inflammatory activity remains unchanged. Epoxy at $C_{7,8}$ is less susceptible to nucleophilic attack, however, the bioactivity and the cytotoxicity of the derivative formed after the ring-opening decrease. There are few reports regarding ring-opening of epoxy at $C_{12,13}$ position, nevertheless, the bioactivity of the derivative formed after the ring-opening does not vary significantly, as shown in FIG. 1-3:

FIG. 1-3

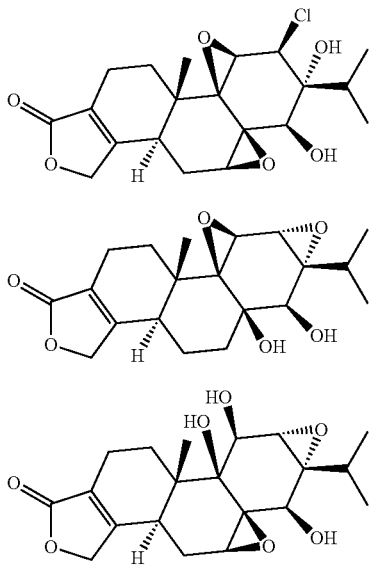

4. α,β-unsaturated five-membered lactone ring is one of the essential groups for exhibiting bioactivity. Modifications to the lactone ring significantly reduce the activities of the compound, such as anti-cancer activity and immunosuppressive activity. Although the modification to $C_5$ position results in cytotoxicity and reduces the immunosuppressive activity, the derivative still has good in vivo and in vitro activities with significantly reduced toxicity. Accordingly, the safety of the treatment is greatly improved, as shown in FIG. 1-4.

FIG. 1-4

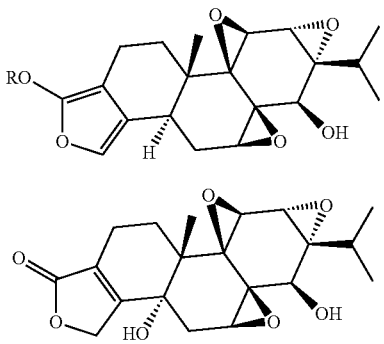

To conclude, current modifications to triptolide mainly include $C_{14}$ hydroxyl, α,β-unsaturated five-membered lactone ring, $C_{12,13}$ epoxy, $C_{7,8}$ epoxy and $C_{9,11}$ epoxy. The β-OH at $C_{14}$ position is the only nucleophilic group in the molecule, which is associated with the water solubility and cytotoxicity of triptolide. This β-OH can form intra-molecular hydrogen bond with β-epoxy at $C_{9,11}$ position and is the critical group of anti-cancer effect. When β-OH at $C_{14}$ is replaced by an electron withdrawing group, the cytotoxicity of the derivatives increases; when β-OH at $C_{14}$ forms a three-membered epoxy, it cannot form intra-molecular hydrogen bond, and thus the bioactivity increases while the toxicity decreases. The epoxy structure at $C_{12,13}$ position has a certain stability in vivo after the ring-opening. The derivatives formed after the ring-opening still possess the anti-inflammatory activity but not the immunosuppressive activity. When the epoxy structure at $C_{7,8}$ opens, the bioactivity and cytotoxicity decrease. α,β-unsaturated five-membered lactone ring is an essential group, and the modifications to the lactone ring can reduce the bioactivities of the derivative, such as anti-cancer activity and immunosuppressive activity. However, the modified derivatives still have good effects with significantly reduced toxicity. Accordingly, the safety of the treatment is greatly improved.

The modification sites on triptolide mainly include hydroxyl at $C_{14}$, epoxy at $C_{12,13}$, α,β-unsaturated five-membered lactone ring, epoxy at $C_{7,8}$ and epoxy at $C_{9,11}$. However, among the modified triptolides, only those compounds having modification on the hydroxyl at $C_{14}$, epoxy at $C_{12,13}$, and carbonyl at $C_{18}$ can be converted to triptolide in vivo and then exert its therapeutic effect.

Aptamer is a kind of oligonucleotides with therapeutic effects. It can bind with target proteins with high affinity and selectivity, and its function is similar to a monoclonal antibody. There are many advantages of aptamers in practice: high affinity and high selectivity; small molecular weight and therefore aptamers can enter the cell through cell membrane, and can be readily directed to the in vivo target site with a substantial amount; good stability and the half-life is long in vivo; they are not sensitive to the ambient temperature and thus it is easy to store; it is easy to synthesize and modify, and therefore improve the applications of aptamers in clinical diagnosis and treatments. Aptamers can be directly used as drugs for treating diseases. When part of the aptamers binds to the corresponding target sequence, the function of the respective protein is inhibited as the binding site represents the functional region of the protein. Aptamers can also be used as drug carriers. The connection between the drug and the aptamers render the drug to have cell selectivity so as to avoid toxic side effects to normal tissues and cells.

AS1411 and Sgc8c are well-known aptamers. AS1411 is a guanine rich oligonucleotide (GROs) and can form a stable G-quadruplex structure. The nucleotide sequence of AS1411 is consisting of SEQ ID NO: 1 and can effectively act against intracellular nuclease degradation. AS1411 can specifically binds to nucleolin highly expressed on the surface of the cancer cell, and nucleolin on the cell membrane enhances great pinocytosis of the cancer cell to AS1411 and thus increase the uptake. A number of studies showed that AS1411 has broad-spectrum anti-cancer activity. The study on the anti-proliferative activity of AS1411 on a variety of human cell lines show that AS1411 is capable of inhibiting almost all kinds of cancer cells, $IC_{50}$ reaches micro molar level and such a concentration has weak impact to normal cells. The anti-cancer mechanism of AS1411 mainly involves the inhibition of the cellular DNA replication after entering the nuclear, so as to arrest the cell cycle in S-phase, thereby inhibiting cancer cell proliferation. Sgc8c is a single-stranded DNA aptamer specifically targeting T-cell acute lymphoblastic leukemia. Sgc8c was screened by systematic evolution of ligands by exponential enrichment (cell-SELEX) using intact cells as target enrichment index. Since Sgc8c has many advantages such as high stability in serum, high specificity and low immunogenicity, it is used as the target ligand for coupling with chemotherapeutic agents and achieves an excellent result in the treatment of T-cell acute lymphoblastic leukemia. The nucleotide sequence of Sgc8c is consisting of SEQ ID NO: 2.

However, there are no reports of improving the biological performances of triptolide and its structural derivatives by combining triptolide and its structural derivatives with aptamers.

SUMMARY

Considering triptolide and its structural derivatives in the existing technology, the present invention provides novel triptolide derivatives, a method of preparing the same and the use thereof.

Since the bioactivity of triptolide is primarily related to the functional groups (its structure is as shown below):

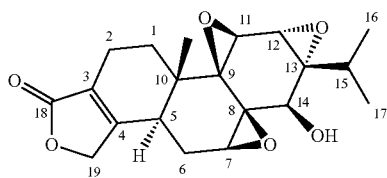 [SMILES: CC(C)[C@]12O[C@H]1[C@@H]1O[C@]13[C@]1(O[C@H]1C[C@H]1C4=C(CC[C@@]13C)C(=O)OC4)[C@@H]2O]

The modification sites for structural modifications of the triptolide mainly include hydroxyl at $C_{14}$, epoxy at $C_{12,13}$, five-membered lactone ring, epoxy at $C_{7,8}$ and epoxy at $C_{9,11}$. However, among the modified triptolide derivatives, only those compounds having a modification at the hydroxyl at $C_{14}$, epoxy at $C_{12,13}$, and carbonyl at $C_{18}$ can be again converted to triptolide in vivo.

Therefore, the present invention provides novel triptolide derivatives, which are compounds having the Formula (I), as shown below:

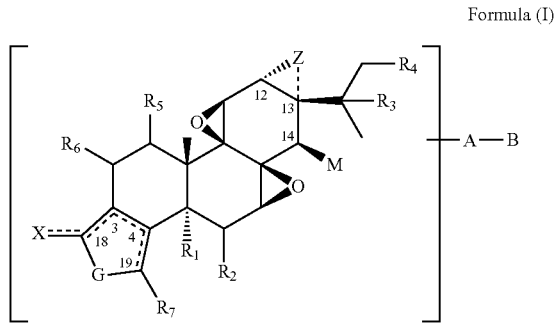

Formula (I)

$R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
A is —CO—, —CO—$(CH_2)_n$—CO—, —CH=CH—CO—, —CH=CH—$(CH_2)_n$—CO—, —CH(OH)—Ph-CO—, CH(OH)-Ph-$(CH_2)_n$—CO—, —$CH_2$-Ph-$(CH_2)_n$—CO—, —CO—NH—CO—, —CO—NH—$(CH_2)_n$—CO—, —$CH_2$—CH=CH—CO—, —$CH_2$—CH=CH—$(CH_2)_n$—CO—, —CO—$CH_2$—, —CO—O—$(CH_2)_n$—CO—, —$SO_2$-Ph-CO—, —$SO_2$-Ph-$(CH_2)_n$—CO—; wherein $1 \leq n \leq 14$; preferably $1 \leq n \leq 7$, for example, n is 1, 2, 3, 4, 5, 6 or 7.

In one embodiment of the present invention, optionally $(CH_2)_n$ further comprises a substituent selected from straight or branched alkyl, alkenyl, aralkyl, or alkyl aryalkyl, aryl, halogen, a group with a heteroatom, or heterocycle substituting one or more H in the $(CH_2)_n$, the alkyl comprises but not limited to methyl, ethyl, propyl, butyl, pentyl, hexyl or heptyl; the alkenyl comprises vinyl, 1-propenyl, allyl, isopropenyl, 1-butenyl, 2-butenyl, 3-butenyl, 1,3-butadienyl, or the E, Z isomers thereof; the examples of the aralkyl and the alkyl aralkyl comprise but not limited to benzyl, diphenylmethyl, tolyl methyl, triphenylmethyl, cinnamyl, phenethyl, styryl, phenylbutyl and neophenyl; the aryl comprises but not limited to phenyl, diphenyl, tolyl, methylbenzyl, 4,2,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl, and morpholino benzyl or phenyl; the halogen comprises but not limited to fluorine, chlorine, bromine and iodine; the group with the heteroatom comprises but not limited to methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle comprises but not limited to pyridine, quinolone, thiophene, furan, oxazole, tetrazole, thiazole, imidazole, pyrazole or indole;

B is an aptamer, and the aptamer is AS1411 or Sgc8c;
M is O or OH;

Z is O;
X is O;
wherein A is connected with M, Z or X.

As one embodiment of the present invention, A is selected from —CO—;
—CO—CH$_2$—CO—, —CO—CH$_2$—CH$_2$—CO—, —CO—CH$_2$—CH$_2$—CH$_2$—CO—,
—CO—CH$_2$—CH—C—CH$_2$—CH$_2$—CO—;
—CH=CH—CO—;
—CH(OH)-Ph-CO—, —CH(OH)-Ph-CH$_2$—CO—, —CH(OH)-Ph-CH$_2$—CH$_2$—CO—, —CH(OH)-Ph-CH$_2$—CH$_2$—CH$_2$—CO—,
—CH(OH)-Ph-CH$_2$—CH$_2$—CH$_2$—CH$_2$—CO—;
—CH$_2$-Ph-CH$_2$—CO—, —CH$_2$-Ph-CH$_2$—CH$_2$—CO—, —CH$_2$-Ph-CH$_2$—CH$_2$—CH$_2$—CO—, —CH$_2$-Ph-CH$_2$—CH$_2$—CH$_2$—CH$_2$—CO—;
—CO—NH—CO—, —CO—NH—CH$_2$—CO—, —CO—NH—CH$_2$—CH$_2$—CO—,
—CO—NH—CH$_2$—CH$_2$—CH$_2$—CO—, —CO—NH—CH$_2$—CH$_2$—CH$_2$—CH$_2$—CO—;
—CH$_2$—CH=CH—CO—, —CH$_2$—CH=CH—CH$_2$—CO—,
—CH$_2$—CH=CH—CH$_2$—CH$_2$—CO—, —CH$_2$—CH=CH—CH$_2$—CH$_2$—CH$_2$—CO—,
—CH$_2$—CH=CH—CH$_2$—C—CH$_2$—CH$_2$—CO;
—CO—CH$_2$—;
—CO—O—CO—, —CO—O—CH$_2$—CO—, —CO—O—CH$_2$—CH$_2$—CO—,
—CO—O—CH$_2$—CH$_2$—CH$_2$—CO—, —CO—O—CH$_2$—CH$_2$—CH$_2$—CH$_2$—CO—;
—SO$_2$-Ph-CO—, —SO$_2$-Ph-CH$_2$—CO—, —SO$_2$-Ph-CH$_2$—CH$_2$—CO—,
—SO$_2$-Ph-CH$_2$—CH$_2$—CH$_2$—CO—, or —SO$_2$-Ph-CH$_2$—CH$_2$—CH$_2$—CH$_2$—CO—;

In one embodiment of the present invention, the triptolide derivative has a structure of Formula (II), as shown below:

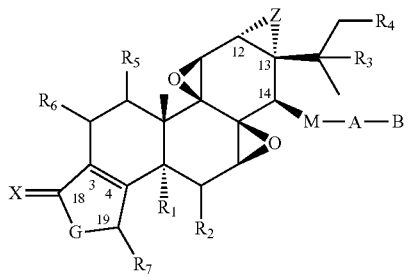

Formula (II)

wherein, $R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
M is O;
Z is O;
X is O, and forms a carbonyl at $C_{18}$;
A is selected from —CO—, —CO—(CH$_2$)$_n$—CO—, —CH=CH—CO—, —CH=CH—(CH$_2$)$_n$—CO—, —CH(OH)-Ph-CO—, CH(OH)-Ph-(CH$_2$)$_n$—CO—, —CH$_2$-Ph-(CH$_2$)$_n$—CO—, —CO—NH—CO—, —CO—NH—(CH$_2$)$_n$—CO—, —CH$_2$—CH=CH—CO—, —CH$_2$—CH=CH—(CH$_2$)$_n$—CO—, —CO—CH$_2$—, —CO—O—(CH$_2$)$_n$—CO—, —SO$_2$-Ph-CO— or —SO$_2$-Ph-(CH$_2$)$_n$—CO—; wherein 1≤n≤14; preferably 1≤n≤7, for example, n is 1, 2, 3, 4, 5, 6 or 7;

In one embodiment of the present invention, optionally (CH$_2$)$_n$ further comprises a substituent selected from straight or a branched alkyl, alkenyl, aralkyl, or alkyl aryalkyl, aryl, halogen, a group with a heteroatom, or heterocycle substituting one or more H in the (CH$_2$)$_n$, the alkyl comprises but not limited to methyl, ethyl, propyl, butyl, pentyl, hexyl or heptyl; the alkenyl comprises vinyl, 1-propenyl, allyl, isopropenyl, 1-butenyl, 2-butenyl, 3-butenyl, 1,3-butadienyl, or the E, Z isomers thereof; the examples of the aralkyl and the alkyl aralkyl comprise but not limited to benzyl, diphenylmethyl, tolyl methyl, triphenylmethyl, cinnamyl, phenethyl, styryl, phenylbutyl and neophenyl; the aryl comprises but not limited to phenyl, diphenyl, tolyl, methylbenzyl, 4,2,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl, and morpholino benzyl or phenyl and so forth; the halogen comprises but not limited to fluorine, chlorine, bromine and iodine; the group with the heteroatom comprises but not limited to methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle comprises but not limited to pyridine, quinolone, thiophene, furan, oxazole, tetrazole, thiazole, imidazole, pyrazole or indole;

B is an aptamer, and the aptamer is AS1411 or Sgc8c.
M is O or OH;
Z is O;
X is O;
wherein A is connected with M, Z or X.

In one embodiment of the present invention, A is selected from —CO—;

—CO—CH$_2$—CO—, —CO—CH$_2$—CH$_2$—CO—, —CO—CH$_2$—CH$_2$—CH$_2$—CO—, —CO—CH$_2$—CH$_2$—CH$_2$—CH$_2$—CO—;
—CH═CH—CO—, —CH═CH—CH$_2$—CO—, —CH═CH—CH$_2$—CH$_2$—CO—, —CH═CH—CH$_2$—CH$_2$—CH$_2$—CO—, —CH═CH—CH$_2$—C═CHCH$_2$—CH$_2$—CO—;
—CH(OH)-Ph-CO—, —CH(OH)-Ph-CH$_2$—CO—, —CH(OH)-Ph-CH$_2$—CH$_2$—CO—, —CH(OH)-Ph-CH—CH$_2$—CH$_2$—CO—, —CH(OH)-Ph-CH$_2$—CH$_2$—CH$_2$—CH$_2$—CO—;
—CH$_2$-Ph-CH$_2$—CO—, —CH$_2$-Ph-CH$_2$—CH$_2$—CO—, —CH$_2$-Ph-CH$_2$—CH$_2$—CH$_2$—CO—, —CH$_2$-Ph-CH$_2$—CH$_2$—CH$_2$—CH$_2$—CO—;
—CO—NH—CO—, —CO—NH—CH$_2$—CO—, —CO—NH—CH$_2$—CH$_2$—CO—, —CO—NH—CH$_2$—CH$_2$—CH$_2$—CO—, —CO—NH—CH$_2$—CH$_2$—CH$_2$—CH$_2$—CO—;
—CH$_2$—CH═CH—CO—, —CH$_2$—CH═CH—CH$_2$—CO—, —CH$_2$—CH═CH—CH$_2$—CH$_2$—CO—, —CH$_2$—CH═CH—CH$_2$—CH$_2$—CH$_2$—CO—, —CH$_2$—CH═CH—CH$_2$—CH$_2$—CH$_2$—CH$_2$—CO;
—CO—CH$_2$—;
—CO—O—CO—, —CO—O—CH$_2$—CO—, —CO—O—CH$_2$—CH$_2$—CO—, —CO—O—CH$_2$—CH$_2$—CH$_2$—CO—, —CO—O—CH$_2$—CH$_2$—CH$_2$—CH$_2$—CO—;
—SO$_2$-Ph-CO—, —SO$_2$-Ph-CH$_2$—CO—, —SO$_2$-Ph-CH$_2$—CH$_2$—CO—, —SO$_2$-Ph-CH$_2$—CH$_2$—CH$_2$—CO—, or —SO$_2$-Ph-CH$_2$—CH$_2$—CH$_2$—CH$_2$—CO—.

In one embodiment of the present invention, B is an aptamer, and the aptamer is AS1411 or Sgc8c.

In one embodiment of the present invention, the triptolide derivative of Formula (II) is a compound having the following structure:

| | Substituent | | | | | | | | | | | | |
|---|---|---|---|---|---|---|---|---|---|---|---|---|---|
| No. | $R_1$ | $R_2$ | $R_3$ | $R_4$ | $R_5$ | $R_6$ | $R_7$ | G | M | Z | X | A | B |
| (1) | H | H | H | H | H | H | H | O | O | O | O | —CO—CH$_2$—CH$_2$—CO— | AS1411 |
| (2) | H | H | H | H | H | H | H | O | O | O | O | —CO— | AS1411 |
| (3) | H | H | H | H | H | H | H | O | O | O | O | —CH═CH—CO— | AS1411 |
| (4) | H | H | H | H | H | H | H | O | O | O | O | —CH(OCH$_3$)—Ph—CO— | AS1411 |
| (5) | H | H | H | H | H | H | H | O | O | O | O | —CH$_2$—Ph—CH$_2$—CO— | AS1411 |
| (6) | H | H | H | H | H | H | H | O | O | O | O | —CO—NH—CH$_2$—CO— | AS1411 |
| (7) | H | H | H | H | H | H | H | O | O | O | O | —CH$_2$—CH═CH—CO— | AS1411 |
| (8) | H | H | H | H | H | H | H | O | O | O | O | —CO—CH$_2$— | AS1411 |
| (9) | H | H | H | H | H | H | H | O | O | O | O | —CO—O—(CH$_2$)$_2$—CO— | AS1411 |
| (10) | H | H | H | H | H | H | H | O | O | O | O | —CO—CH$_2$—CO— | AS1411 |
| (11) | H | H | H | H | H | H | H | O | O | O | O | —CH═CH—CH$_2$—CO— | AS1411 |
| (12) | H | H | H | H | H | H | H | O | O | O | O | —CH$_2$—CH═CH—CH$_2$—CO— | AS1411 |
| (13) | H | H | H | H | H | H | H | O | O | O | O | —CO—O—CO— | AS1411 |
| (14) | H | H | H | H | H | H | H | O | O | O | O | —SO$_2$—Ph—CH$_2$—CO— | AS1411 |
| (15) | H | H | H | H | H | H | H | O | O | O | O | —CH═CH—CH$_2$—CH$_2$—CO— | AS1411 |
| (16) | H | H | H | H | H | H | H | O | O | O | O | —CH$_2$—Ph—CH$_2$—CH$_2$—CO— | AS1411 |
| (17) | H | H | H | H | H | H | H | O | O | O | O | —CO—NH—CH2—CH$_2$—CO— | AS1411 |
| (18) | H | H | H | H | H | H | H | O | O | O | O | —CH$_2$—CH═CH—CH$_2$—CH$_2$—CO | AS1411 |
| (19) | H | H | H | H | H | H | H | O | O | O | O | —CO—O—CH$_2$—CH$_2$—CO | AS1411 |
| (20) | H | H | H | H | H | H | H | O | O | O | O | —CO—CH$_2$—CO— | Sgc8c |
| (21) | H | H | H | H | H | H | H | O | O | O | O | —CH═CH—CH$_2$—CO— | Sgc8c |
| (22) | H | H | H | H | H | H | H | O | O | O | O | —CH═CH—CO— | Sgc8c |
| (23) | H | H | H | H | H | H | H | O | O | O | O | —CH$_2$—Ph—CH$_2$—CO— | Sgc8c |
| (24) | H | H | H | H | H | H | H | O | O | O | O | —CO—NH—CH$_2$—CO— | Sgc8c |
| (25) | H | H | H | H | H | H | H | O | O | O | O | —CH$_2$—CH═CH—CH$_2$—CO— | Sgc8c |
| (26) | H | H | H | H | H | H | H | O | O | O | O | —CO—O—CH$_2$—CO— | Sgc8c |
| (27) | H | H | H | H | H | H | H | O | O | O | O | —SO$_2$—Ph—CH$_2$—CO— | Sgc8c |
| (28) | H | H | H | H | H | H | H | O | O | O | O | —CO—CH$_2$—CH$_2$—CO— | Sgc8c |
| (29) | H | H | H | H | H | H | H | O | O | O | O | —CH═CH—CH$_2$—CH$_2$—CO— | Sgc8c |
| (30) | H | H | H | H | H | H | H | O | O | O | O | CH$_2$—Ph—CH$_2$—CH$_2$—CO— | Sgc8c |
| (31) | H | H | H | H | H | H | H | O | O | O | O | —CO—NH—CH$_2$—CH$_2$—CO | Sgc8c |
| (32) | H | H | H | H | H | H | H | O | O | O | O | —CH$_2$—CH═CH—CH$_2$—CH$_2$—CO— | Sgc8c |
| (33) | H | H | H | H | H | H | H | O | O | O | O | —CO—O—CH$_2$—CH$_2$—CO— | Sgc8c |
| (34) | OH | H | H | H | H | H | H | O | O | O | O | —CH═CH—CO— | AS1411 |
| (35) | H | OH | H | H | H | H | H | O | O | O | O | —CH═CH—CO— | AS1411 |
| (36) | H | H | OH | H | H | H | H | O | O | O | O | —CH═CH—CO— | AS1411 |
| (37) | H | H | H | OH | H | H | H | O | O | O | O | —CH═CH—CO— | AS1411 |
| (38) | H | H | H | H | OH | H | H | O | O | O | O | —CH═CH—CO— | AS1411 |
| (39) | H | H | H | H | H | OH | H | O | O | O | O | —CH═CH—CO— | AS1411 |
| (40) | H | H | H | H | H | H | OH | O | O | O | O | —CH═CH—CO— | AS1411 |
| (41) | H | H | H | H | H | H | H | NH | O | O | O | —CH═CH—CO— | AS1411 |
| (42) | OH | H | H | H | H | H | H | O | O | O | O | —CH═CH—CO— | Sgc8c |
| (43) | H | OH | H | H | H | H | H | O | O | O | O | —CH═CH—CO— | Sgc8c |
| (44) | H | H | OH | H | H | H | H | O | O | O | O | —CH═CH—CO— | Sgc8c |
| (45) | H | H | H | OH | H | H | H | O | O | O | O | —CH═CH—CO— | Sgc8c |
| (46) | H | H | H | H | OH | H | H | O | O | O | O | —CH═CH—CO— | Sgc8c |
| (47) | H | H | H | H | H | OH | H | O | O | O | O | —CH═CH—CO— | Sgc8c |
| (48) | H | H | H | H | H | H | OH | O | O | O | O | —CH═CH—CO— | Sgc8c |
| (49) | H | H | H | H | H | H | H | NH | O | O | O | —CH═CH—CO— | Sgc8c |

In one embodiment of the present invention, the triptolide derivative has a structure of Formula (III), as shown below:

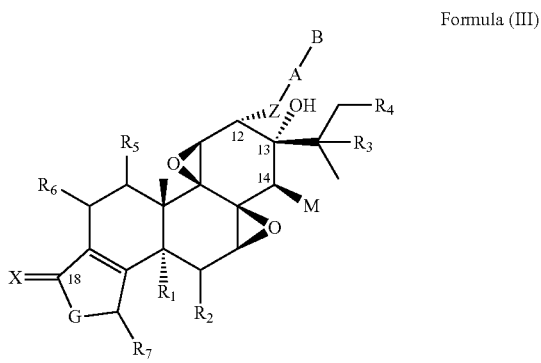

Formula (III)

wherein, $R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
M is OH;
Z is O;
X is O;
A is —$SO_2$-Ph-CO— or —$SO_2$-Ph-$(CH_2)_n$—CO—; wherein 1≤n≤14; preferably 1≤n≤7, for example, n is 1, 2, 3, 4, 5, 6 or 7;

In one embodiment of the present invention, optionally $(CH_2)_n$ further comprises a substituent selected from straight or branched alkyl, alkenyl, aralkyl, or alkyl aryalkyl, aryl, halogen, a group with a heteroatom, heterocycle substituting one or more H in the $(CH_2)$, the alkyl comprises but not limited to methyl, ethyl, propyl, butyl, pentyl, hexyl or heptyl; the alkenyl comprises vinyl, 1-propenyl, allyl, isopropenyl, 1-butenyl, 2-butenyl, 3-butenyl, 1,3-butadienyl, or the E, Z isomers thereof; the examples of the aralkyl and the alkyl aralkyl comprise but not limited to benzyl, diphenylmethyl, tolyl methyl, triphenylmethyl, cinnamyl, phenethyl, styryl, phenylbutyl and neophenyl; the aryl comprises but not limited to phenyl, diphenyl, tolyl, methylbenzyl, 2,4,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl, and morpholino benzyl or phenyl and so forth; the halogen comprises but not limited to fluorine, chlorine, bromine and iodine; the group with the heteroatom comprises but not limited to methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle comprises but not limited to pyridine, quinolone, thiophene, furan, oxazole, tetrazole, thiazole, imidazole, pyrazole or indole;

B is an aptamer, and the aptamer is AS1411 or Sgc8c.

In one embodiment of the present invention, A is selected from —$SO_2$-Ph-CO—, —$SO_2$-Ph-$CH_2$—CO—, —$SO_2$-Ph-$CH_2$—$CH_2$—CO—, —$SO_2$-Ph-$CH_2$—$CH_2$—$CH_2$—CO—, or —$SO_2$-Ph-$CH_2$—$CH_2$—$CH_2$—$CH_2$—CO—.

In one embodiment of the present invention, B is an aptamer, and the aptamer is AS1411 or Sgc8c.

In one embodiment of the present invention, the triptolide derivative of Formula (III) is a compound having the following structure:

| | | | | | | | Substituent | | | | | | |
|---|---|---|---|---|---|---|---|---|---|---|---|---|---|
| No. | $R_1$ | $R_2$ | $R_3$ | $R_4$ | $R_5$ | $R_6$ | $R_7$ | G | M | Z | X | A | B |
| (50) | H | H | H | H | H | H | H | O | OH | O | O | —$SO_2$—Ph—$CH_2$—CO— | AS1411 |
| (51) | H | H | H | H | H | H | H | O | OH | O | O | —$SO_2$—Ph—$CH_2$—$CH_2$—CO— | AS1411 |
| (52) | H | H | H | H | H | H | H | O | OH | O | O | —$SO_2$—Ph—$CH_2$—$CH_2$—$CH_2$—CO— | AS1411 |
| (53) | H | H | H | H | H | H | H | O | OH | O | O | —$SO_2$—Ph—$CH_2$—CO— | Sgc8c |
| (54) | H | H | H | H | H | H | H | O | OH | O | O | —$SO_2$—Ph—$CH_2$—$CH_2$—CO— | Sgc8c |
| (55) | H | H | H | H | H | H | H | O | OH | O | O | —$SO_2$—Ph—$CH_2$—$CH_2$—CO— | Sgc8c |

In one embodiment of the present invention, the triptolide derivative has the structure of Formula (IV), as shown below:

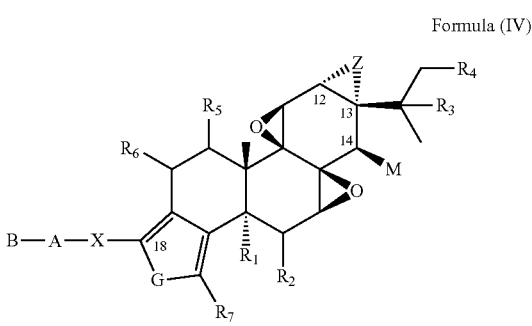

Formula (IV)

wherein, $R_1$=H or OH;
$R_2$=H or OH;
$R_3$=H or OH;

$R_4$=H or OH;
$R_5$=H or OH;
$R_6$=H or OH;
$R_7$=H or OH;
G is O or NH;
M is OH;
Z is O;
X is O;
A is —CO—, —CO—$(CH_2)_n$—CO—, —CH=CH—CO—, —CH=CH—$(CH_2)_n$—CO—,
—CH(OH)-Ph-CO—, —CH(OH)-Ph-$(CH_2)_n$—CO—, —$CH_2$-Ph-$(CH_2)_n$—CO—,
—CO—NH—CO—, —CO—NH—$(CH_2)_n$—CO—, —$CH_2$—CH=CH—CO—,
—$CH_2$—CH=CH—$(CH_2)_n$—CO—, —CO—$CH_2$—; —CO—O—$(CH_2)_n$—CO—, —$SO_2$-Ph-CO— or $SO_2$-Ph-$(CH_2)_n$—CO—; wherein 1≤n≤14; preferably 1≤n≤7, for example, n is 1, 2, 3, 4, 5, 6 or 7;

In one embodiment of the present invention, optionally $(CH_2)_n$ further comprises a substituent selected from straight or branched alkyl, alkenyl, aralkyl, or alkyl aryalkyl, aryl, halogen, heteroatom, heterocycle substituting one or more H in the $(CH_2)_n$, the alkyl comprises but not limited to methyl, ethyl, propyl, butyl, pentyl, hexyl or heptyl; the alkenyl comprises vinyl, 1-propenyl, allyl, isopropenyl, 1-butenyl, 2-butenyl, 3-butenyl, 1,3-butadienyl, or the E, Z isomers thereof; the aralkyl and the alkyl aralkyl comprise benzyl, diphenylmethyl, tolyl methyl, triphenylmethyl, cinnamyl, phenethyl, styryl, phenylbutyl and neophenyl; the examples of the aryl comprises but not limited to phenyl, diphenyl, tolyl, methylbenzyl, 2,4,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl and morpholino benzyl or phenyl; the halogen comprises but not limited fluorine, chlorine, bromine and iodine; the heteroatom comprises but not limited to methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle comprises but not limited to pyridine, quinolone, thiophene, furan, oxazole, tetrazole, thiazole, imidazole, pyrazole or indole.

B is an aptamer, and the aptamer is AS1411 or Sgc8c.
M is O or OH;
Z is O;
X is O;
wherein A is connected with M, Z or X.

In one embodiment of the present invention, A is preferably selected from —CO—;
—CO—$CH_2$—CO—, —CO—$CH_2$—$CH_2$—CO—, —CO—$CH_2$—$CH_2$—$CH_2$—CO—,
—CO—$CH_2$—$CH_2$—$CH_2$—$CH_2$—CO—;
—CH=CH—CO—, —CH=CH—$CH_2$—CO—, —CH=CH—$CH_2$—$CH_2$—CO—, —CH=CH—$CH_2$—$CH_2$—$CH_2$—CO—, —CH=CH—$CH_2$—$CH_2$—$CH_2$—$CH_2$—CO—;
—CH(OH)-Ph-CO—, —CH(OH)-Ph-$CH_2$—CO—, —CH(OH)-Ph-$CH_2$—$CH_2$—CO—, —CH(OH)-Ph-$CH_2$—$CH_2$—$CH_2$—CO—,
—CH(OH)-Ph-$CH_2$—$CH_2$—$CH_2$—$CH_2$—CO—;
—$CH_2$-Ph-$CH_2$—CO—, —$CH_2$-Ph-$CH_2$—$CH_2$—CO—, —$CH_2$-Ph-$CH_2$—$CH_2$—$CH_2$—CO—, —$CH_2$-Ph-$CH_2$—$CH_2$—$CH_2$—$CH_2$—CO—;
—CO—NH—CO—, —CO—NH—$CH_2$—CO—, —CO—NH—$CH_2$—$CH_2$—CO—, —CO—NH—$CH_2$—$CH_2$—$CH_2$—CO—, —CO—NH—$CH_2$—$CH_2$—$CH_2$—$CH_2$—CO—;
—$CH_2$—CH=CH—CO—, —$CH_2$—CH=CH—$CH_2$—CO—, —$CH_2$—CH=CH—$CH_2$—$CH_2$—CO—, —$CH_2$—CH=CH—$CH_2$—$CH_2$—$CH_2$—CO—, —$CH_2$—CH=CH—$CH_2$—$CH_2$—$CH_2$—$CH_2$—CO;
—CO—$CH_2$—;
—CO—O—CO—, —CO—O—$CH_2$—CO—, —CO—O—$CH_2$—$CH_2$—CO—,
—CO—O—$CH_2$—$CH_2$—$CH_2$—CO—, —CO—O—$CH_2$—$CH_2$—$CH_2$—$CH_2$—CO—;
—$SO_2$-Ph-CO—, —$SO_2$-Ph-$CH_2$—CO—, —$SO_2$-Ph-$CH_2$—$CH_2$—CO—,
—$SO_2$-Ph-$CH_2$—$CH_2$—$CH_2$—CO—, or —$SO_2$-Ph-$CH_2$—$CH_2$—$CH_2$—$CH_2$—CO—.

In one embodiment of the present invention, B is an aptamer, and the aptamer is AS1411 or Sgc8c.

In one embodiment of the present invention, the triptolide derivative of Formula (IV) is a compound having the following structure:

| No. | $R_1$ | $R_2$ | $R_3$ | $R_4$ | $R_5$ | $R_6$ | $R_7$ | G | M | Z | X | A | B |
|---|---|---|---|---|---|---|---|---|---|---|---|---|---|
| (56) | H | H | H | H | H | H | H | O | OH | O | O | —CO—$CH_2$—CO— | AS1411 |
| (57) | H | H | H | H | H | H | H | O | OH | O | O | —CH=CH—$CH_2$—CO— | AS1411 |
| (58) | H | H | H | H | H | H | H | O | OH | O | O | —CH=CH—CO— | AS1411 |
| (59) | H | H | H | H | H | H | H | O | OH | O | O | —$CH_2$—Ph—$CH_2$—CO— | AS1411 |
| (60) | H | H | H | H | H | H | H | O | OH | O | O | —CO—NH—$CH_2$—CO— | AS1411 |
| (61) | H | H | H | H | H | H | H | O | OH | O | O | —$CH_2$—CH=CH—$CH_2$—CO— | AS1411 |
| (62) | H | H | H | H | H | H | H | O | OH | O | O | —CO—O—$CH_2$—CO— | AS1411 |
| (63) | H | H | H | H | H | H | H | O | OH | O | O | —$SO_2$—Ph—$CH_2$—CO— | AS1411 |

-continued

| No. | $R_1$ | $R_2$ | $R_3$ | $R_4$ | $R_5$ | $R_6$ | $R_7$ | G | M | Z | X | A | B |
|---|---|---|---|---|---|---|---|---|---|---|---|---|---|
| (64) | H | H | H | H | H | H | H | O | OH | O | O | —CO—CH$_2$—CH$_2$—CO— | AS1411 |
| (70) | H | H | H | H | H | H | H | O | OH | O | O | —CO—CH$_2$—CO— | Sgc8c |
| (71) | H | H | H | H | H | H | H | O | OH | O | O | —CH=CH—CH$_2$—CO— | Sgc8c |
| (72) | H | H | H | H | H | H | H | O | OH | O | O | —CH=CH—CO— | Sgc8c |
| (73) | H | H | H | H | H | H | H | O | OH | O | O | —CH$_2$—Ph—CH$_2$—CO— | Sgc8c |
| (74) | H | H | H | H | H | H | H | O | OH | O | O | —CO—NH—CH$_2$—CO— | Sgc8c |
| (75) | H | H | H | H | H | H | H | O | OH | O | O | —CH$_2$—CH=CH—CH$_2$—CO— | Sgc8c |
| (76) | H | H | H | H | H | H | H | O | OH | O | O | —CO—O—CH$_2$—CO— | Sgc8c |
| (77) | H | H | H | H | H | H | H | O | OH | O | O | —SO$_2$—Ph—CH$_2$—CO— | Sgc8c |
| (78) | H | H | H | H | H | H | H | O | OH | O | O | —CO—CH$_2$—CH$_2$—CO— | Sgc8c |

The present invention further provides a method for preparing the novel triptolide derivative, and the method comprises:

1) reacting triptolide or a modified compound thereof with a linking intermediate in an organic solvent at a temperature of from −20° C. to 100° C. and optionally in the presence of a catalyst;

2) reacting an aptamer in an alkaline solution with the product obtained from step 1) in an organic solvent at a temperature of from 0° C. to room temperature.

In one embodiment of the present invention, where the aptamer is combined to the triptolide or a modified compound thereof at $C_{18}$ or $C_{12}$, the method further comprises performing a protection reaction for hydroxyl at $C_{14}$ with a protection agent, and the protection agent is selected from tert-butyldimethylsilyl triflate or benzyl bromide.

In one embodiment of the present invention, the organic solvent in step 1) is selected from pyridine, dichloromethane, acetonitrile, N-methyl morpholine, dimethylsulfoxide, triethylamine or N, N-dimethyl pyridine, or two or more of the combinations thereof.

In one embodiment of the present invention, the catalyst in step 1) is silver oxide.

In one embodiment of the present invention, the alkaline solution in step 2) is selected from a buffer of sodium carbonate/sodium bicarbonate, triethylamine or potassium carbonate, or two or more of the combinations thereof; in one embodiment of the present invention, the pH of the buffer of sodium carbonate/sodium bicarbonate is 9.0.

In one embodiment of the present invention, the alkaline solution in step 2) of the method for preparing the triptolide derivative is selected from a buffer of sodium carbonate/sodium bicarbonate, triethylamine or potassium carbonate, or two or more of the combinations thereof.

In one embodiment of the present invention, the organic solvent in step 2) of the method for preparing the triptolide derivative is selected from dichloromethane, dimethylsulfoxide, acetonitrile or 4-(4,6-dimethoxy-1,3,5-triazin-2-yl)-4-methyl-morpholine salt (DMT-MM), or two or more of the combinations thereof.

In one embodiment of the present invention, the linking intermediate in step 2) of the method for preparing the triptolide derivative is selected from succinic anhydride, phosgene, allyl bromide, propiolic acid, 4-bromomethyl benzoic acid, isocyanate, acyl chloride, chloroformate, benzenesulfonyl chloride, 2-bromoacetyl chloride or 4-bromo-2-butenoate or an analog thereof.

The linking intermediates in the method of the present invention are small molecular compounds known in the field. They can be commercially available or prepared by a person having ordinary skill in the art based on the disclosure of the existing technologies. The small molecular compounds of the linking intermediate comprises but not limited to succinic anhydride, phosgene, propiolic acid, ethyl 4-bromo(methoxy)methyl benzoate, ethyl 4-bromomethyl benzoate, methyl isocyanate, methyl 4-bromo-2-butene, chloroformate, 2-bromine acyl chloride, methyl 4-sulfonyl chlorobenzoate or an analog thereof.

In one embodiment of the present invention, the triptolide and a modified compound thereof applied in the method are compounds known in the art. They can be commercially available or prepared by a person having ordinary skill in the art based on the disclosure of the existing technologies. They comprise but not limited to tripdiolide, triptonide, wilforlide, 16-hydroxytriptolide or triptriolide.

The aptamer in the invention comprises but not limited to AS1411 or Sgc8c, and it may be other known aptamer having similar properties. The aptamers can be commercially available or prepared by a person having ordinary skill in the art based on the disclosure of the existing technologies.

The method of the present invention relates to various reaction intermediates and target products. An isolation and purification step may be conducted based on the need of the subsequent reaction. Said step may be performed by one person having ordinary skill in the art according to common knowledge in the field and ordinary methods for separation and purification, and the method of separation and purification comprises but not limited to filtration, phase separation, crystallization, adsorption, chromatography and so forth, which are ordinary methods in the field.

In the present invention, a person having ordinary skill in the art can determine the degree of completion of the reaction of each reaction by the method comprising but not limited to eye observation, TLC, HPLC. One person having ordinary skill in the art can operate the above methods with common knowledge according to their needs.

In one embodiment of the present invention, where succinic anhydride or an analog is used as the linking intermediate for preparing a derivative of the novel triptolide or a modified compound thereof combined with the aptamer, in which A group being —CO—(CH$_2$)$_n$—CO—; the succinic anhydride or an analog thereof comprises but not limited to malonic anhydride, succinic anhydride, glutaric anhydride, heptanoic anhydride or so forth;

the preparation method can be performed by ordinary preparation method in the field, in one embodiment of the present invention, the preparation method comprises:

adding succinic anhydride or an analog thereof into a pyridine solution having dissolved triptolide or a modified compound thereof under room temperature; then under the protection of nitrogen gas, heating the reaction system to a temperature of 70° C. to 100° C.; the temperature decreases to the room temperature when the reaction is complete, and obtaining the intermediate product by separation and purification; subsequently, dissolving the obtained intermediate product in dimethyl sulfoxide (DMSO) (or a solvent having similar properties), dissolving DMT-MM in distilled water and, meanwhile, dissolving an aptamer in an alkaline buffer; afterwards, introducing both the intermediate product in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where succinic anhydride is used as the linking intermediate for preparing the compound of Formula (II), in which the aptamer is combined to $C_{14}$, the synthetic route is as follows:

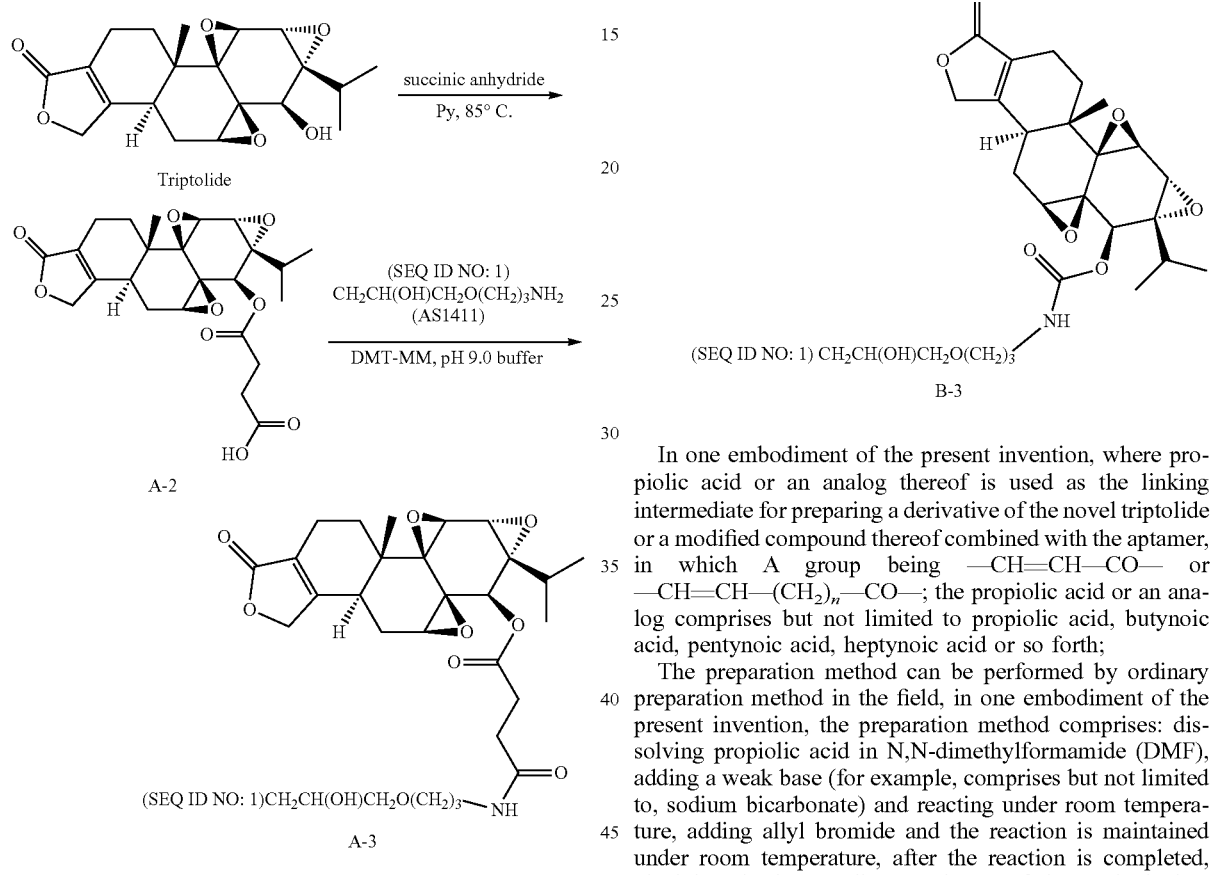

In one embodiment of the present invention, where phosgene is used as the linking intermediate for preparing the compound of Formula (II), in which the aptamer is combined to $C_{14}$, the synthetic route is as follows:

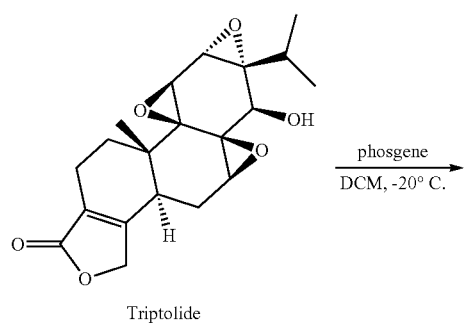

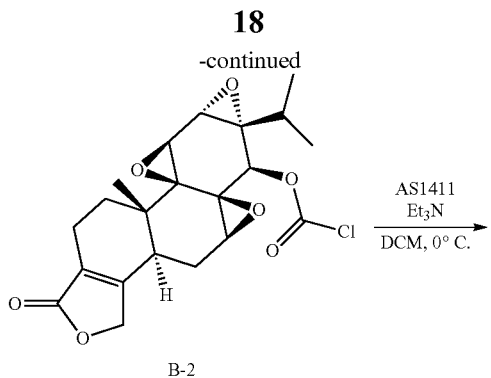

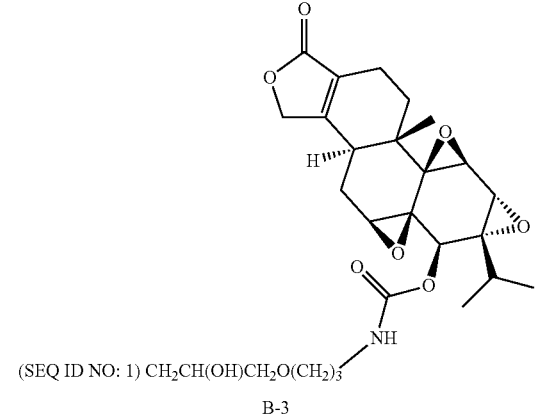

In one embodiment of the present invention, where propiolic acid or an analog thereof is used as the linking intermediate for preparing a derivative of the novel triptolide or a modified compound thereof combined with the aptamer, in which A group being —CH=CH—CO— or —CH=CH—(CH$_2$)$_n$—CO—; the propiolic acid or an analog comprises but not limited to propiolic acid, butynoic acid, pentynoic acid, heptynoic acid or so forth;

The preparation method can be performed by ordinary preparation method in the field, in one embodiment of the present invention, the preparation method comprises: dissolving propiolic acid in N,N-dimethylformamide (DMF), adding a weak base (for example, comprises but not limited to, sodium bicarbonate) and reacting under room temperature, adding allyl bromide and the reaction is maintained under room temperature, after the reaction is completed, obtaining the intermediate product-1 of the method; then dissolving triptolide or a modified compound thereof and the intermediate product-1 in a solvent acetonitrile, subsequently adding N-methylmorpholine (NMM), allowing the reaction to react completely under room temperature so as to obtain the intermediate product-2 of the method; next, dissolving the intermediate product-2 in tetrahydrofuran, adding morpholine and tetrakistriphenylphosphine palladium and and allowing the reaction to react completely under room temperature so as to obtain the intermediate product-3 of the method; further, dissolving the intermediate product-3 in dimethyl sulfoxide (DMSO) (or a solvent having similar properties), dissolving DMT-MM in distilled water, dissolving an aptamer in an alkaline buffer; afterwards, introducing both the intermediate product in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where propiolic acid is used as the linking intermediate for preparing the compound of Formula (II), in which the aptamer is combined to $C_{14}$, the synthetic route is as follows:

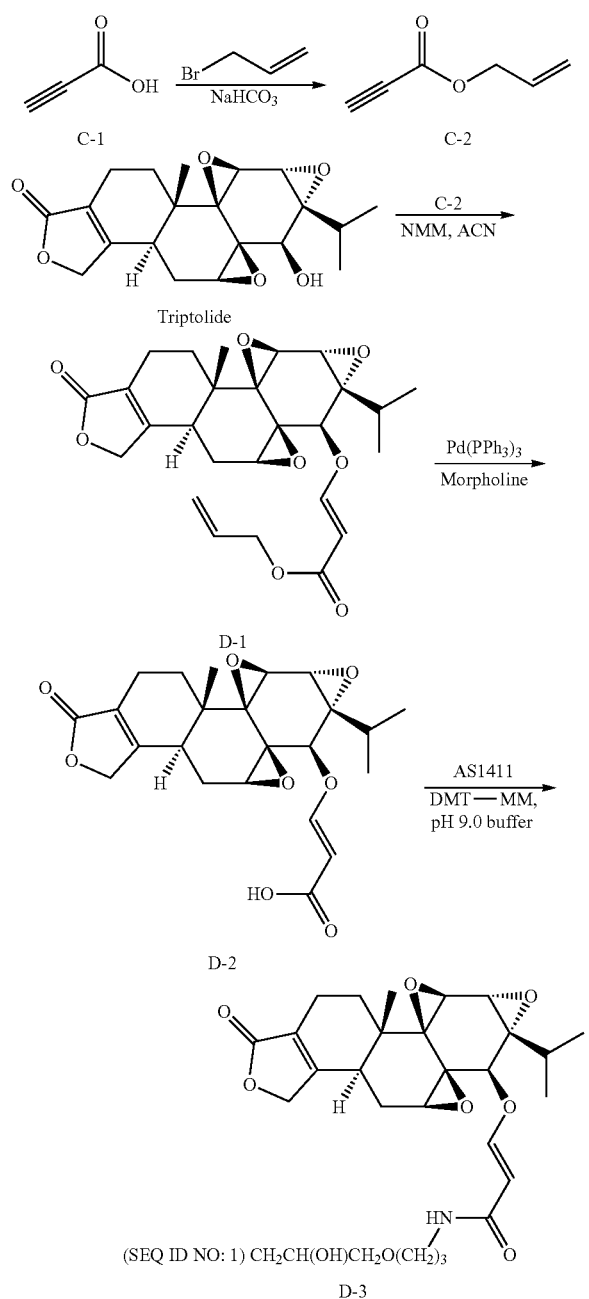

In one embodiment of the present invention, where methyl 4-bromo (methoxy) methylbenzoate or an analog thereof is used as the linking intermediate for preparing a derivative of the novel triptolide or a modified compound thereof combined with the aptamer, in which A group being —CH(OCH$_3$)-Ph-CO—, CH(OCH$_3$)-Ph-(CH$_2$)$_n$—CO—; methyl 4-bromo (methoxy) methylbenzoate or an analog thereof comprises but not limited to methyl 4-bromo (methoxy) methylbenzoate, methyl 4-bromo (methoxy) methylphenylacetate, methyl 4-bromo (methoxy) methylphenylpropionate, methyl 4-bromo (methoxy) methylphenylbutyrate, or the ethyl ester, propyl ester, butyl ester thereof or so forth.

The preparation method can be performed by ordinary preparation method in the field, in one embodiment of the present invention, the preparation method comprises:

dissolving triptolide or a modified compound thereof in DMF at 0° C. and in the presence of nitrogen gas, adding methyl 4-bromo (methoxy) methylbenzoate or an analog thereof and a catalyst; allowing the reaction to react completely so as to obtain the intermediate product-1 of the method; at 0° C., dissolving the intermediate product-1 in dichloromethane (DCM), adding sodium hydroxide solution and allowing the reaction to react completely at 0° C. so as to obtain the intermediate product-2 of the method; then, dissolving the intermediate product-2 in dimethyl sulfoxide (DMSO) (or a solvent having similar properties), dissolving DMT-MM in distilled water, dissolving an aptamer in an alkaline buffer; introducing both the intermediate product in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where methyl 4-bromo (methoxy) methyl benzoate is used as the linking intermediate for preparing a compound of Formula (II), in which the aptamer is combined to $C_{14}$, the synthetic route is as follows:

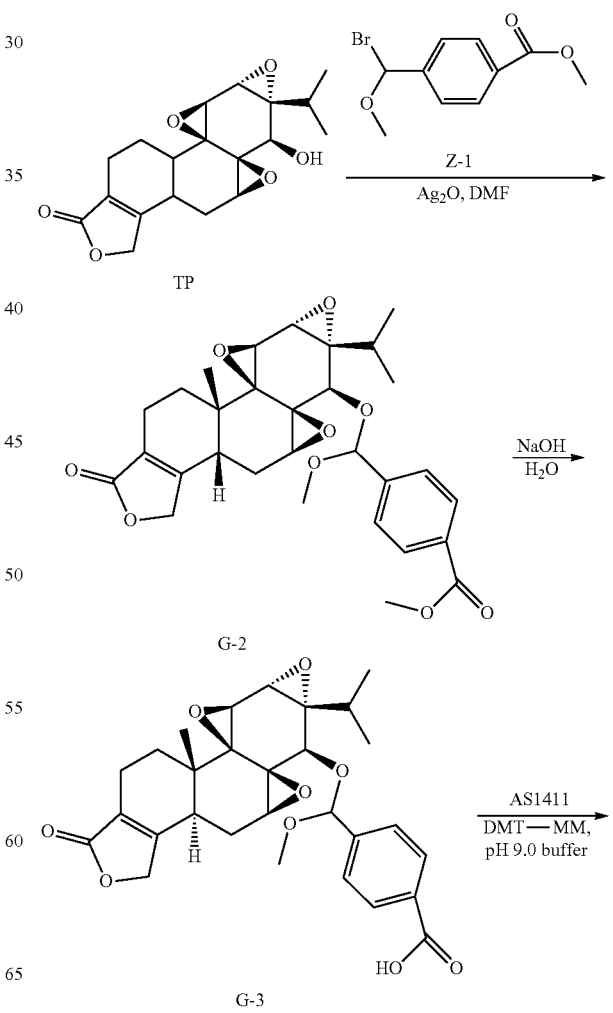

-continued

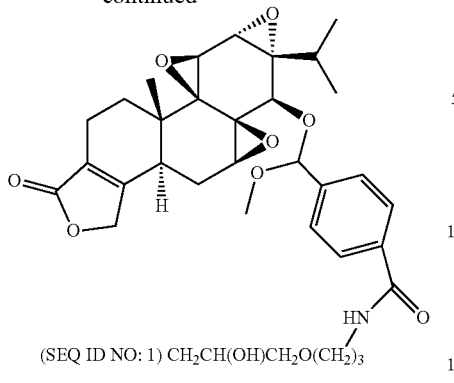

(SEQ ID NO: 1) CH₂CH(OH)CH₂O(CH₂)₃

G-4

In one embodiment of the present invention, where methyl 4-bromomethyl phenylacetate or an analog thereof is used as the linking intermediate for preparing a derivative of the novel triptolide or a modified compound thereof combined with the aptamer, in which A group being —CH₂-Ph-CO— or CH₂-Ph-(CH₂)$_n$—CO—; methyl 4-bromomethyl phenylacetate or an analog thereof comprises but not limited to methyl 4-bromomethyl benzoate, methyl 4-bromomethyl phenylacetate, methyl 4-bromomethyl phenylpropionate, methyl 4-bromomethyl phenylbutyrate or the ethyl ester, propyl ester, butyl ester thereof or so forth;

The preparation method can be performed by ordinary preparation method in the field, in one embodiment of the present invention, the preparation method comprises:

dissolving triptolide or a modified compound thereof in DMF at 0° C. and in the presence of nitrogen gas, adding methyl 4-bromomethyl phenylacetate or an analog thereof and a catalyst; allowing the reaction to react completely so as to obtain the intermediate product-1 of the method; at 0° C., dissolving the intermediate product-1 in dichloromethane (DCM), adding sodium hydroxide solution and allowing the reaction to react completely at 0° C. so as to obtain the intermediate product-2 of the method; then, dissolving the intermediate product-2 in dimethyl sulfoxide (DMSO) (or a solvent having similar properties), dissolving DMT-MM in distilled water, dissolving an aptamer in an alkaline buffer; introducing both the intermediate product in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where methyl 4-bromomethyl phenylacetate is used as the linking intermediate for preparing a compound of Formula (II), in which the aptamer is combined to C₁₄, the synthetic route is as follows:

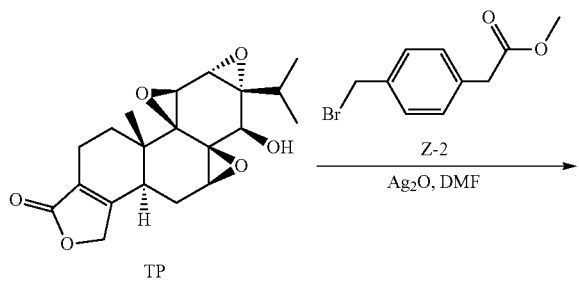

-continued

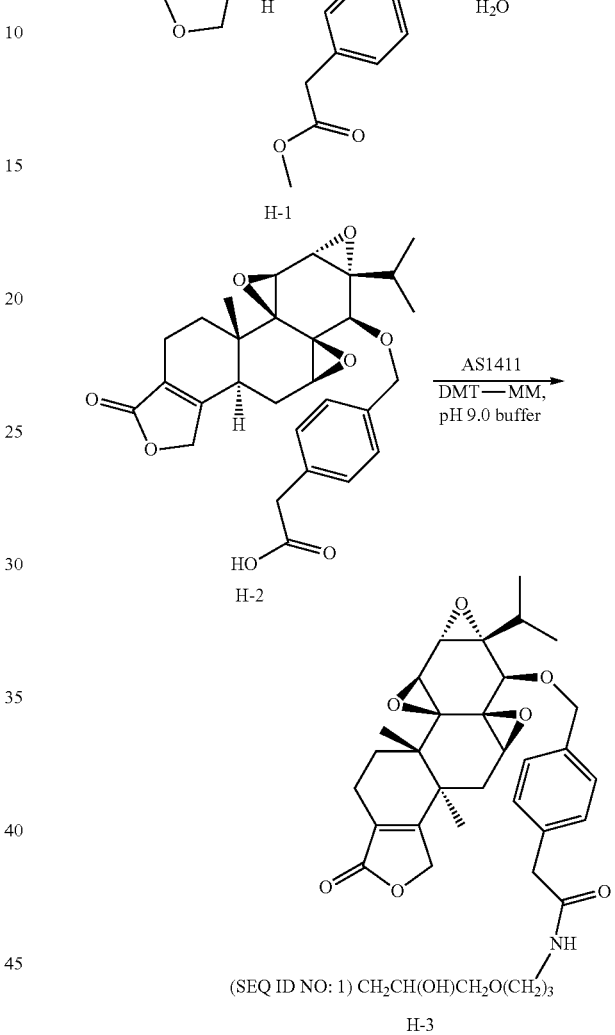

In one embodiment of the present invention, where methyl isocyanate or an analog thereof is used as the linking intermediate for preparing a derivative of the novel triptolide or a modified compound thereof combined with the aptamer, in which A group being —CO—NH—CO— or —CO—NH—(CH₂)$_n$—CO—; methyl isocyanate or an analog thereof comprises but not limited to methyl isocyanate, methyl isocyanatoformate, methyl isocyanatopropionate, methyl isocyanatobutyrate or the ethyl ester, propyl ester, butyl ester thereof or so forth;

The preparation method can be performed by ordinary preparation method in the field, in one embodiment of the present invention, the preparation method comprises:

dissolving triptolide or a modified compound thereof and triethylamine in dichloromethane, then adding methyl isocyanate or an analog thereof, allowing the reaction to react completely under room temperature so as to obtain the intermediate product-1 of the method; at 0° C., dissolving the intermediate product-1 in DCM, adding sodium hydroxide solution and the reaction is remained at this temperature, the reaction is sufficiently reacted, and allowing the reaction to react completely under the same temperature condition so as to obtain the intermediate product-2 of the method; under room temperature, dissolving the intermediate product-2 in DMF, then adding hydroxybenzotriazole (HOBT) and 1-ethyl-3-(3-dimethylaminopropyl) carbodiimide hydrochloride (EDCI), allowing the reaction to react completely under room temperature, introducing an aptamer to continue the reaction and then obtaining the corresponding novel triptolide derivative of the invention.

In one embodiment of the present invention, where methyl isocyanate is used as the linking intermediate for preparing the compound of Formula (II), in which the aptamer is combined to $C_{14}$, the synthetic route is as follows:

In one embodiment of the present invention, where methyl 4-bromo-2-butenoate or an analog thereof is used as the linking intermediate for preparing a derivative of the novel triptolide or a modified compound thereof combined with the aptamer, in which A group being —$CH_2$—CH=CH—CO—, —$CH_2$—CH=CH—$(CH_2)_n$—CO—; methyl 4-bromo-2-butenoate or an analog thereof comprises but not limited to methyl 4-bromo-2-butenoate, methyl 4-bromo-2-pentenoate, methyl 4-bromo-2-hexenoate, methyl 4-bromo-2-heptenoate, methyl 4-bromo-2-octenoate or the ethyl ester, propyl ester, butyl ester thereof or so forth;

The preparation method can be performed by ordinary preparation method in the field, in one embodiment of the present invention, the preparation method comprises:

dissolving triptolide or a modified compound thereof in DMF at 0° C. and in the presence of nitrogen gas, then adding methyl 4-bromo-2-butenoate or an analog thereof and a catalyst; allowing the reaction to react completely under room temperature so as to obtain the intermediate product-1 of the method; at 0° C., dissolving the intermediate product-1 in dichloromethane, adding sodium hydroxide solution, allowing the reaction to react completely at said temperature condition so as to obtain the intermediate product-2 of the method; then, dissolving the intermediate product-2 in dimethyl sulfoxide (DMSO) (or a solvent having similar properties), dissolving DMT-MM in distilled water, dissolving an aptamer in an alkaline buffer; introducing both the intermediate product in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where methyl 4-bromo-2-butenoate is used as the linking intermediate for preparing a compound of Formula (II), in which the aptamer is combined to $C_{14}$, the synthetic route is as follows:

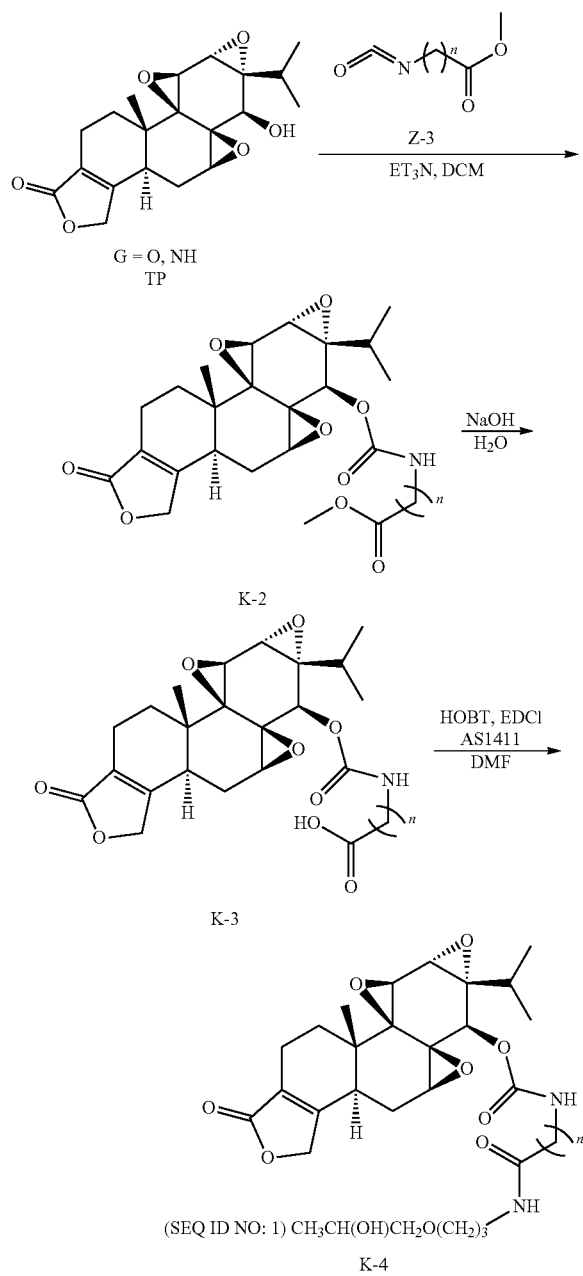

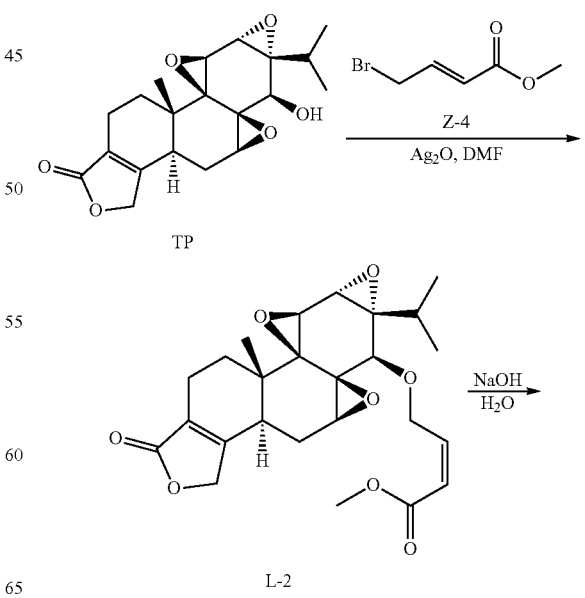

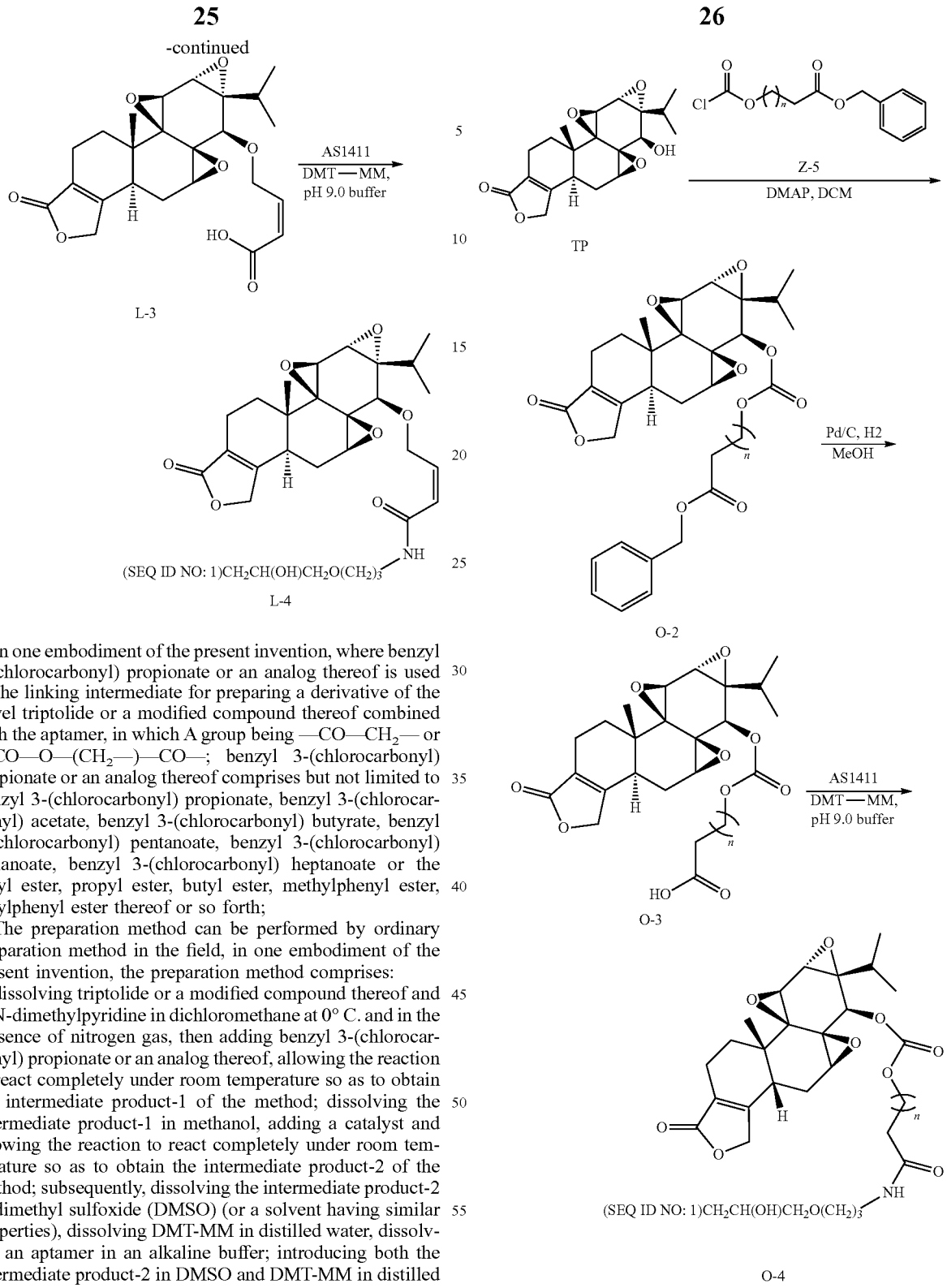

In one embodiment of the present invention, where benzyl 3-(chlorocarbonyl) propionate or an analog thereof is used as the linking intermediate for preparing a derivative of the novel triptolide or a modified compound thereof combined with the aptamer, in which A group being —CO—$CH_2$— or —CO—O—($CH_2$—)—CO—; benzyl 3-(chlorocarbonyl) propionate or an analog thereof comprises but not limited to benzyl 3-(chlorocarbonyl) propionate, benzyl 3-(chlorocarbonyl) acetate, benzyl 3-(chlorocarbonyl) butyrate, benzyl 3-(chlorocarbonyl) pentanoate, benzyl 3-(chlorocarbonyl) hexanoate, benzyl 3-(chlorocarbonyl) heptanoate or the ethyl ester, propyl ester, butyl ester, methylphenyl ester, ethylphenyl ester thereof or so forth;

The preparation method can be performed by ordinary preparation method in the field, in one embodiment of the present invention, the preparation method comprises:

dissolving triptolide or a modified compound thereof and N,N-dimethylpyridine in dichloromethane at 0° C. and in the presence of nitrogen gas, then adding benzyl 3-(chlorocarbonyl) propionate or an analog thereof, allowing the reaction to react completely under room temperature so as to obtain the intermediate product-1 of the method; dissolving the intermediate product-1 in methanol, adding a catalyst and allowing the reaction to react completely under room temperature so as to obtain the intermediate product-2 of the method; subsequently, dissolving the intermediate product-2 in dimethyl sulfoxide (DMSO) (or a solvent having similar properties), dissolving DMT-MM in distilled water, dissolving an aptamer in an alkaline buffer; introducing both the intermediate product-2 in DMSO and DMT-MM in distilled water to the alkaline buffer having the aptamer at the same time, allowing the reaction to react sufficiently under room temperature, and then obtaining the corresponding novel triptolide derivative of the invention.

In one embodiment of the present invention, where benzyl 3-(chlorocarbonyl) propionate is used as the linking intermediate for preparing a compound of Formula (II), in which the aptamer is combined to $C_{14}$, the synthetic route is as follows:

In one embodiment of the present invention, where 2-bromoacetyl chloride or an analog thereof is used as the linking intermediate for preparing a derivative of the novel triptolide or a modified compound thereof combined with the aptamer, in which A group being —CO—$CH_2$— or —CO—O—($CH_2$)—CO—; 2-bromoacetyl chloride or an analog thereof comprises but not limited to 2-bromoacetyl chloride, 2-bromoformyl chloride, 2-bromopropionyl chloride, 2-bromobutyryl chloride, 2-bromopentanoyl chloride, 2-bromohexanoyl chloride, 2-bromoheptanoyl chloride or so forth;

The preparation method can be performed by ordinary preparation method in the field, in one embodiment of the present invention, the preparation method comprises:

dissolving triptolide or a modified compound thereof in DMF at 0° C. and in the presence of nitrogen gas, adding benzyl bromide and a catalyst; allowing the reaction to react completely under room temperature so as to obtain the intermediate product-1 of the method; dissolving the intermediate product-1 in tetrahydrofuran (THF), adding sodium hydroxide solution, increasing the temperature of the reaction system to 50~75° C. for complete reaction so as to obtain the intermediate product-2 of the method; dissolving the intermediate product-2 in dichloromethane, adding triethylamine, slowly adding methoxycarbonyl benzenesulfonyl chloride in dichloromethane dropwise to the mixture at 0° C., after the addition, increasing the temperature of the reaction system to reach the room temperature naturally, and then allowing the reaction to react completely so as to obtain the target product-3 of the method; dissolving the target product-3 in THF, adding 50 mg of 10% Pd/C, replacing the gas in the atmosphere with hydrogen, allowing the reaction to react under room temperature for 5 hours while TLC is used to monitor the reaction; after the reaction is completed, performing suction filtration to remove Pd/C and directly proceed with the next step; at 0° C., dissolving the resulting product of the above steps in DCM, adding lithium hydroxide solution, allowing the reaction to react completely under said temperature condition so as to obtain the corresponding novel triptolide derivative of the invention.

In one embodiment of the present invention, where 2-bromoacetyl chloride is used as the linking intermediate for preparing a compound of Formula (II), in which the aptamer is combined to $C_{14}$, the synthetic route is as follows:

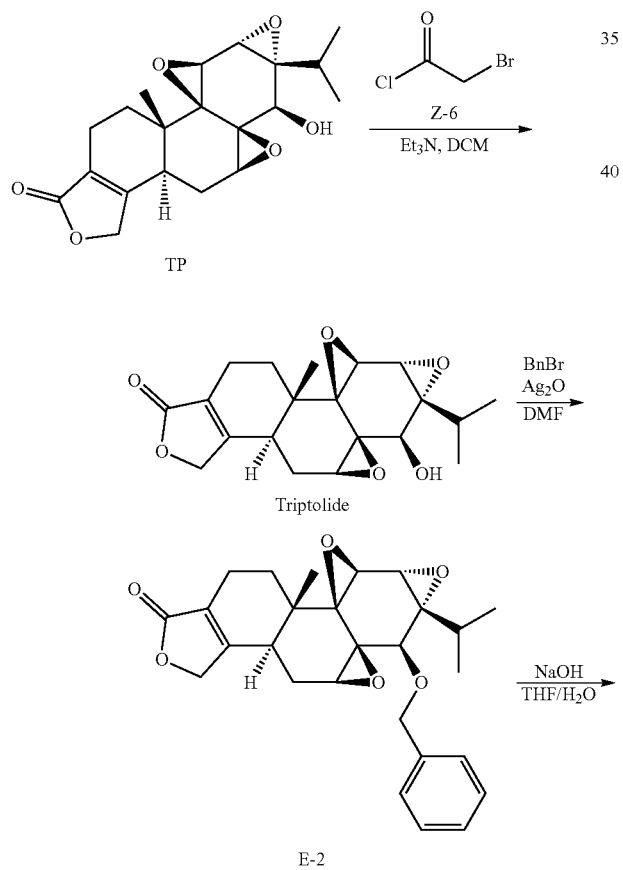

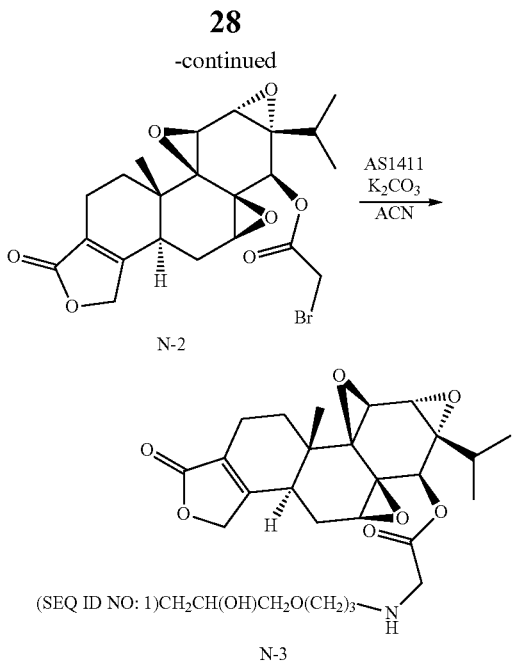

In one embodiment of the present invention, where methyl-4-(chlorosulfonyl)-benoate or an analog thereof is used as the linking intermediate for preparing a derivative of the novel triptolide or a modified compound thereof combined with the aptamer, in which A group being —$SO_2$-Ph-CO— or —$SO_2$-Ph-($CH_2$)—CO—; methyl bromo-2-butenoate or an analog thereof comprises but not limited to methyl-4-(chlorosulfonyl)-phenylacetate, methyl-4-(chlorosulfonyl)-phenylpropionate, methyl-4-(chlorosulfonyl)-phenylbutyrate, methyl-4-(chlorosulfonyl)-pentanoate, methyl-4-(chlorosulfonyl)-hexanoate, methyl-4-(chlorosulfonyl)-heptanoate, methyl-4-(chlorosulfonyl)-octanoate or the ethyl ester, propyl ester, butyl ester thereof or so forth.

In one embodiment of the present invention, where methyl-4-(chlorosulfonyl)-benoate is used as the linking intermediate for preparing a compound of Formula (III), in which the aptamer is combined to $C_{12}$, the synthetic route is as follows:

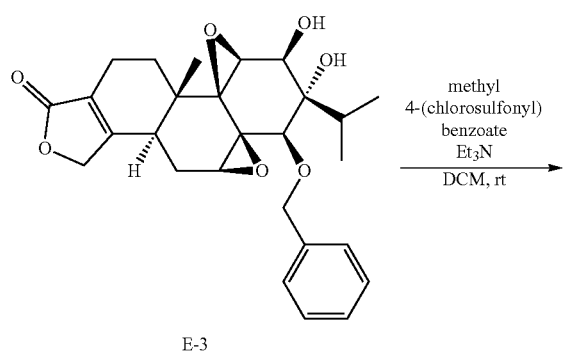

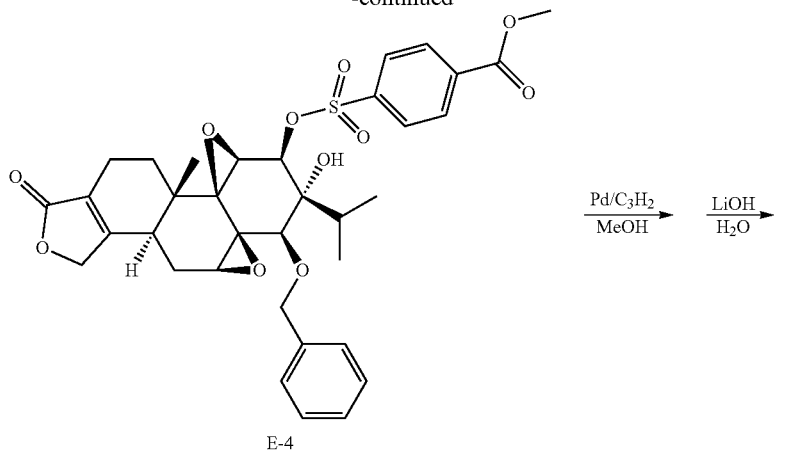
E-4
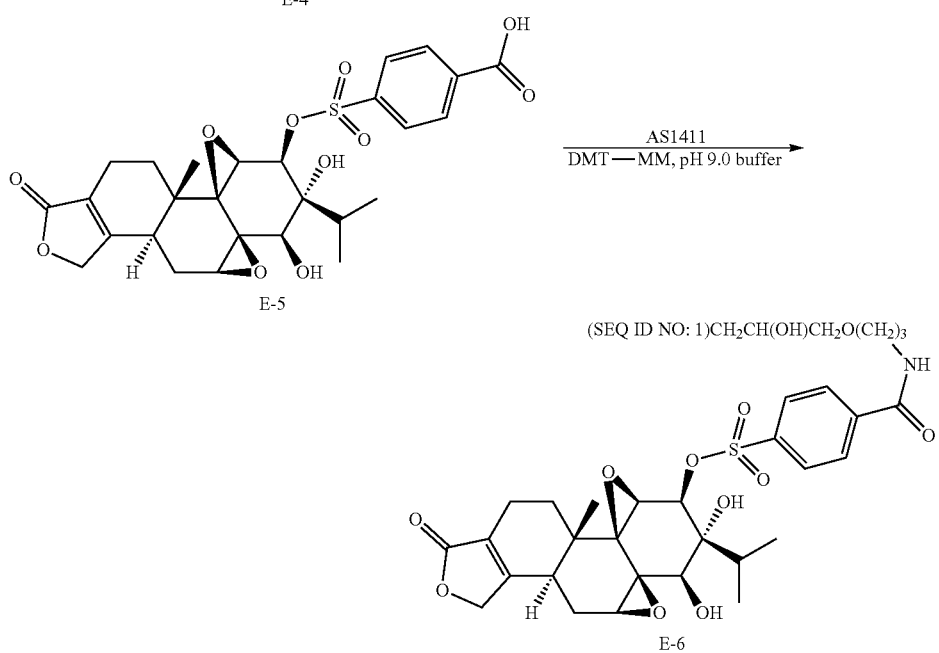
E-5
(SEQ ID NO: 1)CH₂CH(OH)CH₂O(CH₂)₃
E-6
In one embodiment of the present invention, where succinic anhydride is used as the linking intermediate for preparing a compound of Formula (IV), in which the aptamer is combined to $C_{18}$, the synthetic route is as follows:
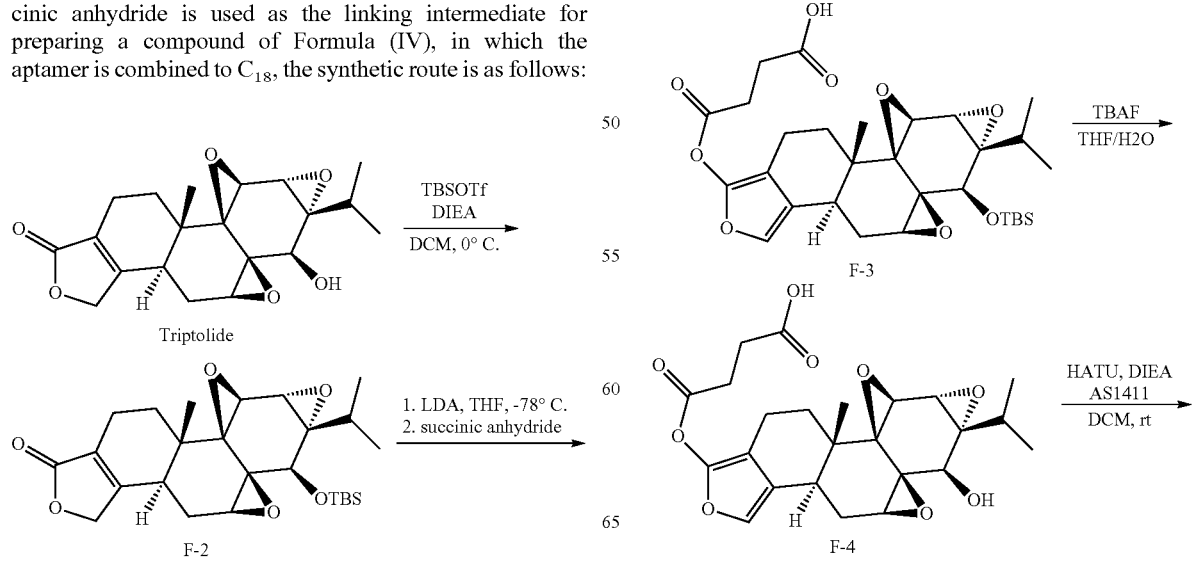

(SEQ ID NO: 1)CH$_2$CH(OH)CH$_2$O(CH$_2$)$_3$—NH

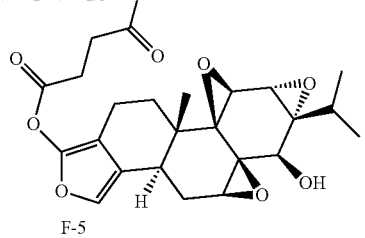

F-5

The methods illustrated by the above synthetic routes, using different linking intermediates, for preparing the novel triptolide derivatives of the present invention, are merely exemplified examples which use triptolide as the starting material. However, the above synthetic routes are not limited to triptolide, and they can also be applied on other modified compounds of triptolide having pharmaceutical activities for the preparation of novel derivatives with apatmers via combination. For example, a modified compound of triptolide comprises, but not limited to, tripdiolide, triptonide, wilforlide, 16-hydroxytriptolide or triptriolide.

The present invention further provides use of triptolide derivative of Formula (I) in the preparation of a medicament, i.e. the use in the preparation of a medicament for treating pancreatic cancer, renal cancer, small cell lung cancer, brain cancer, neural cancer, bone cancer, lymphoma, colon cancer, uterine cancer, breast cancer, leukemia, liver cancer, prostate cancer, skin cancer, melanoma and so forth.

According to the use in the preparation of a medicament of the invention, the novel triptolide derivatives of the present invention and suitable pharmaceutical excipients can be used for the preparation of various dosage forms such as, but not limited to, injection solution, oral dosage from and so forth. The route of administration can be, but not limited to, intramuscular injection, subcutaneous injection, intravenous injection, oral administration, and nasal administration and so forth.

DETAILED DESCRIPTION

Figures 1, 2:
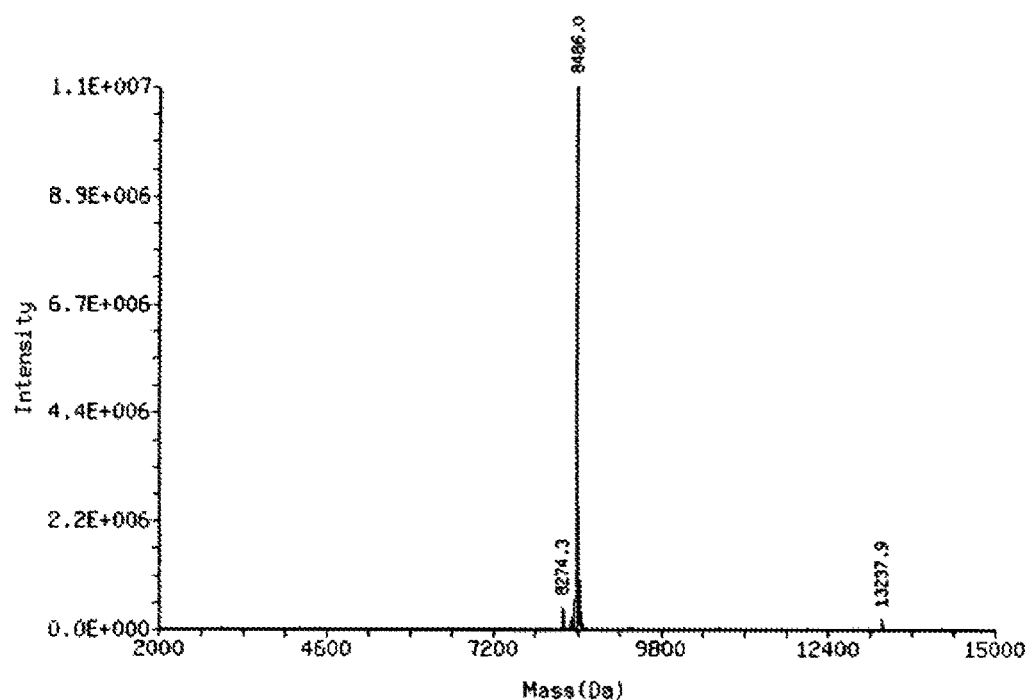
FIG. 1 is the mass spectrum of AS1411 in Embodiment 1.
FIG. 2 is the mass spectrum of Sgc8c in Embodiment 12.
Figure 3:
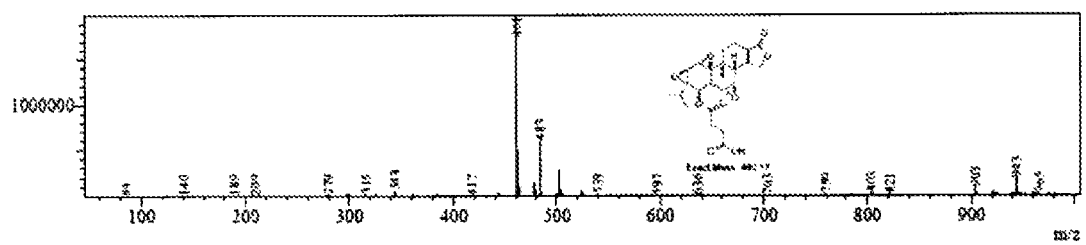
FIG. 3 is the LC-MS spectrum of A-2 in Embodiment 1.
Figure 4:
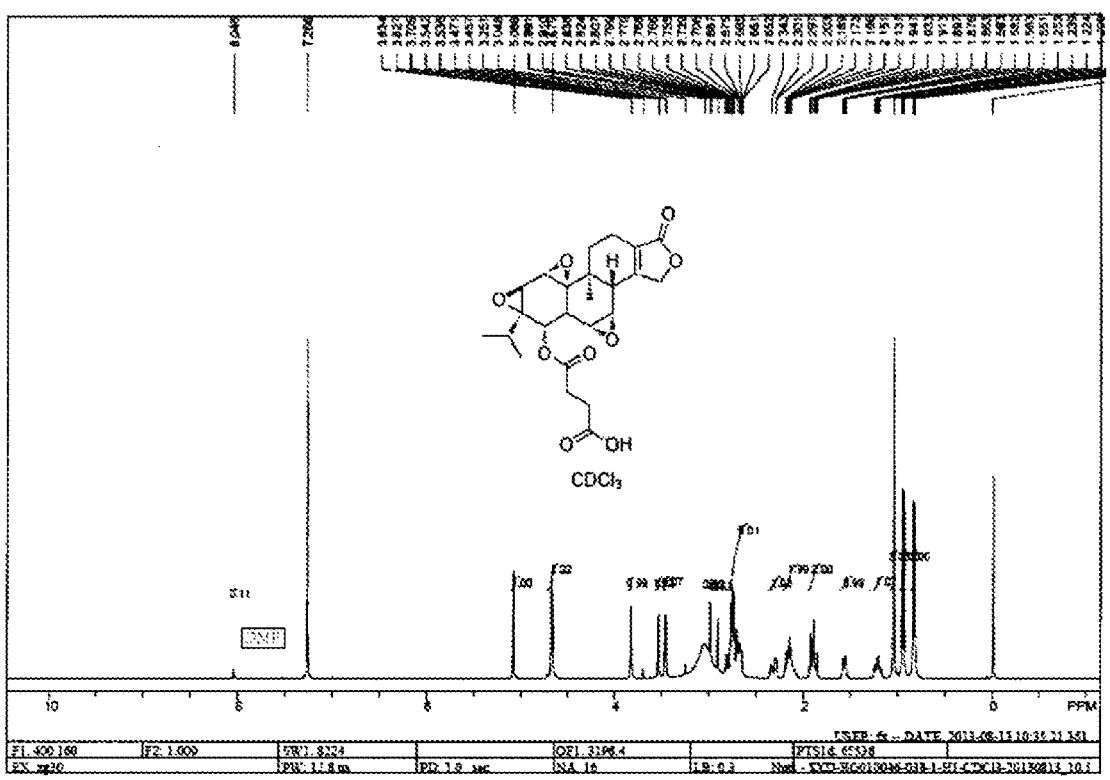
FIG. 4 is the H-NMR spectrum of A-2 in Embodiment 1.
Figure 5:
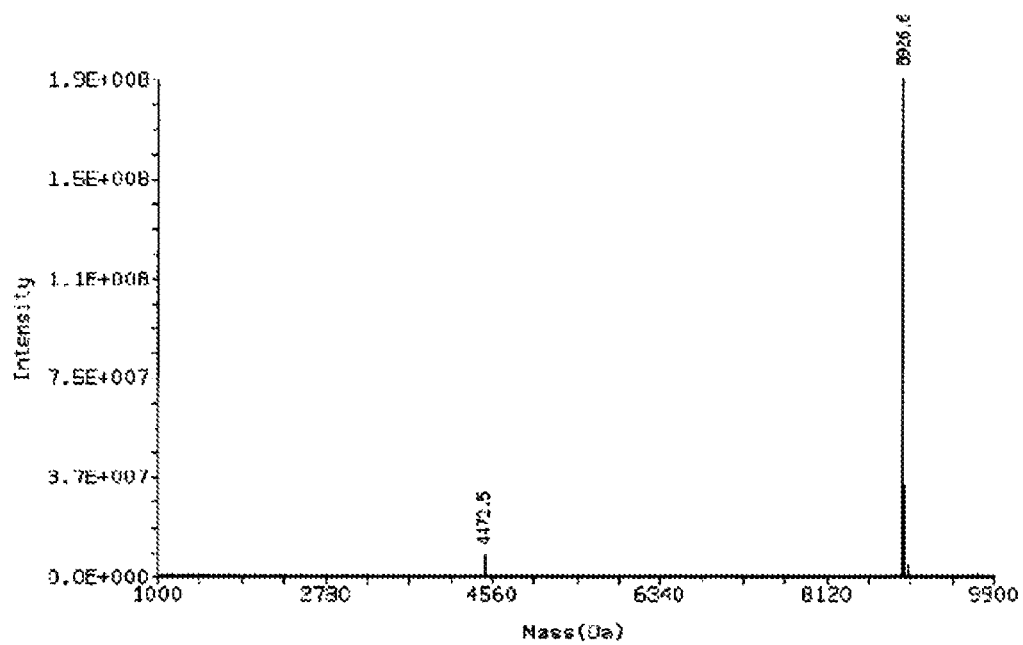
FIG. 5 is the LC-MS spectrum of A-3 (i.e. compound (1)) in Embodiment 1.
Figure 6:
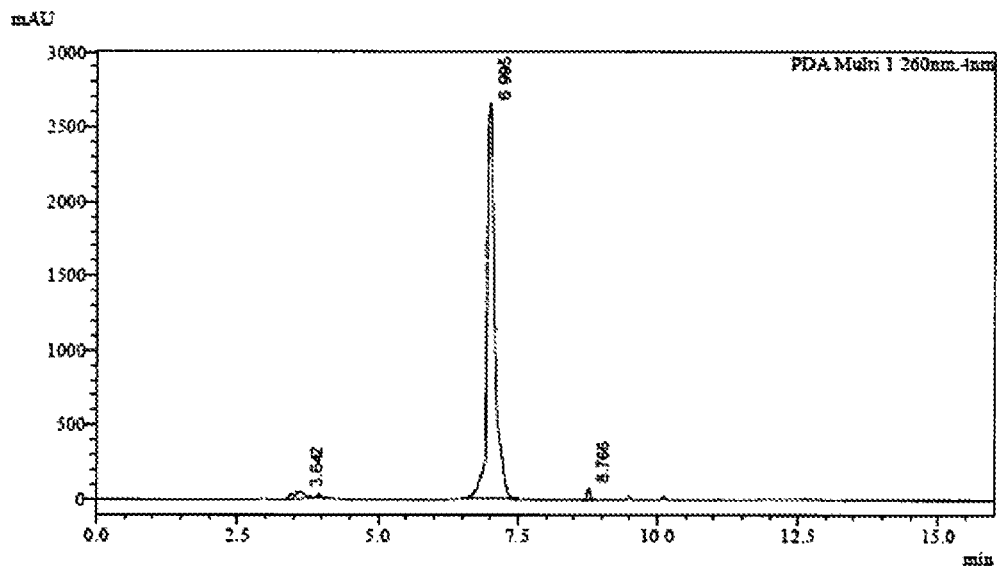
FIG. 6 is the HPLC spectrum of A-3 (i.e. compound (1)) in Embodiment 1.
Figure 7:
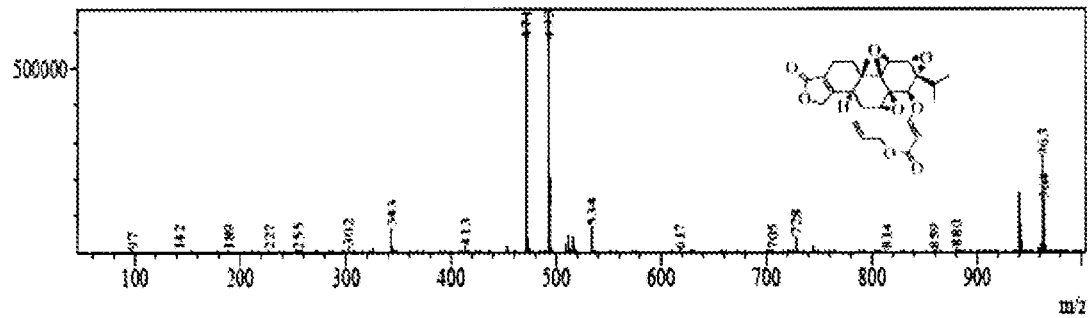
FIG. 7 is the LC-MS spectrum of D-1 in Embodiment 3.
Figure 8:
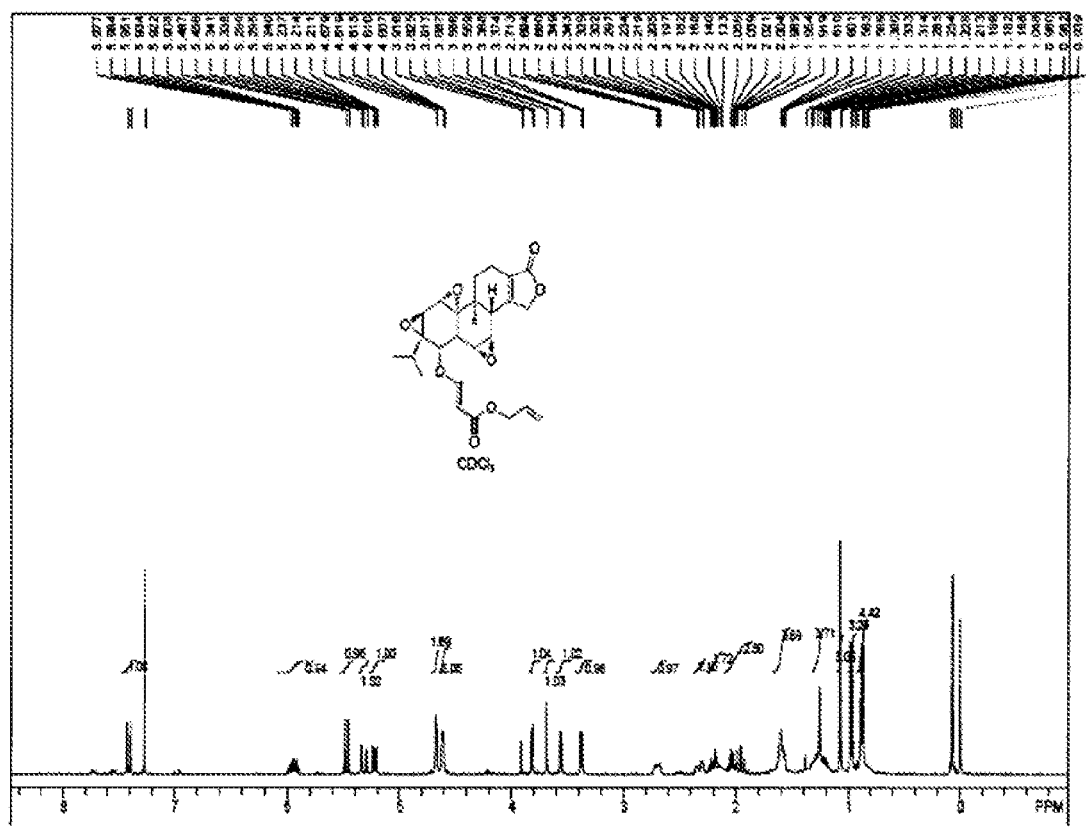
FIG. 8 is the H-NMR spectrum of D-1 in Embodiment 3.
Figure 9:
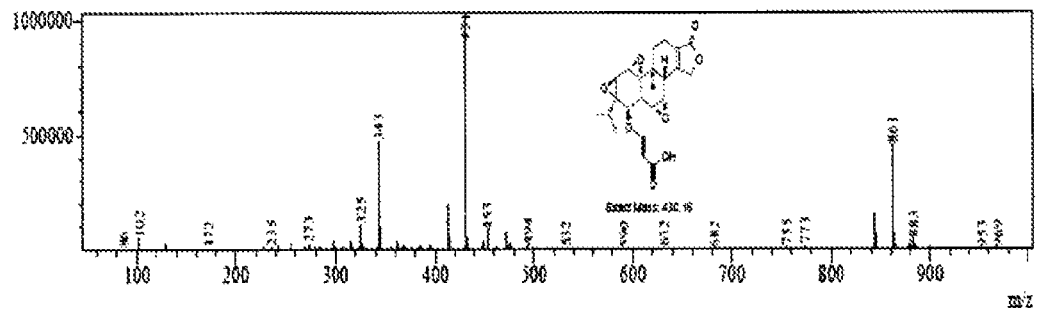
FIG. 9 is the LC-MS spectrum of D-2 in Embodiment 3.
Figure 10:
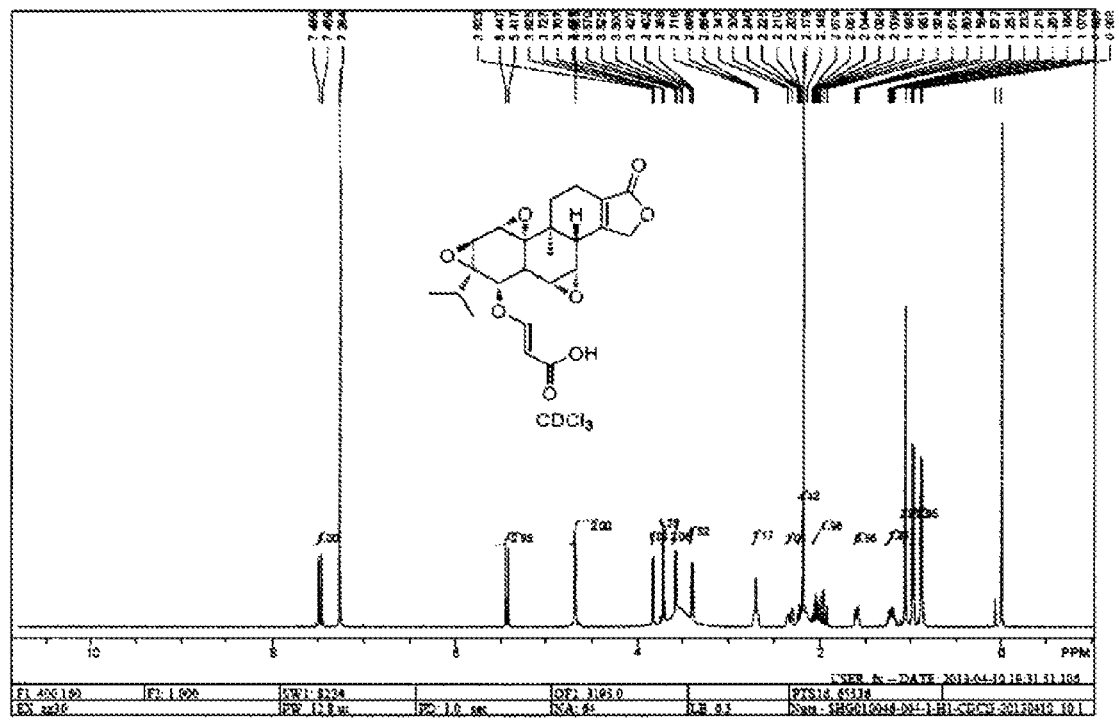
FIG. 10 is the H-NMR spectrum of D-2 in Embodiment 3.
Figure 11:
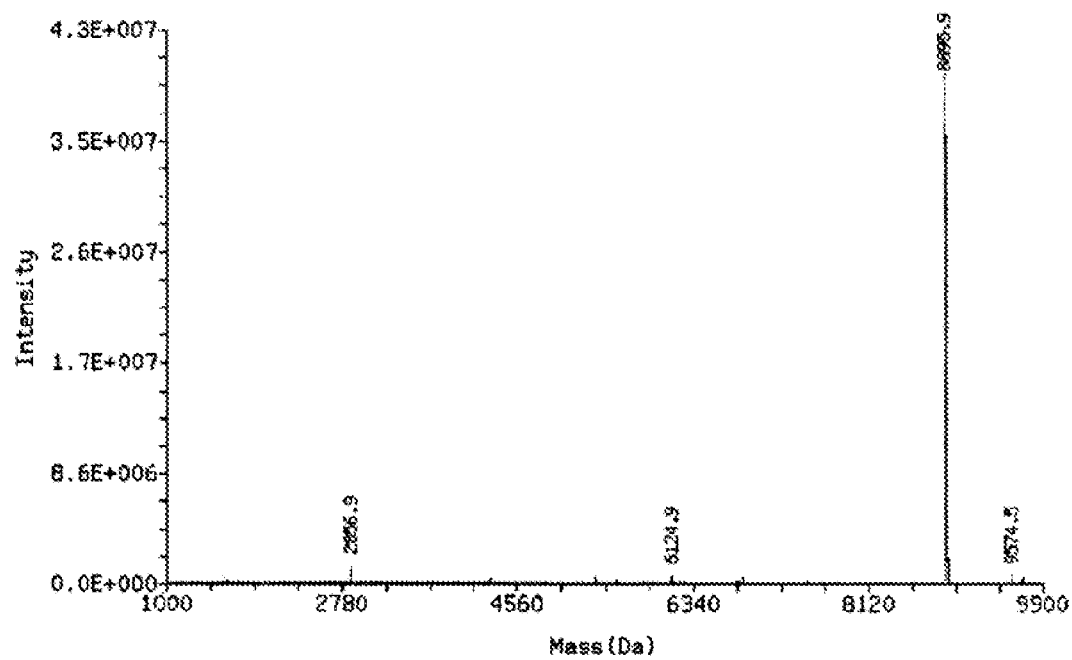
FIG. 11 is the LC-MS spectrum of D-3 (i.e. compound (3)) in Embodiment 3.
Figure 12:
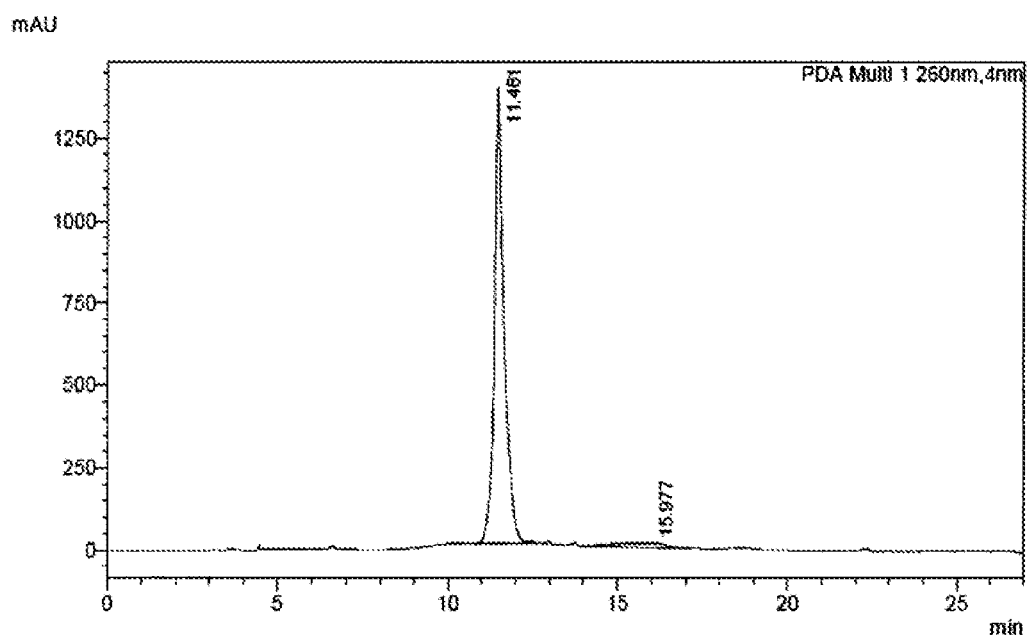
FIG. 12 is the HPLC spectrum of D-1 (i.e. compound (3)) in Embodiment 3.
Figure 13:
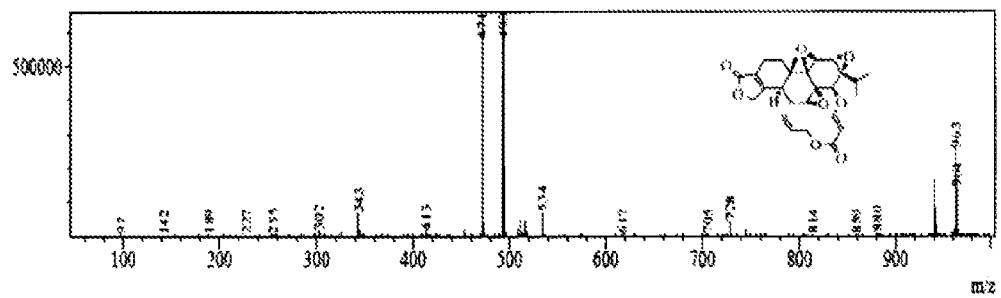
FIG. 13 is the LC-MS spectrum of W-1 in Embodiment 12.
Figure 14:
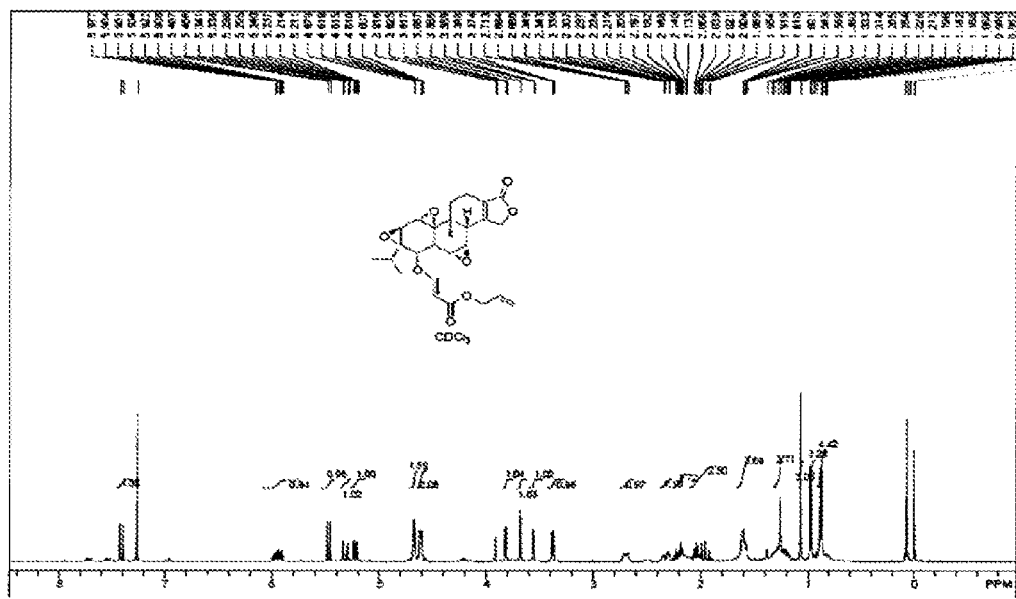
FIG. 14 is the H-NMR spectrum of W-1 in Embodiment 12.
Figure 15:
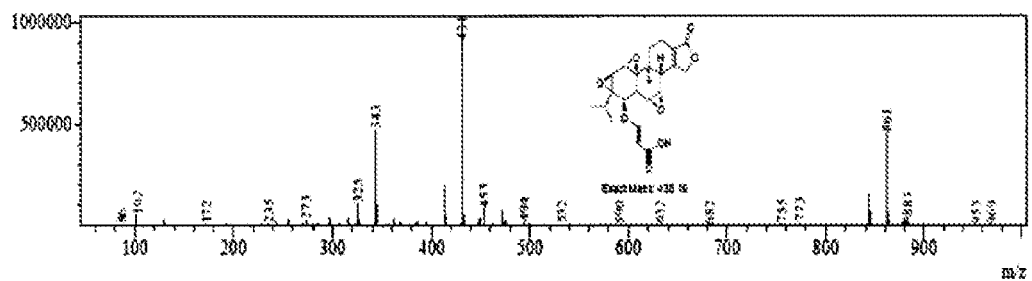
FIG. 15 is the LC-MS spectrum of W-2 in Embodiment 12.
Figure 16:
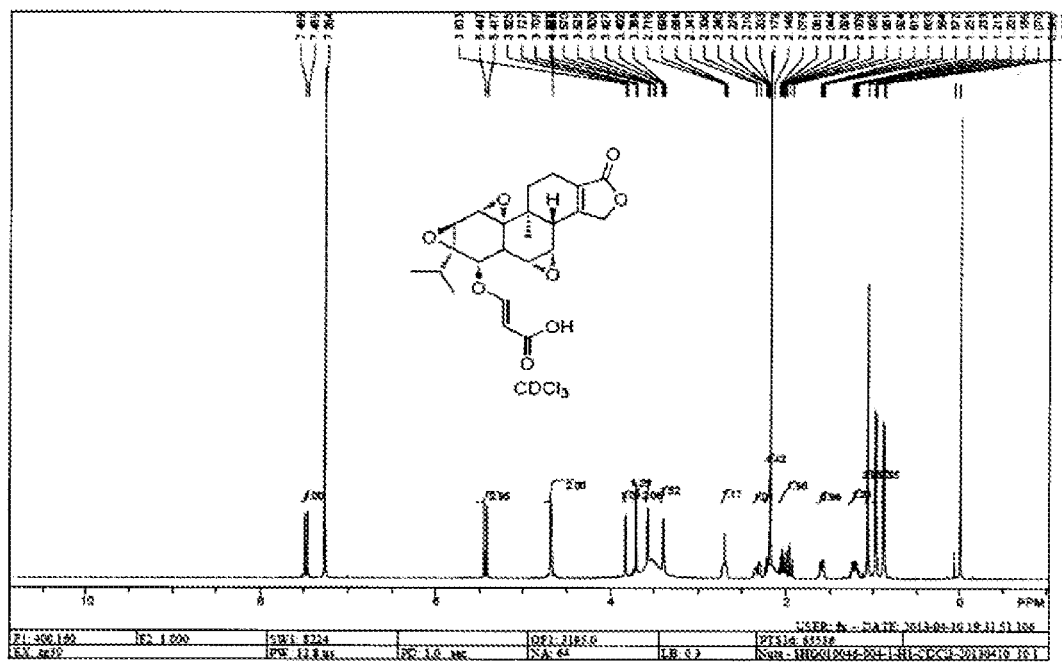
FIG. 16 is the H-NMR spectrum of W-2 in Embodiment 12.
Figure 17:
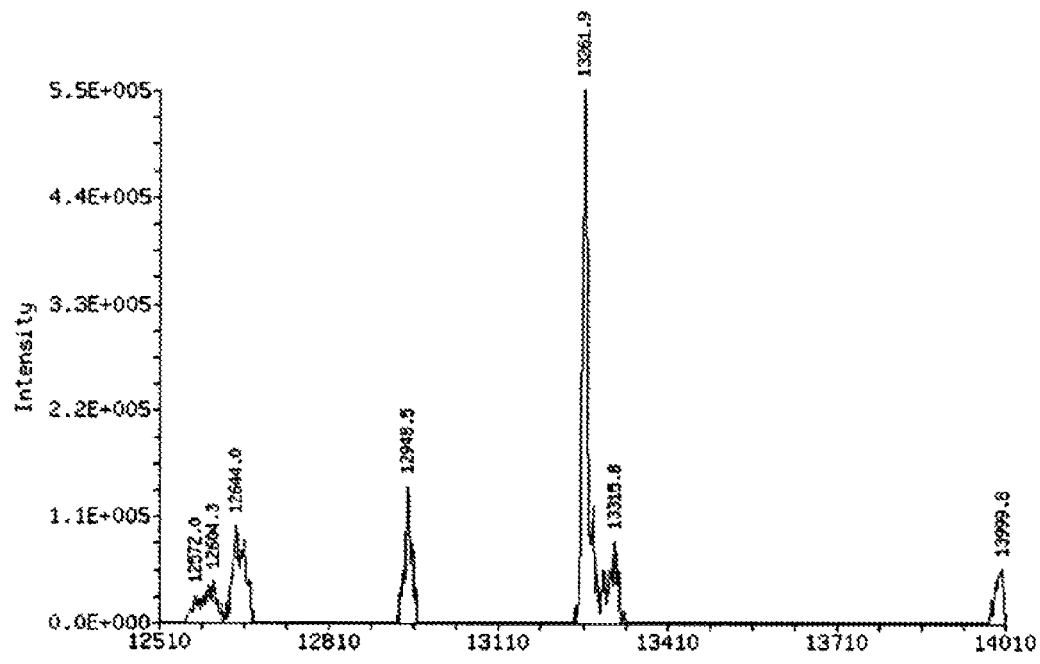
FIG. 17 is the LC-MS spectrum of W-3 (i.e. compound (22)) in Embodiment 12.

The present invention is further described by the following Embodiments or Examples, but the invention is not limited thereto.

Embodiment 1 Preparation of Compound (1)

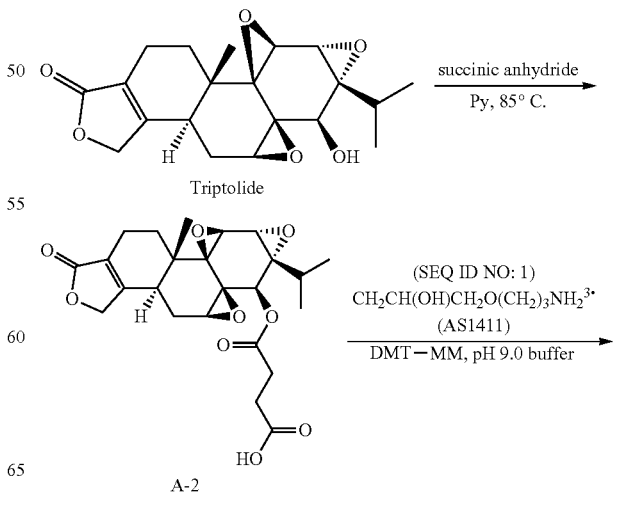

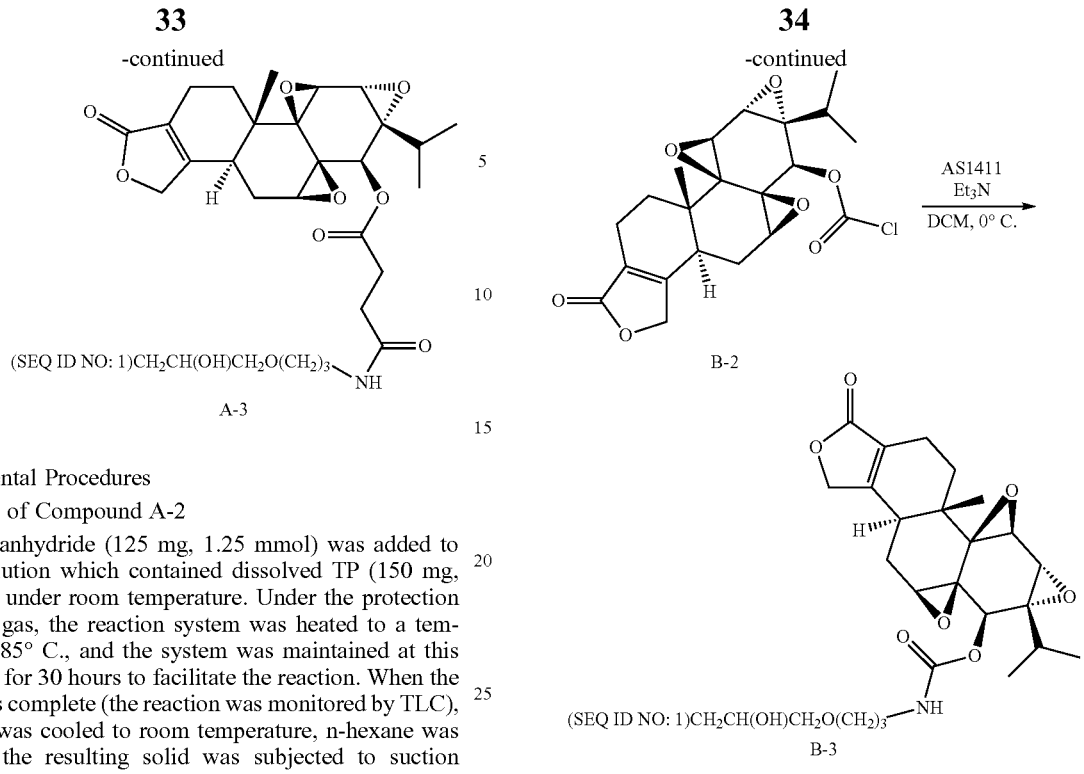

Experimental Procedures

Synthesis of Compound A-2

Succinic anhydride (125 mg, 1.25 mmol) was added to pyridine solution which contained dissolved TP (150 mg, 0.42 mmol) under room temperature. Under the protection of nitrogen gas, the reaction system was heated to a temperature of 85° C., and the system was maintained at this temperature for 30 hours to facilitate the reaction. When the reaction was complete (the reaction was monitored by TLC), the system was cooled to room temperature, n-hexane was added and the resulting solid was subjected to suction filtration and subsequently the solid product was washed by n-hexane. Finally, the crude product was re-crystallized by using n-haxane/ethyl acetate for purification such that A-2 was obtained.

LC-MS (ESI): [M+H]+: 461; [M+Na]+: 483

1H NMR (400 MHz, CDCl3) δ=5.09 (s, 1H), 4.68 (s, 2H), 3.83 (d, J=2.8 Hz, 1H), 3.53 (d, J=2.4, 1H), 3.46 (d, J=5.6 Hz, 1H), 2.72 (m, 5H), 2.31 (m, 1H), 2.14 (m, 2H), 1.89 (m, 2H), 1.56 (m, 1H), 1.22 (m, 1H), 1.05 (s, 3H), 0.95 (d, J=7.2 Hz, 3H), 0.83 (d, J=7.2 Hz, 3H).

Synthesis of Compound A-3

3 mg of AS1411 was dissolved in a buffer of sodium carbonate and sodium bicarbonate with pH=9.0, both A-2 (5.4 μmol, 150 eq.) in DMSO (54 μl) and DMT-MM (5.4 μmol, 200 eq.) in ddH$_2$O (5.4 μl) were introduced to the buffer at the same time, the reaction system was maintained at room temperature for 12 hours to facilitate the reaction. When the reaction was complete, the crude product was purified by RP HPLC, and target product A-3 was obtained.

MS: calculated 8926 (found 8926.6).

The spectrums of the corresponding starting materials and products in embodiment 1 are shown in FIGS. 1, 3-6.

Embodiment 2 Preparation of Compound (2)

Synthesis of Compound B-2

Phosgene (108 mg, 1.1 mmol) was dissolved in dichloromethane, and then TP (360 mg, 1 mmol) in dichloromethane was added dropwise to the solution at a temperature of −20° C. and in the presence of nitrogen gas. After the addition, the reaction was allowed to react at said temperature for 0.5 hr, and then increasing the temperature of the system naturally to reach the room temperature to react for 2 hr. When TLC determined that the reaction was complete, the generated hydrochloric acid gas and unreacted phosgene were removed under reduced pressure. Then, the crude product was directly used in the next step.

Synthesis of Compound B-3

AS1411 (3 mg) was dissolved in dry dichloromethane at 0° C., and triethylamine (2.02 mg, 0.02 mmol) was added to the mixture. Then B-2 (4.22 mg, 0.01 mmol) obtained from the previous step was added dropwise to a reaction flask, subsequently the temperature of the reaction system was naturally increased to the room temperature to react for 4 hours. When TLC or LC-MS determined that the reaction was complete, the resulting compound was then obtained by purification.

MS: calculated 8872 (found 8871.4).

Embodiment 3 Preparation of Compound (3)

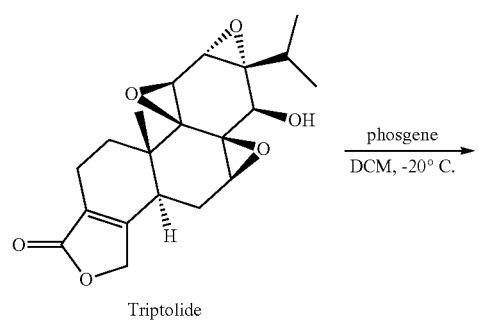

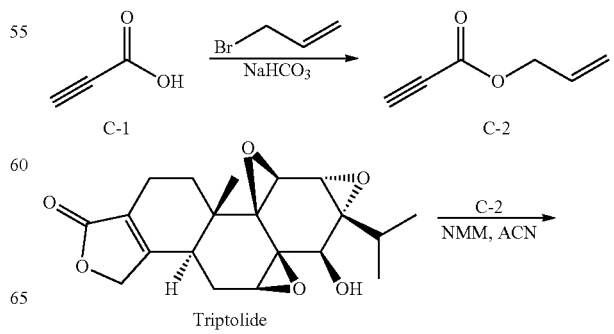

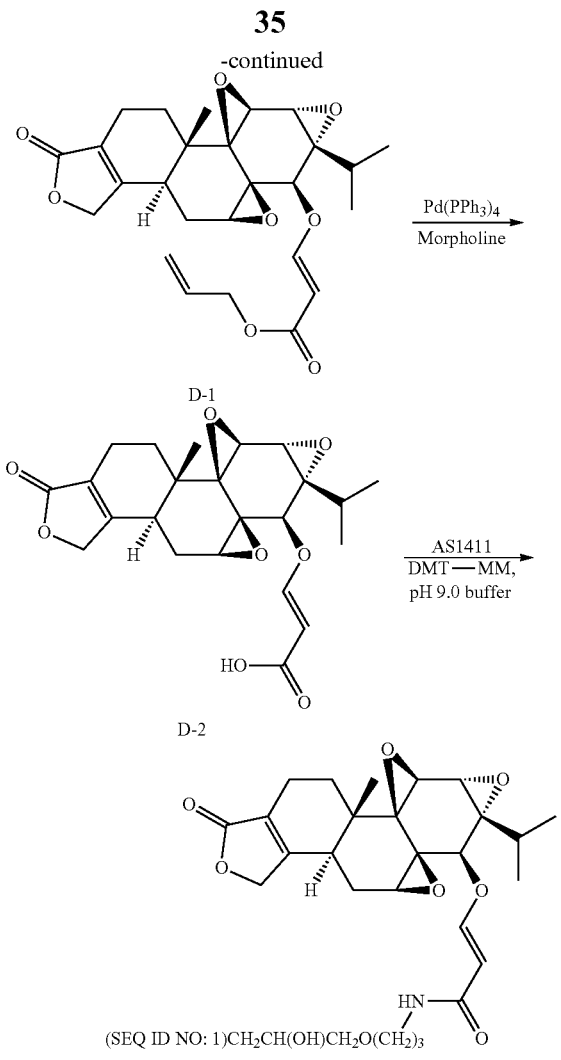

C-1 (0.91 g, 13 mmol) was dissolved in DMF, sodium bicarbonate (2.18 g, 26 mmol) was added and the mixture was stirred under room temperature for 1 hour. Allyl bromide (2.28 g, 16.9 mmol) was added and the mixture was kept at room temperature for overnight reaction. When TLC determined that the reaction was complete, EA was introduced to the reaction system, and then water was used to perform extraction for several times. Finally the organic phase was dried by anhydrous sodium sulfate, filtered, and subjected to evaporation, and then C-2 crude was obtained.

Synthesis of Compound D-1

TP (50 mg, 139 mol) and C-2 (23 mg, 208 mol) were dissolved in acentonitrile, and then NMM (15 µl, 0.5 eq.) was added to the mixture. This reaction system was maintained at room temperature for 12 hours to facilitate the reaction. After TLC determined that the reaction was complete, the organic solvent was removed under reduced pressure, and the crude product was subjected to a quick silica gel column chromatography so as to obtain the pure product D-1.

LC-MS (ESI): [M+H]+: 471; [M+Na]+: 493

1H NMR (400 MHz, CDCl₃) δ=7.41 (d, J=12.4 Hz, 1H), 5.91-5.98 (m, 1H), 5.47 (d, J=12.4 Hz, 1H), 5.31 (dd, J=1.2, 17.4 Hz, 1H), 5.22 (dd, J=1.2, 10.4 Hz, 1H), 4.68 (s, 2H), 4.61 (d, J=3.6 Hz, 2H), 3.82 (d, J=3.2 Hz, 1H), 3.69 (s, 1H), 3.60 (d, J=2.8 Hz, 1H), 3.38 (d, J=5.6 Hz, 1H), 2.70 (m, 1H), 2.30 (m, 1H), 2.16-2.22 (m, 1H), 1.92-2.06 (m, 2H), 1.57-1.61 (m, 3H), 1.17-1.25 (m, 3H), 1.07 (s, 3H), 0.97 (d, J=7.2 Hz, 3H), 0.87 (d, J=6.8 Hz, 3H).

Synthesis of Compound D-2

D-1 (15 g, 0.5 eq.) was dissolved in tetrahydrofuran, morpholine (50 µl, 10 equiv.) and tetrakis-(triphenylphosphine)-palladium (14 mg, 0.15 equiv.) were added to the mixture, the reaction was performed under room temperature. The reaction was monitored by LC-MS until D-1 has been completely consumed. Subsequently, the organic solvent was removed under reduced pressure, the crude product was subjected to column chromatography for purification, and the pure product D-2 was obtained.

LC-MS (ESI): [M+H]+: 431

1H NMR (400 MHz, CDCl₃) δ=7.47 (d, J=12.0 Hz, 1H), 5.42 (d, J=12.0 Hz, 1H), 4.68 (s, 2H), 3.83 (d, J=3.2 Hz, 1H), 3.71 (s, 1H), 3.57 (d, J=2.8 Hz, 1H), 3.39 (d, J=5.39 Hz, 1H), 2.68-2.72 (m, 1H), 2.31-2.35 (m, 1H), 2.18-2.23 (m, 4H), 1.93-2.06 (m, 2H), 1.60 (dd, J=4.8, 12.4 Hz, 1H), 1.20-1.25 (m, 3H), 1.07 (s, 3H), 0.97 (d, J=7.2 Hz, 3H), 0.88 (d, J=6.8 Hz, 3H).

Synthesis of Compound D-3

AS1411 (20 nmol) was dissolved in a buffer of sodium carbonate and sodium bicarbonate (200 µL, pH 9.0) with pH=9.0, both D-2 (5 mg, 1200 nmol) in DMSO (200 µl) and DMT-MM (200 nmol) in ddH₂O (200 µl) were added at the same time to the buffer. The reaction system was maintained at room temperature for 12 hours to facilitate the reaction. After the reaction was complete, the crude product was subjected to RP HPLC for purification, and target product D-3 was obtained.

MS: calculated 8896 (found 8895.9).

The spectrums of the corresponding starting materials and products in embodiment 3 are shown in FIGS. 7-12.

Embodiment 4 Preparation of Compound (4)

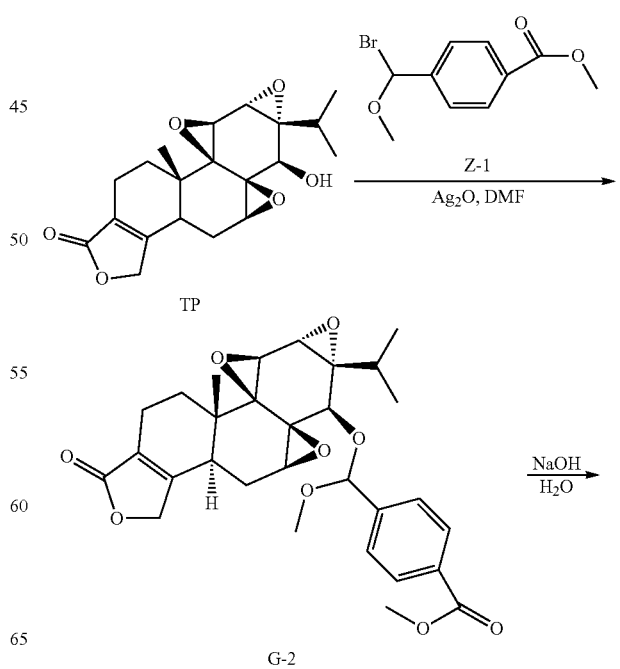

Embodiment 5 Preparation of Compound (5)

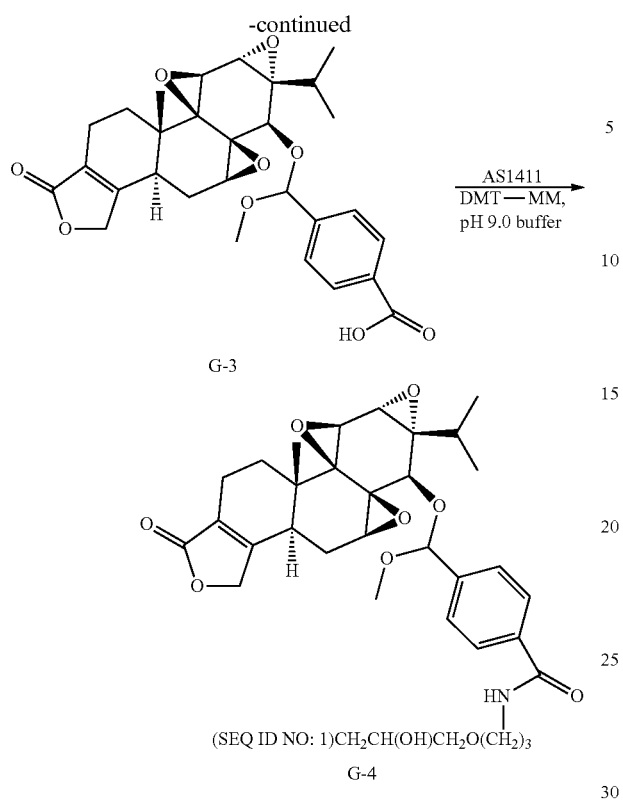

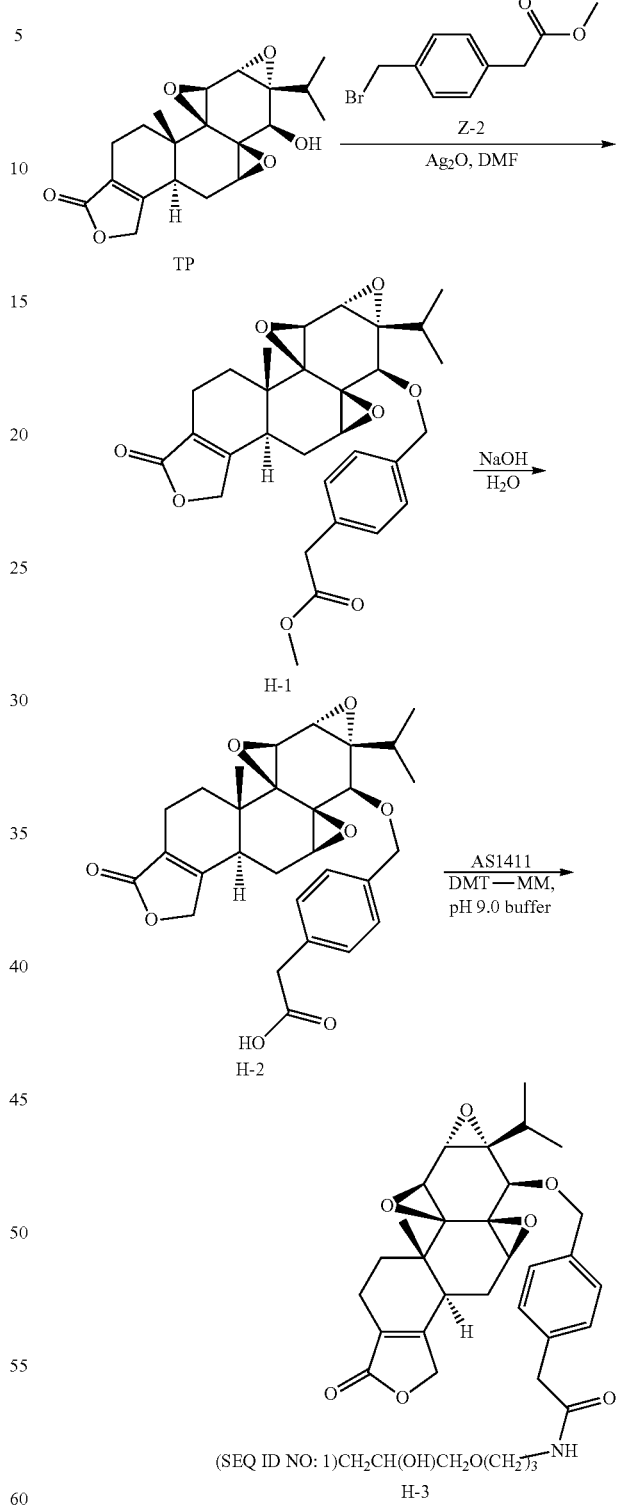

Synthesis of Compound G-2

TP (360 mg, 1 mmol) was dissolved in DMF at a temperature of 0° C. and in the presence of nitrogen gas, Z-1 (680 mg, 2.5 mmol) and silver oxide (458 mg, 2 mmol) were then added. The temperature of the reaction system was naturally increased to room temperature, and the system was maintained at this temperature for 24 hours to facilitate the reaction. When TLC determined that the reaction was complete, water was added, ethyl acetate was used for extraction and then the organic phases were combined together and washed by saturated saline, subsequently dried by anhydrous sodium sulfate, filtered, and condensed. The crude product was thus obtained.

Synthesis of Compound G-3

G-2 (552 mg, 1 mmol) was dissolved in DCM at 0° C., sodium hydroxide aqueous solution (80 mg, 2 mmol) was added. The reaction system was maintained at said temperature for reaction. When TLC determined that the reaction was complete, dichloromethane was applied for extraction and the organic phase was washed by saturated saline, dried by anhydrous sodium sulfate, filtered and subjected to evaporation. G-3 crude product was thus obtained.

Synthesis of Compound G-4

AS1411 (20 nmol) was dissolved in a buffer of sodium carbonate and sodium bicarbonate (200 L, pH 9.0) with pH=9.0, both G-3 (5 mg, 1000 nmol) in DMSO (200 μl) and DMT-MM (200 nmol) in $H_2O$ (200 μl) were added to the buffer at the same time. The reaction system was maintained at room temperature for 12 hours to facilitate the reaction. After the reaction was complete, the crude product was subjected to RP HPLC for purification, and target product G-4 was thus obtained.

MS: calculated 8992 (found 8992.6).

Synthesis of Compound H-2

TP (360 mg, 1 mmol) was dissolved in DMF at 0° C. and in the presence of to room temperature, and the system was remained at this temperature for 24 hours to facilitate the reaction. When TLC determined that the reaction was complete, water was added and ethyl acetate was applied for extraction. The organic phases were combined together, washed by saturated saline, dried by anhydrous sodium sulfate, filtered, and condensed. The crude product was thus obtained.

Synthesis of Compound H-2

H-1 (552 mg, 1 mmol) was dissolved in DCM at 0° C., sodium hydroxide aqueous solution (80 mg, 2 mmol) was then added. The system was maintained at said temperature for reaction. When TLC determined that the reaction was complete, dichloromethane was applied for extraction, the organic phase was washed by saturated saline, dried by anhydrous sodium sulfate, filtered, and subjected to evaporation. H-2 crude product was then obtained.

Synthesis of Compound H-3

AS1411 (20 nmol) was dissolved in a buffer of sodium carbonate and sodium bicarbonate (200 μL, pH 9.0) with pH=9.0, both H-2 (5 mg, 950 nmol) in DMSO (200 μl) and DMT-MM (200 nmol) in $H_2O$ (200 μl) were added to the buffer at the same time. The reaction system was maintained at room temperature for 12 hours to facilitate the reaction. After the reaction was complete, the crude product was subjected to RP HPLC for purification, and target product H-3 was then obtained.

MS: calculated 8918 (found 8919.2).

Embodiment 6 Preparation of Compound (6)

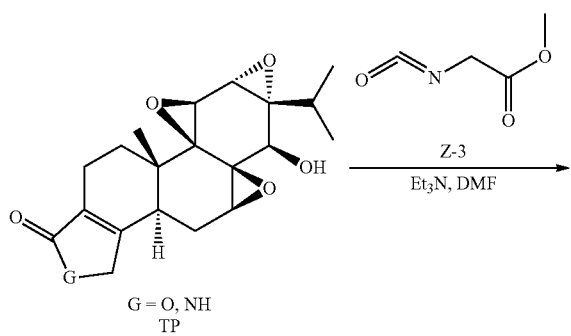

G = O, NH
TP

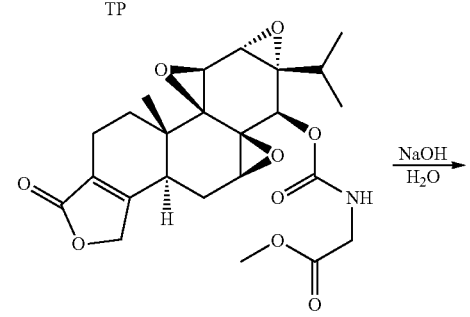

K-2

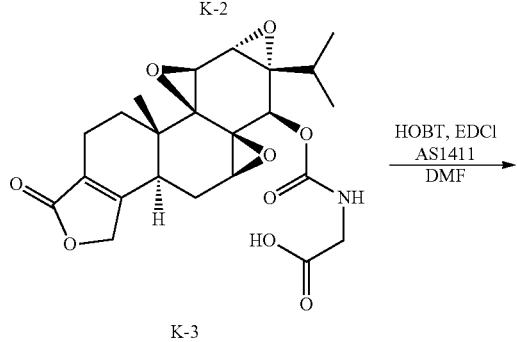

K-3

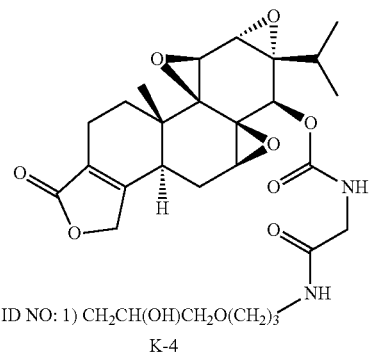

(SEQ ID NO: 1) $CH_2CH(OH)CH_2O(CH_2)_3$
K-4

Synthesis of Compound K-2

TP (360 mg, 1 mmol) and triethylamine (120 mg, 1.1 mmol) were dissolved in dichloromethane, Z-3 (126 mg, 1.1 mmol) was then added to the mixture. The reaction system was maintained at room temperature for 12 hours to facilitate the reaction. When TLC determined that the reaction was complete, the organic solvent was removed under reduced pressure, and the crude product was subjected to a quick silica gel column chromatography so as to obtain a pure product K-2.

Synthesis of Compound K-3

K-2 (475 mg, 1 mmol) was dissolved in DCM at 0° C., sodium hydroxide solution (80 mg, 2 mmol) was added to the mixture. The system was maintained at said temperature for reaction. When TLC determined that the reaction was complete, dichloromethane was used for extraction, the organic phase was washed by saturated saline, dried by anhydrous sodium sulfate, filtered and subjected to evaporation, and then K-3 crude product was obtained.

Synthesis of Compound K-4

K-3 (461 mg, 1 mmol) obtained from the previous step was dissolved in DCM at room temperature, HOBT (148 mg, 1.1 mmol) and EDCI (210 mg, 1.1 mmol) were added to the mixture. After reacting at room temperature for 0.5 hours, AS1411 (20 nmol) was introduced to the mixture, and proceeded with the reaction at said temperature for 3 hours. When TLC or LC-MS determined that the reaction was complete, the compound K-4 was then obtained after purification.

MS: calculated 8929 (found 8929.8).

Embodiment 7 Preparation of Compound (7)

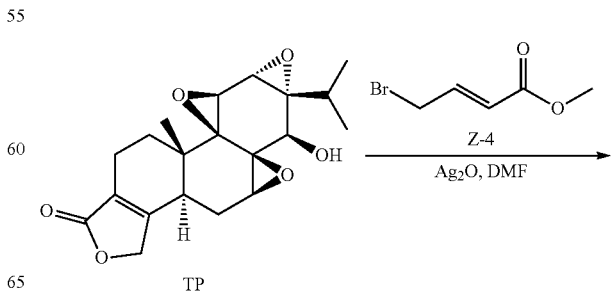

TP

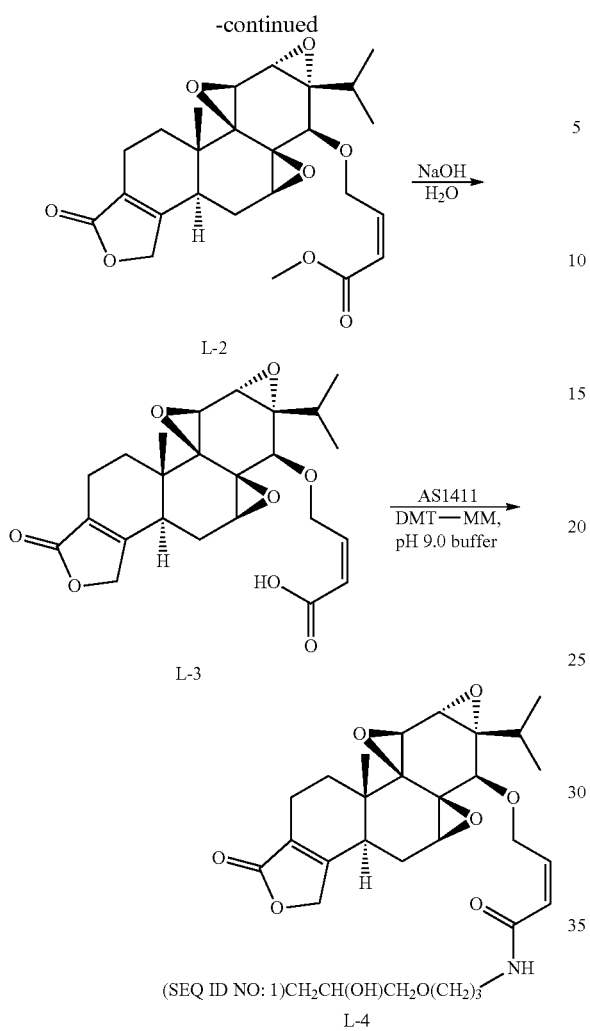

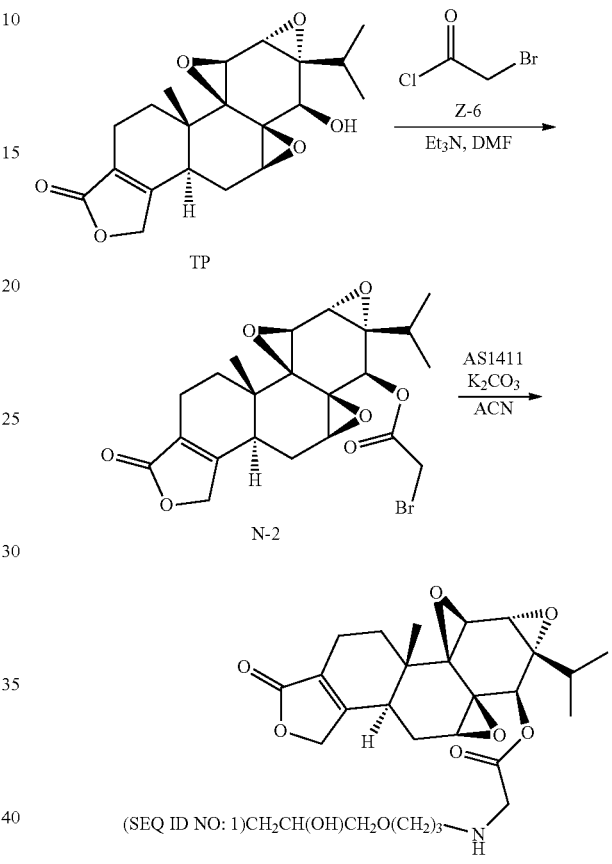

at room temperature for 12 hours to facilitate the reaction. After the reaction was complete, the crude product was subjected to RP HPLC for purification, and then target product L-4 was obtained.

MS: calculated 8912 (found 8913.2).

Embodiment 8 Preparation of Compound (8)

Synthesis of Compound L-2

TP (360 mg, 1 mmol) was dissolved in DMF at 0° C. and in the presence of nitrogen gas, Z-4 (442 mg, 2.5 mmol) and silver oxide (458 mg, 2 mmol) were then added. The temperature of the reaction system was naturally increased to room temperature, and the system was maintained at this temperature for 24 hours to facilitate the reaction. When TLC determined that the reaction was complete, water was added, ethyl acetate was applied for extraction and the organic phases were combined together, washed by saturated saline, dried by anhydrous sodium sulfate, filtered, and condensed, and then crude product was obtained.

Synthesis of Compound L-3

L-2 (458 mg, 1 mmol) was dissolved in DCM at 0° C., sodium hydroxide solution (80 mg, 2 mmol) was then added. The system was maintained at said temperature for reaction. When TLC determined that the reaction was complete, dichloromethane was used for extraction, the organic phase was washed by saturated saline, dried by anhydrous sodium sulfate, filtered, and subjected to evaporation, and then L-3 crude was obtained.

Synthesis of Compound L-4

AS1411 (20 nmol) was dissolved in a buffer of sodium carbonate and sodium bicarbonate (200 μL, pH 9.0) with pH=9.0, both L-3 (5 mg, 1120 nmol) in DMSO (200 μl) and DMT-MM (200 nmol) in $H_2O$ (200 μl) were added to the buffer at the same time. The reaction system was maintained Synthesis of Compound N-2

TP (360 mg, 1 mmol) and triethylamine (151 mg, 1.5 mmol) were dissolved in dichloromethane at 0° C. and nitrogen, Z-4 (177 mg, 1.1 mmol) was then added. The temperature of the reaction system was increased to room temperature for reacting. When TLC determined that the reaction was complete, the organic solvent was removed under reduced pressure, and crude product was subjected to a quick silica gel column chromatography for purification, and then a pure product N-2 was obtained.

Synthesis of Compound N-3

N-2 (480 mg, 1 mmol) was dissolved in acetonitrile, potassium carbonate (129 mg, 1.2 mmol) was added to the mixture, and subsequently AS1411 (20 nmol) was added under the protection of nitrogen. The temperature of the reaction system was increased to 50° C. to facilitate the reaction for 4 hours. After the TLC or LC-MS determined that the reaction was complete, N-3 was obtained through purification.

MS: calculated 8886 (found 8887.4).

Embodiment 9 Preparation of Compound (9)

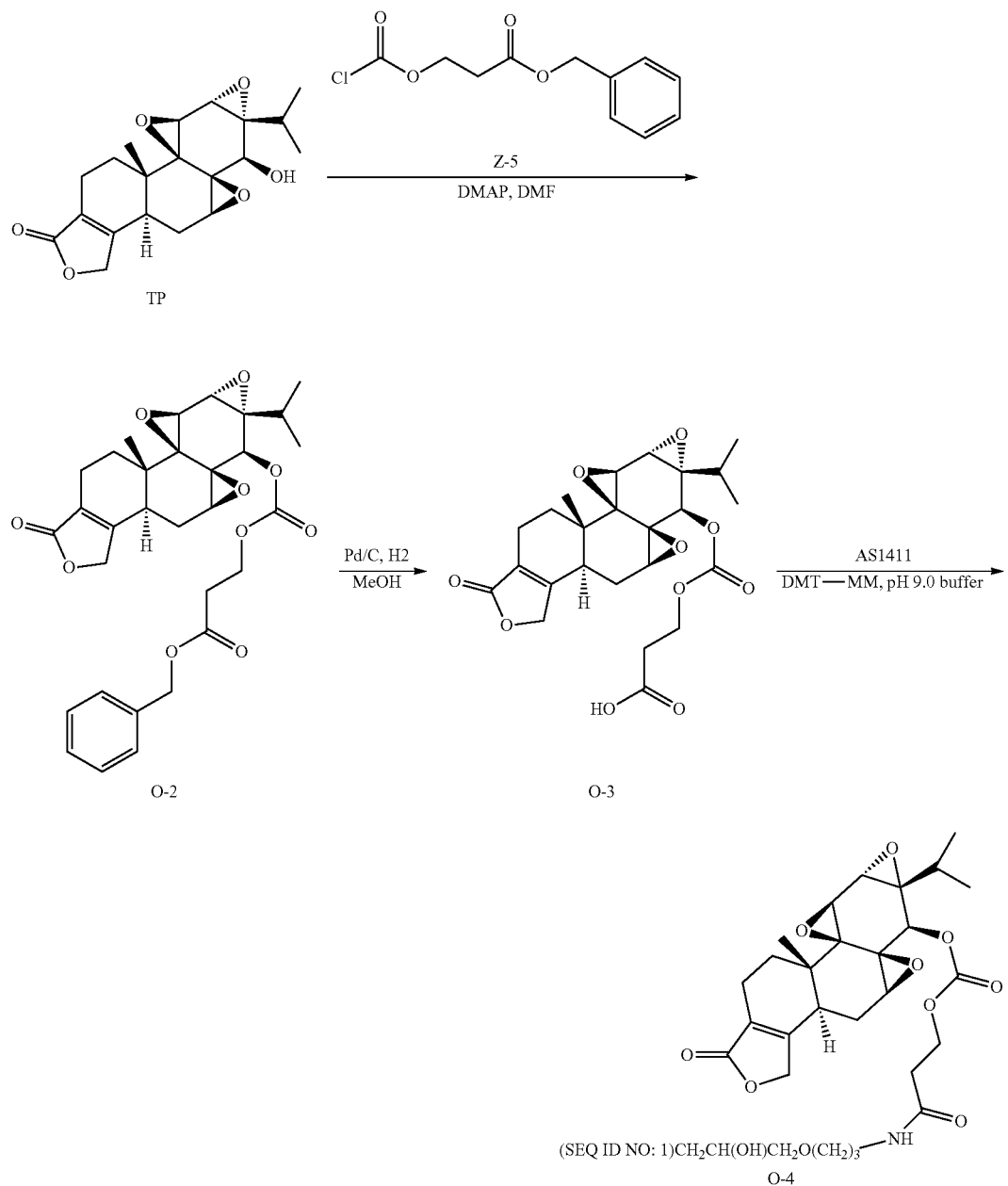

Synthesis of Compound O-2

TP (360 mg, 1 mmol) and N,N-dimethyl pyridine (146 mg, 1.2 mmol) were dissolved in DMF at 0° C. and in the presence of nitrogen gas, Z-5 (266 mg, 1.1 eq) was then added to the mixture. The temperature of the reaction system was increased to room temperature for reacting. When TLC determined that the reaction was complete, the organic solvent was removed under reduced pressure, and the crude product was subjected to a quick silica gel column chromatography for purification and then a pure product O-2 was obtained.

Synthesis of Compound O-3

O-2 (566 mg, 1 mmol) was dissolved in methanol, 50 mg of 10% Pd/C was added to the solution. After the atmosphere was replaced by hydrogen, the reaction was performed at room temperature. When TLC determined the reaction was complete, a suction filtration was carried out and the organic solvent was evaporated so as to obtain the crude product. Further, a suitable purification method was selected to obtain O-3.

Synthesis of compound O-4: AS1411 (20 nmol) was dissolved in a buffer of sodium carbonate and sodium bicarbonate (200 L, pH 9.0) with pH=9.0, both O-2 (5 mg, 1050 nmol) in DMSO (200 μl) and DMT-MM (200 nmol) in $H_2O$ (200 μl) were added to the buffer at the same time. The reaction system was maintained at room temperature for 12 hours to facilitate the reaction. After the reaction was complete, the crude product was subjected to RP HPLC for purification, and then target product O-3 was obtained.

MS: calculated 8946 (found 8947.2).

Embodiment 10 Preparation of Compound (50)
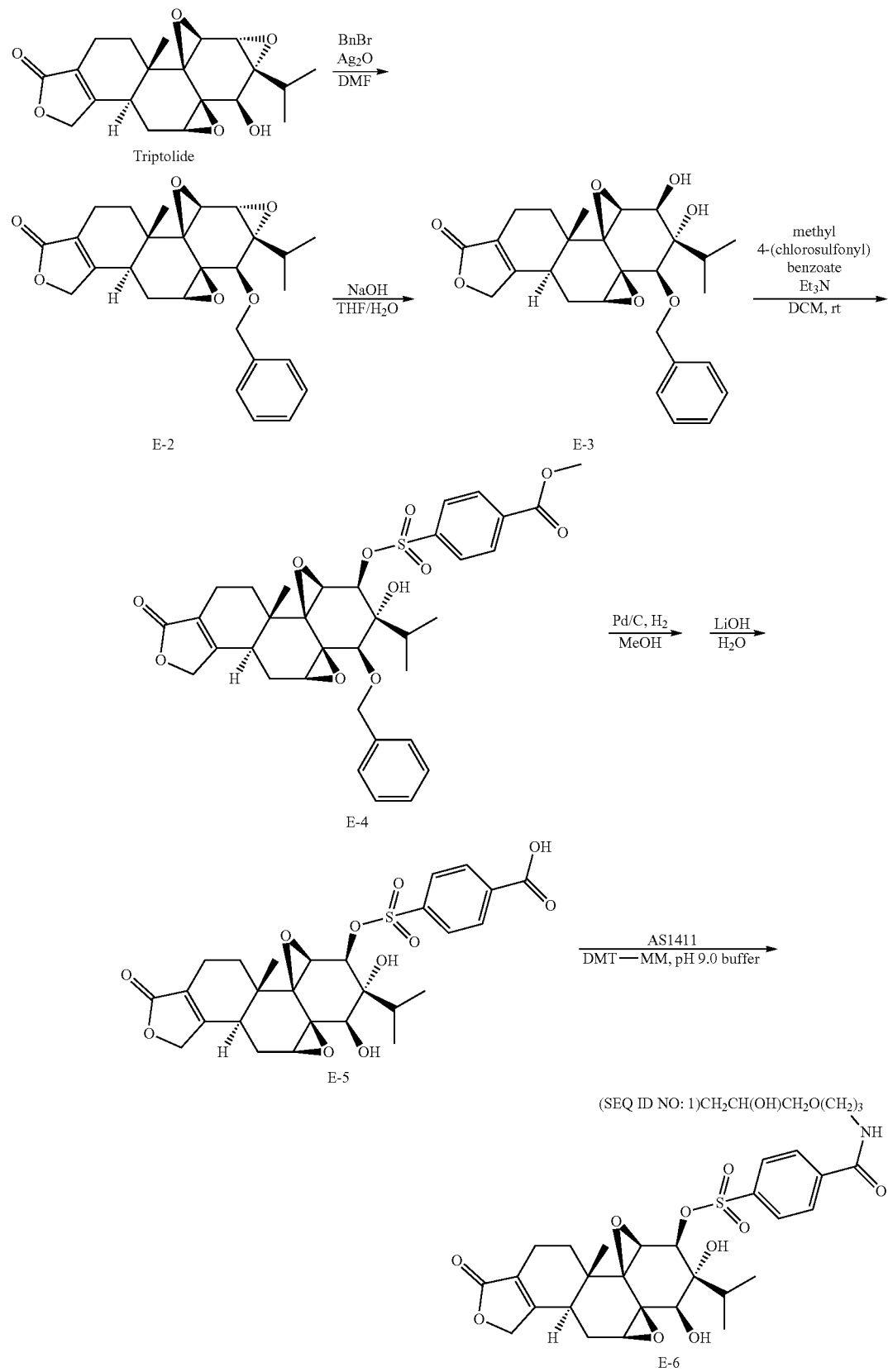

Synthesis of Compound E-2

TP (360 mg, 1 mmol) was dissolved in DMF at 0° C. and in the presence of nitrogen gas, benzyl bromide (422 mg, 2.5 mmol) and silver oxide (458 mg, 2 mmol) were added to the solution. The temperature of the reaction system was naturally increased to room temperature, and the system was maintained at this temperature for 24 hours to facilitate the reaction. When TLC determined that the reaction was complete, water was added, and ethyl acetate was used for extraction. The organic phases were combined together, washed by saturated saline, dried by anhydrous sodium sulfate, filtered, and condensed so as to obtain the crude product.

Synthesis of Compound E-3

E-2 (450 mg, 1 mmol) was dissolved in THF, sodium hydroxide solution (120 mg, 3 mmol) was added to the solution. the temperature of the reaction system was increased to 75° C. for reaction. When TLC determined that the reaction was complete, the reaction system was then cooled to room temperature. THF was removed by elevated pressure. Dichloromethane was used to carried out the extraction, the organic phase ass washed by saturated saline, dried by anhydrous sodium sulfate, filtered, and subjected to evaporation so as to obtain E-3 crude product.

Synthesis of Compound E-4

E-3 (468 mg, 1 mmol) was dissolved in dichloromethane, triethylamine (151 mg, 1.5 mmol) was then added to the solution. Methoxycarbonyl benzenesulfonyl chloride (280 mg, 1.2 mmol) in dichloromethane was slowly added dropwise to the solution at 0° C. After the addition, the temperature of the reaction system was naturally increased to room temperature. The reaction was monitored by TLC, when the reaction was complete, the organic phase was washed by water and saturated saline respectively, dried by anhydrous sodium sulfate, filtered, and subjected to evaporation so as to obtain E-4 crude product.

Synthesis of Compound E-5

E-4 (666 mg, 1 mmol) was dissolved in THF, 50 mg of 10% Pd/C was added to the solution. The atmosphere was replaced by hydrogen. The reaction was carried out under room temperature for 5 hours. The reaction was monitored by TLC. After the reaction was complete, Pd/C was removed by suction filtration, and the next step was directly performed. 1 mmole of the resulting product of the above steps was dissolved in DCM at 0° C., lithium hydroxide (38 mg, 2 mmol) aqueous solution was added. The reaction was maintained to react at said temperature. When TLC determined that the reaction was complete, dichloromethane was used for extraction and the organic phase was washed by saturated saline, dried by anhydrous sodium sulfate, filtered and subjected to evaporation so as to obtain E-5 crude product.

Synthesis of Compound E-6

AS1411 (3 mg) was dissolved in a buffer of sodium carbonate and sodium bicarbonate with pH=9.0, both E-5 (5.4 µmol, 150 eq.) in DMSO (54 µl) and DMT-MM (5.4 µmol, 200 eq.) in ddH$_2$O (54 µL) were introduced to the buffer at the same time. The reaction system was maintained at room temperature for 12 hours to facilitate the reaction. After the reaction was complete, the crude product was subjected to RP HPLC for purification so as to obtain target product E-6.

MS: calculated 9012 (found 9012.4).

Embodiment 11 Preparation of Compound (64)

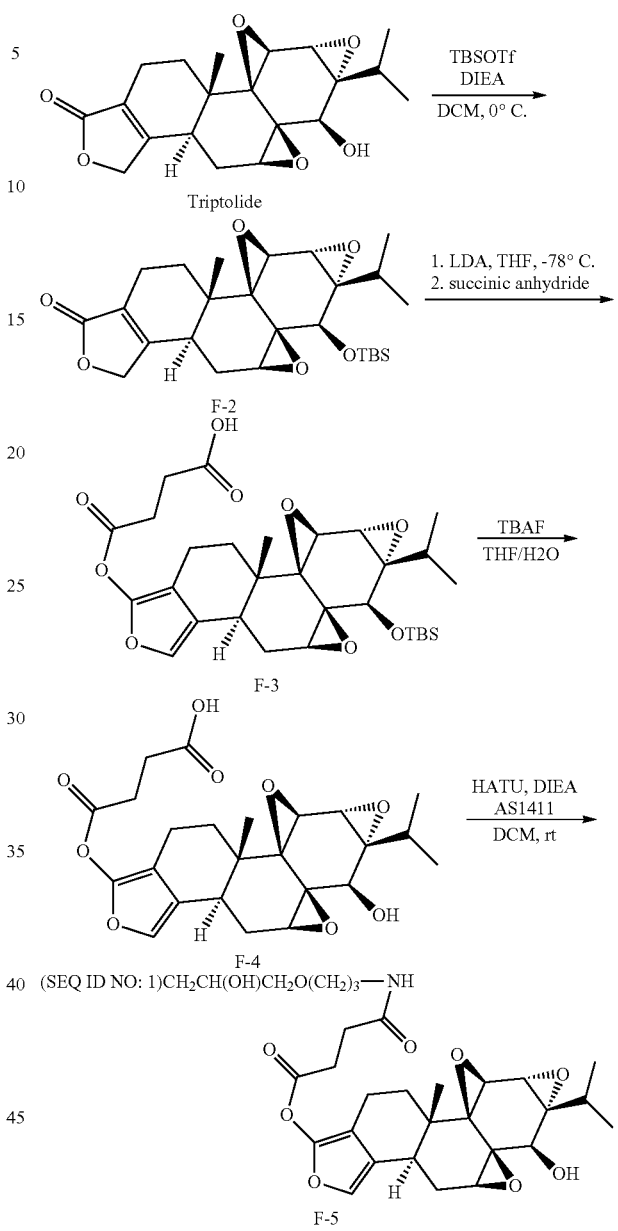

Synthesis of Compound F-2

TP (360 mg, 1 mmol) was dissolved in dichloromethane at 0° C., DIFA (195 mg, 1.5 mmol) was then added to the solution. Tert-butyldimethylsilyl triflate (TBSOTf) (317 mg, 1.2 mmol) diluted by dichloromethane was slowly added dropwise to the solution. The reaction was maintained at said temperature for 0.5 hours and then the temperature of the system was increased to room temperature for further reaction for 4 hours. After TLC determined that the reaction was complete, the reaction solution was introduced to a saturated sodium bicarbonate, extracted the mixture with dichloromethane, the resulting product was washed by saturated saline, dried by anhydrous sodium sulfate, filtered, and subjected to evaporation so as to obtain F-2 crude product.

Synthesis of Compound F-3

F-2 (474 mg, 1 mmol) was dissolved in tetrahydrofuran, an slightly excess amount of LDA was slowly added to the solution at −78° C. under the protection of nitrogen gas. The reaction was maintained at said temperature for 1 hour. Succinic anhydride (100 mg, 1 mmol) was added and then the temperature of the reaction system was naturally increased to room temperature to react for 2 hours. After TLC determined that the reaction was complete, a saturated ammonium chloride solution was added, then, the resulting solution was condensed to remove tetrahydrofuran through evaporation. Dichloromethane was applied for extraction, the resulting compound was washed by saturated saline, dried by anhydrous sodium sulfate, filtered, and subjected to evaporation so as to obtain F-3 crude product.

Synthesis of Compound F-4

F-3 (574 mg, 1 mmol) was dissolved in a mixture solution of anhydrous tetrahydrofuran and water, tetrabutylammonium fluoride (313 mg, 1.2 mmol) was added to the mixture under room temperature. After stirring the mixture under room temperature for 3 hours, is the resulting solution was condensed and extracted with dichloromethane, washed by saturated saline, dried by anhydrous sodium sulfate, filtered, and subjected to evaporation so as to obtain F-4 crude product.

Synthesis of Compound F-5

F-4 (460 mg, 1 mmol) obtained from the previous steps was dissolved in dichloromethane under room temperature, then HATU (148 mg, 1.1 mmol) and DIEA (210 mg, 1.1 mmol) were introduced to the mixture. The reaction was performed under room temperature for 0.5 hours, AS1411 (20 nmol) was introduced and the reaction was maintained at said temperature for 3 hours. After TLC or LC-MS determined that the reaction was complete, the F-5 compound was then obtained.

MS: calculated 8926 (found 8927.2).

Embodiment 12 Preparation of Compound (22)

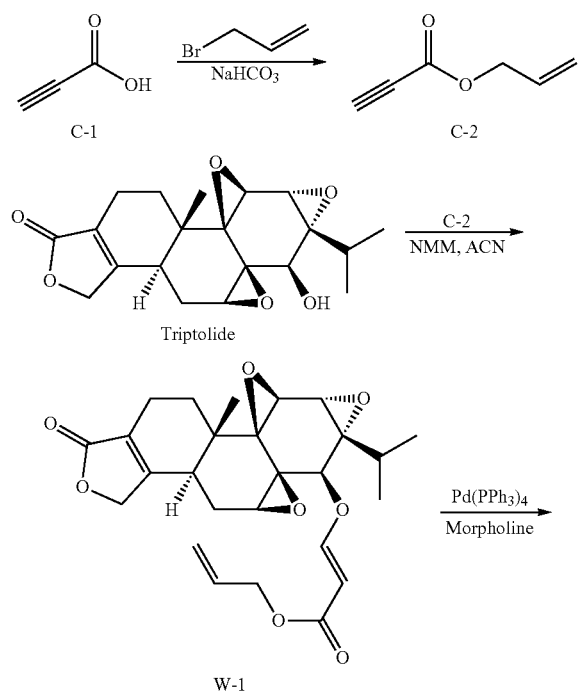

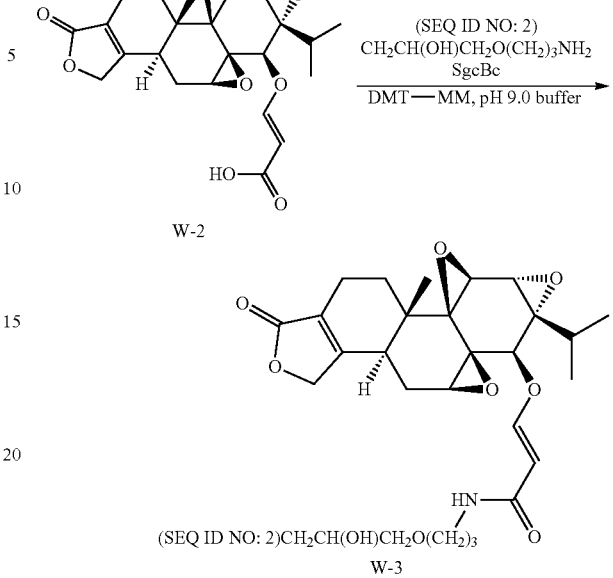

C-1 (0.91 g, 13 mmol) was dissolved in DMF, sodium bicarbonate (2.18 g, 26 mmol) was added to the solution. After stirring the mixture under room temperature for 1 hour, allyl bromide (2.28 g, 16.9 mmol) was added. The reaction was maintained under room temperature for overnight reaction. After TLC determined that the reaction was complete, EA was added to the reaction system. Water was used to perform extraction for several times, and finally the organic phase was dried by anhydrous sodium sulfate, filtered, and subjected to evaporation so as to obtain C-2 crude product.

Synthesis of Compound W-1

TP (50 mg, 139 μmol) and C-2 (23 mg, 208 μmol) were dissolved in acetonitrile, then NMM (15 μl, 0.5 eq.) was added. The reaction system was maintained under room temperature for 12 hours to facilitate the reaction. After TLC determined that the reaction was complete, the organic solvent was removed under reduced pressure, and the crude product was subjected to a quick silica gel column chromatography for purification so as to obtain a pure product W-1.

LC-MS (ESI): [M+H]+: 471; [M+Na]+: 493

1HNMR (400 MHz, CDCl3) δ=7.41 (d, J=12.4 Hz, 1H), 5.91-5.98 (m, 1H), 5.47 (d, J=12.4 Hz, 1H), 5.31 (dd, J=1.2, 17.4 Hz, 1H), 5.22 (dd, J=1.2, 10.4 Hz, 1H), 4.68 (s, 2H), 4.61 (d, J=3.6 Hz, 2H), 3.82 (d, J=3.2 Hz, 1H), 3.69 (s, 1H), 3.60 (d, J=2.8 Hz, 1H), 3.38 (d, J=5.6 Hz, 1H), 2.70 (m, 1H), 2.30 (m, 1H), 2.16-2.22 (m, 1H), 1.92-2.06 (m, 2H), 1.57-1.61 (m, 3H), 1.17-1.25 (m, 3H), 1.07 (s, 3H), 0.97 (d, J=7.2 Hz, 3H), 0.87 (d, J=6.8 Hz, 3H).

Synthesis of Compound W-2

W-1 (15 μl, 0.5 eq.) was dissolved in tetrahydrofuran, morpholine (50 μl, 10 equiv.) and tetrakis(triphenylphosphine)-palladium (14 mg, 0.15 equiv.) were added to the solution. The reaction was carried out under room temperature. The reaction was monitored by LC-MS until all W-1 had been completely consumed. After the removal of the organic solvent under reduced pressure, the crude product was subjected to column chromatography for purification so as to obtain the pure product W-2.

LC-MS (ESI): [M+H]+: 431

1H NMR (400 MHz, CDCl3) δ=7.47 (d, J=12.0 Hz, 1H), 5.42 (d, J=12.0 Hz, 1H), 4.68 (s, 2H), 3.83 (d, J=3.2 Hz, 1H), 3.71 (s, 1H), 3.57 (d, J=2.8 Hz, 1H), 3.39 (d, J=5.39 Hz, 1H), 2.68-2.72 (m, 1H), 2.31-2.35 (m, 1H), 2.18-2.23 (m, 4H), 1.93-2.06 (m, 2H), 1.60 (dd, J=4.8, 12.4 Hz, 1H), 1.20-1.25 (m, 3H), 1.07 (s, 3H), 0.97 (d, J=7.2 Hz, 3H), 0.88 (d, J=6.8 Hz, 3H).

Synthesis of Compound W-3

Sgc8c (20 nmol) was dissolved in a buffer of sodium carbonate and sodium bicarbonate (200 μL, pH 9.0) with pH=9.0, both D-2 (5 mg, 1200 nmol) in DMSO (200 μl) and DMT-MM (200 nmol) in $H_2O$ (200 μl) were added to the buffer at the same time. The reaction system was maintained at room temperature for 12 hours to facilitate the reaction. After the reaction was complete, the crude product was subjected to RP HPLC for purification so as to obtain target product W-3.

MS: calculated 13263 (found 13261.9).

The spectrums of the corresponding starting materials and products in embodiment 12 are shown in FIGS. 2, 13-17.

EXAMPLE 1

Inhibition of Triptolide-AS1411 Conjugate on the Growth of Cancer Cells In Vitro 1. Experimental Materials:

Chemicals:

Triptolide (TP), source: commercially available;

AS1411 (also named as "nucleolin aptamer"), source: commercially available;

Triptolide-AS1411 conjugate (also named as "chemical 1"), source: compound (3) prepared in Embodiment 3.

Cell culture medium (DMEM, McCoy's, RPMI-1640, Leibovitz'sL-05) was purchased from GIBCO, and fetal bovine serum was purchased from Hyclone.

CCK-8 used for detecting cell activities was purchased from Sigma.

5 pancreatic cancer cell lines (MiaPaCa-2, PANC-1, BxPC-3, SW1990 and ASPC-1) used in the experiments were all purchased from Shanghai Cell Bank.

2. Experimental Methods:

1) Cell Culture:

The culture medium of MiaPaCa-2 and PANC-1 was DMEM, the culture medium of BxPC-3 and ASPC-1 was RPMI-1640, and the culture medium of SW1990 was L-05. Fetal bovine serum and two antibiotics were added into the above media so as to form a final culture medium with a final content of 10% and 1%. Cells were incubated in an incubator at 37° C. and with 5% $CO_2$.

2) Study on Anti-Cancer Activity:

Pancreatic cancer cells (MiaPaCa-2, PANC-1, BxPC-3, SW1990 and ASPC-1) were uniformly seeded into a 96-well plate with a low density ($1 \times 10^3 \sim 1 \times 10^4$, depending on the specific cell lines, and the conditions were referred to Shanghai Cell Bank). After placed in incubator for adhering overnight, the used medium was replaced by a serum free medium containing drug. Triptolide was dissolved in DMSO to prepare a stock solution with 10 nM, the triptolide-nucleolin aptamer conjugate and the nucleolin aptamer were both dissolved in the serum free medium containing drug so as to form a solution with 10 mM, and these solutions were used right after preparation. The serum free medium containing drug was used as the blank reference, the concentration gradient of triptolide, triptolide-nucleolin aptamer conjugate and nucleolin aptamer used in treatments were: 0, 25, 50, 100 and 200 nM. The cells were then incubated in the incubator at 37° C. and with 5% $CO_2$. Cell activities were measured by MTT. The operation was performed for 4 times.

Figure 18:
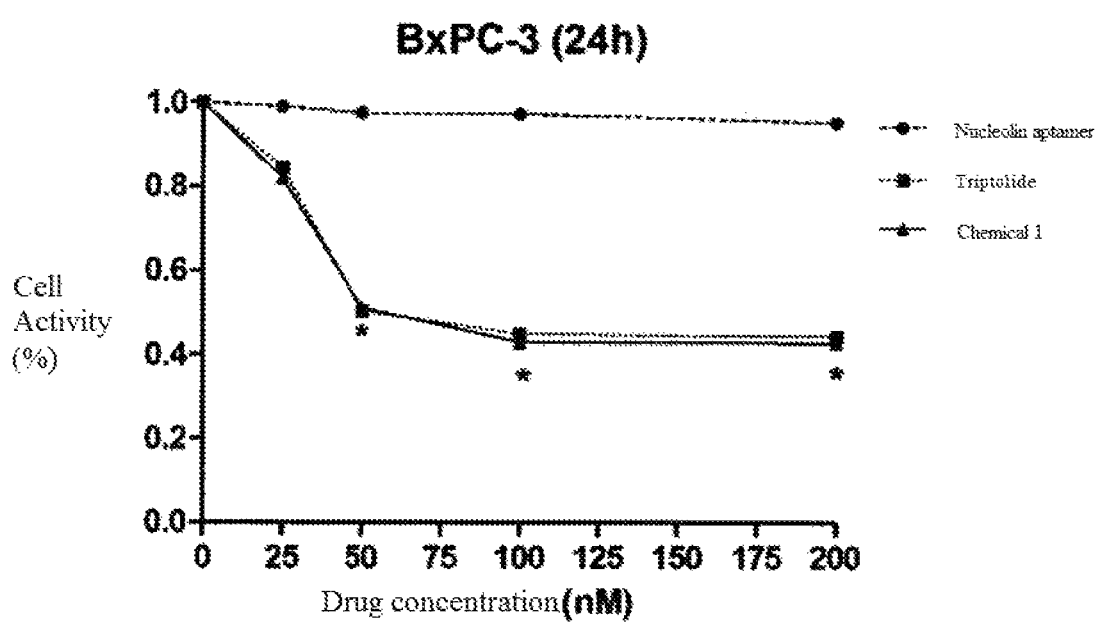
FIG. 18 shows the in vitro inhibitory effect of A-3 (i.e. compound (1)) on the growth of BxPC-3, in 24 hr, in Example 1.
Figure 19:
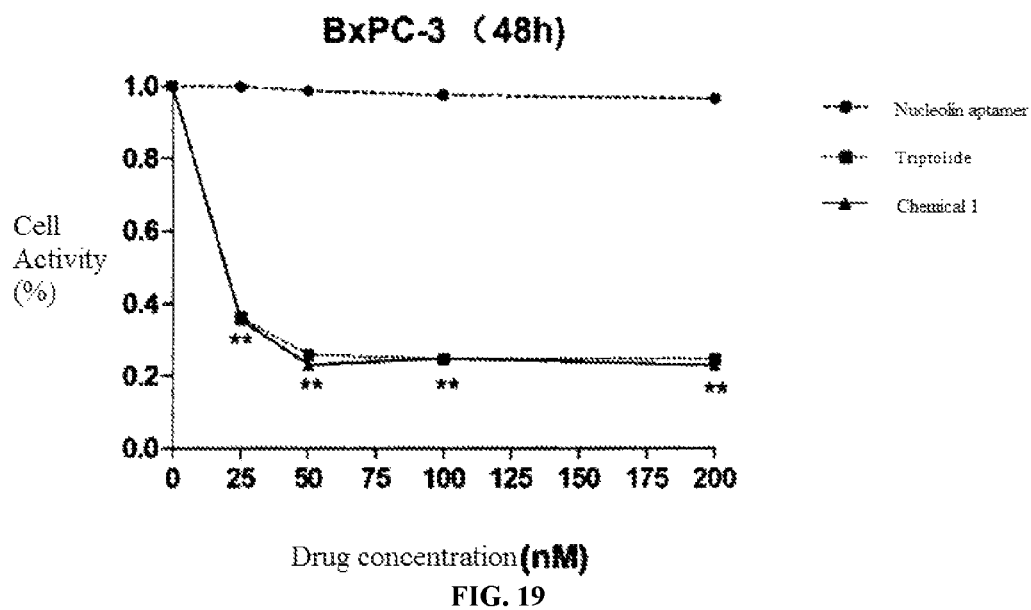
FIG. 19 shows the in vitro inhibitory effect of A-3 (i.e. compound (1)) on the growth of BxPC-3, in 48 hr, in Example 1.

3. Experimental Results:

As compared with blank references, TP and TP-AS1411 conjugate can significantly inhibit the proliferation of pancreatic cancer cells in a time and dose dependent manner in the concentration range of 50 nM-200 nM. Nucleolin aptamers do not have significant affect on pancreatic cancer cells. As compared to nucleolin aptamers, TP-nucleolin aptamer conjugate has significant effect on pancreatic cancer cells. Please refer to Table 1, FIGS. 18-19 and 29 for the details of the results.

TABLE 1

| Dose concentration (nM) | Nucleolin aptamers | | | | Triptolide | | | | Chemical 1 | | | |
|---|---|---|---|---|---|---|---|---|---|---|---|---|
| Absorbance (24 h) | | | | | | | | | | | | |
| 0 | 0.880 | 0.872 | 0.872 | 0.861 | 0.870 | 0.871 | 0.862 | 0.851 | 0.885 | 0.876 | 0.852 | 0.868 |
| 25 | 0.873 | 0.852 | 0.876 | 0.849 | 0.745 | 0.764 | 0.718 | 0.690 | 0.722 | 0.725 | 0.701 | 0.704 |
| 50 | 0.856 | 0.852 | 0.859 | 0.832 | 0.436 | 0.430 | 0.454 | 0.424 | 0.444 | 0.458 | 0.449 | 0.432 |
| 100 | 0.847 | 0.861 | 0.838 | 0.849 | 0.393 | 0.397 | 0.403 | 0.364 | 0.373 | 0.373 | 0.381 | 0.372 |
| 200 | 0.838 | 0.834 | 0.832 | 0.815 | 0.365 | 0.366 | 0.402 | 0.399 | 0.371 | 0.385 | 0.363 | 0.373 |
| Absorbance (48 h) | | | | | | | | | | | | |
| 0 | 0.881 | 0.873 | 0.882 | 0.863 | 0.872 | 0.871 | 0.864 | 0.853 | 0.882 | 0.869 | 0.854 | 0.860 |
| 25 | 0.874 | 0.870 | 0.886 | 0.860 | 0.296 | 0.322 | 0.317 | 0.322 | 0.326 | 0.312 | 0.322 | 0.281 |
| 50 | 0.865 | 0.862 | 0.869 | 0.851 | 0.219 | 0.223 | 0.231 | 0.220 | 0.195 | 0.196 | 0.211 | 0.196 |
| 100 | 0.857 | 0.853 | 0.860 | 0.834 | 0.211 | 0.206 | 0.223 | 0.212 | 0.204 | 0.205 | 0.220 | 0.231 |
| 200 | 0.848 | 0.844 | 0.842 | 0.834 | 0.200 | 0.218 | 0.222 | 0.213 | 0.193 | 0.208 | 0.193 | 0.197 |

EXAMPLE 2

Inhibition of Triptolide-SGC8C Conjugate on the Growth of Cancer Cells In Vitro

1. Experimental Materials:

Chemicals:

Triptolide (TP), source: commercially available;

SGC8C (also named as "leukemia aptamer"), source: commercially available;

Triptolide-SGC8C conjugate (also named as "chemical 2"), source: compound (22) prepared in Embodiment 12.

Cell lines: acute lymphoblastic leukemia T-cells (CCRF-CEM) and hepatocyte (L-02).

2. Experimental Methods:

The culture medium of acute lymphoblastic leukemia T-cells (CCRF-CEM) and hepatocyte (L-02) was RPMI-1640. Fetal bovine serum and two antibiotics were added into the above media so as to form a final culture medium with a final content of 10% and 1%. Cells were incubated in an incubator at 37° C. and with 5% $CO_2$. Growth conditions of the cells were constantly observed and cell counting was performed, and all the experiments were carried out on cells in logarithmic growth phase.

Preparation of drugs: triptolide was dissolved in DMSO for preparing a stock solution with 1 mg/ml and was stored in a refrigerator at −20° C.; sgc8c was dissolved in the serum free medium containing drug, and stored in the refrigerator at −20° C. after sgc8c fully dissolved; triptolide-sgc8c conjugate was fully dissolved in double-distilled water and it was used right after the preparation.

Study on anti-cancer activity: acute lymphoblastic leukemia T-cells (CCRF-CEM) and liver cells (L-02) were uniformly seeded into a 96-well plate in a low density ($1\times10^3 \sim 1\times10^4$, depending on the specific cell lines) and were placed in an incubator overnight for adhering, the used medium was replaced by a serum free medium containing drug. Triptolide was dissolved in DMSO for preparing a stock solution with 10 nM, the triptolide-sgc8c conjugate was dissolved in the serum free medium containing drug so as to form a solution with 10 mM, and it was used right after the preparation. The serum free medium containing drug was used as the blank reference, the concentration gradient of triptolide and triptolide-sgc8c conjugate used in the treatments: 0, 25, 50, 100 and 200 nM. The cells were then cultured in the incubator at 37° C. and with 5% $CO_2$. Cell activities were measured by MTT. The operations were repeated for 3 times.

Figure 20:
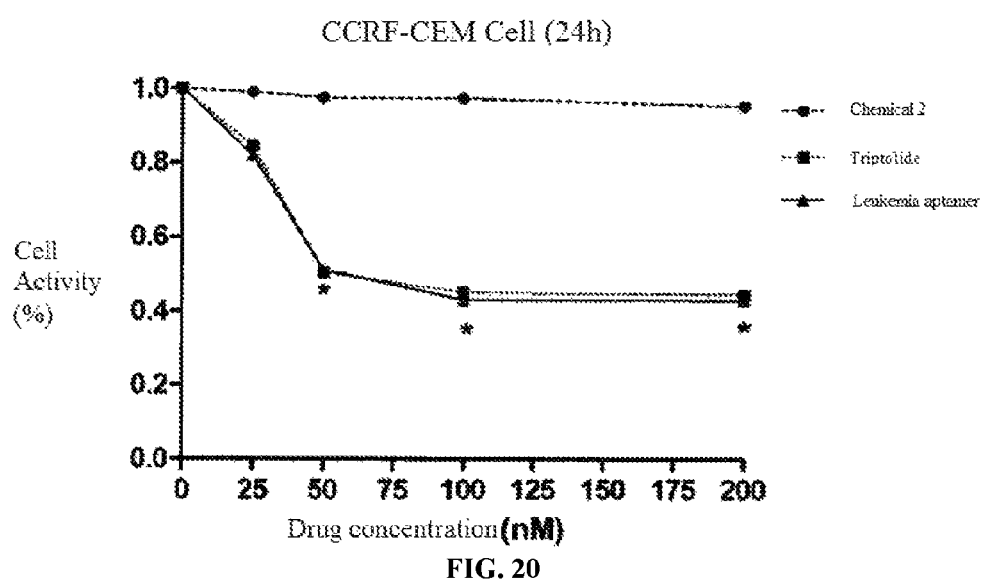
FIG. 20 shows the in vitro inhibitory effect of W-3 (i.e. compound (22)) on the growth of CCRF-CEM, in 24 hr, in Example 2.
Figure 21:
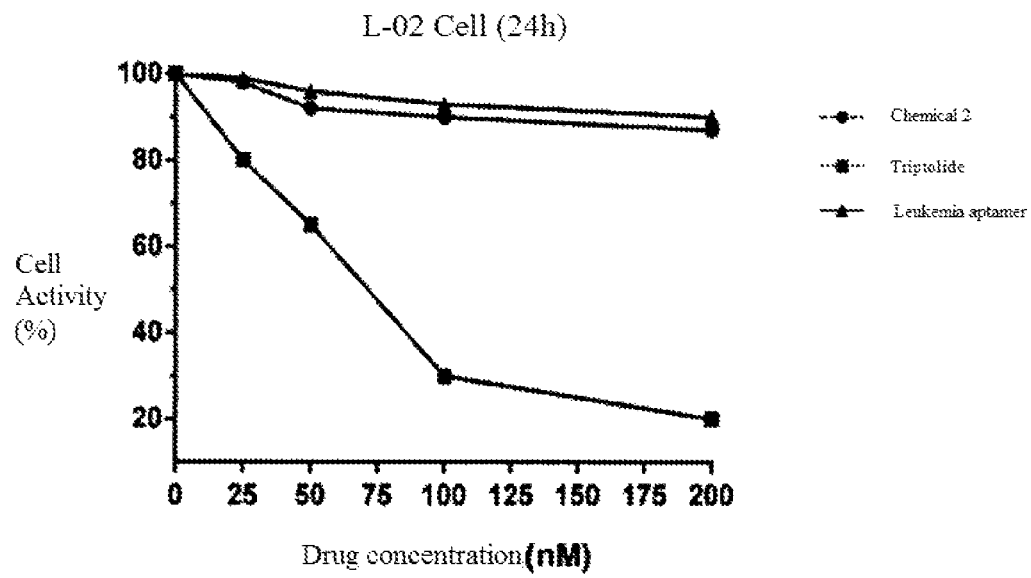
FIG. 21 shows the in vitro inhibitory effect of W-3 (i.e. compound (22)) on the growth of L-02 in Example 2.

3. Experimental Results:

As compared with the blank references, TP exhibits significant cytotoxicity to CCRF-CEM and L-02 cells in the concentration range of 50 nM to 200 nM in a dose dependent manner. TP-sgc8c conjugate showed significant cytotoxicity to CCRF-CEM cells but no significant effects to L-02 cells. As compared to blank references, sgc8c did not show significant cytotoxicity on both of the cells. Please refer to Table 2, FIGS. 20 and 21 for the details of the results.

EXAMPLE 3

Biodistribution of Triptolide-AS1411 Conjugate In Vivo

1. Experimental Materials:

Chemicals and reagents: triptolide (TP), source: commercially available;

AS1411 (also named as "nucleolin aptamer"), source: commercially available;

Triptolide-nucleolin aptamer conjugate, source: compound (3) prepared in Embodiment 3.

RPMI-1640 medium, fetal bovine serum, penicillin-streptomycin, matrigel, anhydrous ethanol, saline, ethyl acetate, acetonitrile and so forth.

Cell: human pancreatic cancer cell line BxPC-3.

Experimental animals: female nude mice.

Experimental Instrument: ultraclean benches, $CO_2$ incubator, inverted microscope, high speed centrifuges, ultra high speed centrifuge, vacuum drier and high performance liquid chromatography system.

2. Experimental Methods:

2.1 Establishment of Pancreatic Cancer Model 2.1.1 Culture of BxPC-3 cell lines: human pancreatic cancer cell line BxPC-3 was purchased from Chinese Academy of Science Shanghai Cell Bank. The cells were cultured in RPMI 1640 medium (purchased from sigma) containing 10% of fetal bovine serum (purchased from sigma) and 1.2 ml/1000 ml of penicillin-streptomycin (purchased from sigma) and were incubated in an incubator at 37° C. and with 5% $CO_2$. The inverted microscope was used for observation and cell counting, and all the experiments were carried out on cells in logarithmic growth phase.

2.1.2 Establishment of xenograft tumor-bearing mice with human pancreatic cancer cell line BxPC-3: female nude mice were provided and maintained in animal house in School of Chinese Medicine, Hong Kong Baptist University. BxPC-3 cells in logarithmic growth phase were used. 50:50 matrigel and serum free medium were resuspended to $2\times10^7$/ml. Female nude mice (20 g, 6-8 weeks) were inoculated with 100 μl cell suspension through subcutaneous injection at the right side of the back. The size of the tumors were measured by a bidirectional vernier caliper every day, and the formula for calculating the cancer size is: V=(length+width 2)/2, the length was the longest diameter of the cancer, and the width was the shortest diameter

TABLE 2

| Dose concentration (nM) | Leukemia aptamer | | | TP | | | Chemical 2 | | |
|---|---|---|---|---|---|---|---|---|---|
| Absorbance (CCRF-CEM) | | | | | | | | | |
| 0 | 0.80192 | 0.82148 | 0.88475 | 0.80192 | 0.82148 | 0.88475 | 0.89837 | 0.84378 | 0.86153 |
| 25 | 0.82546 | 0.82818 | 0.82498 | 0.75546 | 0.75818 | 0.75498 | 0.77313 | 0.79694 | 0.77319 |
| 50 | 0.81192 | 0.81148 | 0.81475 | 0.55019 | 0.54412 | 0.54474 | 0.54661 | 0.55778 | 0.57231 |
| 100 | 0.80476 | 0.80173 | 0.81221 | 0.26076 | 0.27173 | 0.28021 | 0.28186 | 0.29851 | 0.29817 |
| 200 | 0.80123 | 0.80604 | 0.80617 | 0.19023 | 0.18004 | 0.19017 | 0.18421 | 0.18219 | 0.19244 |
| Absorbance (L-02) | | | | | | | | | |
| 0 | 0.88955 | 0.89123 | 0.88297 | 0.90192 | 0.92148 | 0.98475 | 0.89715 | 0.87213 | 0.86511 |
| 25 | 0.88192 | 0.88148 | 0.88475 | 0.75546 | 0.75818 | 0.75498 | 0.86596 | 0.86697 | 0.88065 |
| 50 | 0.88019 | 0.88412 | 0.87474 | 0.59019 | 0.59412 | 0.59474 | 0.84059 | 0.87819 | 0.84312 |
| 100 | 0.88476 | 0.87173 | 0.86221 | 0.29076 | 0.27173 | 0.28021 | 0.85123 | 0.85604 | 0.84617 |
| 200 | 0.8754 | 0.87718 | 0.85498 | 0.23023 | 0.23004 | 0.23017 | 0.85751 | 0.84533 | 0.84191 | perpendicular to the length, and the following experiments were performed when the tumor reached the size of 200 mm³.

2.2 Grouping of tested animals and treatments 2.2.1 Preparation of the drugs: triptolide and triptolide-nucleolin aptamer conjugate. Triptolide was dissolved in a 50:50 ethanol/physiological saline solution for forming a drug solution with 0.6 mg/ml and was stored in a 4° C. refrigerator for further use; triptolide-nucleolin aptamer conjugate was measured and dissolved in a 50:50 ethanol/physiological saline solution for forming a drug solution with 22.0 mg/ml and was stored in 4° C. refrigerator for further use.

2.2.2 Grouping and treatments: when the tumor reached the size of 200 mm³, 30 tumor-bearing mice were randomly divided into A and B groups. In group A, 0.6 mg/kg of triptolide in ethanol/physiological saline solution was given through tail vein injection; in group B, 22.0 mg/kg of triptolide-nucleolin aptamer conjugate in ethanol/physiological saline solution was given through tail vein injection with the dosage 1 ml/kg. At 0.5, 2, 6, 12 and 24 hours, three mice in each groups were anesthetized by intraperitoneal injection with pentobarbital sodium, blood was collected through heart puncture, tissues such as heart, liver, spleen, lung, kidney and tumor tissue were removed and collected. The blood was centrifuged under 4° C. and 3000 rpm for 20 minutes, and serum was then obtained for further application; tissues such as heart, liver, spleen, lung, kidney and tumor tissues were stored at −80° C. for further application.

2.3 Detection of the Content of Triptolide/Triptolide-Nucleolin Aptamer Conjugate in Tissues by HPLC Tissues (heart, liver, spleen, lung, kidney and cancer tissue) with a certain weight were measured and a certain amount of pH 7.5 PBS solution was added to the tissues to perform homogenization. 0.2 ml of homogenized mixture was transferred to an eppendorf tube, 1.2 ml of ethyl acetate was vortex extracted for 3 minutes and centrifuged under 8000 rpm for 5 minutes. The upper layer of organic solution (1 ml) was transferred to another eppendorf tube for vacuum drying, and the residue was dissolved in 0.1 ml ethanol and was centrifuged under 4° C. and 20000 rpm for 10 minutes. The supernatant (10 μl) was injected to Agilent 1100 HPLC. The chromatography conditions were: separation column Symmetry Shield™ RP18 column (4.6 mm×250 mm, 5 um), the protective column ODS guid column (3.9 mm×20 mm, 5 um), the mobile phase: acetonitrile-water (23:77); the flow rate: 1.0 mL/min; the temperature of the column: 35° C.; the detection wavelength: 219 nm; the injection volume: 20.0 μL.

2.4 In Vivo Stability of Triptolide-Nucleolin Aptamer Conjugate

B samples in 2.2.2 were used. The concentration of free triptolide and triptolide-nucleolin aptamer conjugate in the tissues at different time interval was measured by the HPLC using the method set up in 2.3 and the release percentage was calculated. The formula: release percentage=(the concentration of triptolide)/(the concentration of triptolide+the concentration of triptolide-nucleolin aptamer), and the stability of the drug in the tissues were examined quantitatively.

2.5 Distribution of Triptolide-Nucleolin Aptamer Conjugate within Tissues

Samples A and B in 2.2.2 were used. The distribution of the drug in normal tissues and cancer tissues were measured and determined by the HPLC using the method set up in 2.3.

2.6 Statistic analysis

The data are represented by mean±standard deviation (SD), and the data were treated by Graphpad Prism 6.0 statistic software. Statistical significance was determined by t test and analysis of variance.

3. Experimental Results:

1. In vivo biodistribution of triptolide-nucleolin aptamer conjugate: the degree of dissociation of triptolide-nucleolin aptamer conjugate in different tissues at different time was measured by HPLC. The results are as follows. After 24 hours, only few triptolide-nucleolin aptamer conjugate was dissociated or not dissociated in normal tissues such as plasma, heart, liver, spleen, lung, kidney and so forth; triptolide-nucleolin aptamer conjugate was greatly dissociated in tumor tissue, and the degree of dissociation increases with time. The above results prove that the acid sensitive-vinylether bond used for connecting triptolide and nucleolin aptamer also exerts effect in vivo. The bond of the conjugate does not break in normal tissues, $C_{14}$ group is protected and the toxicity is reduced; the bond of the conjugate breaks in tumor tissue to release TP so as to achieve therapeutic effects, see Table 3 and FIG. 22.

TABLE 3

| | TP release percentage (%) in tissue with time | | | | |
|---|---|---|---|---|---|
| | 0.5 h | 2 h | 6 h | 12 h | 24 h |
| Plasma | 1.8 | 5.3 | 14.3 | 19.1 | 23.1 |
| | 2.0 | 5.9 | 15.0 | 20.3 | 23.8 |
| | 2.3 | 6.4 | 15.7 | 20.9 | 24.0 |
| Heart | 0.6 | 2.8 | 7.6 | 13.1 | 17.3 |
| | 1.0 | 3.2 | 7.9 | 14.0 | 18.2 |
| | 0.8 | 3.1 | 7.8 | 13.6 | 17.5 |
| Liver | 3.5 | 8.5 | 16.4 | 24.5 | 32.6 |
| | 3.4 | 8.2 | 15.0 | 23.1 | 30.1 |
| | 3.8 | 9.0 | 17.3 | 26.2 | 34.5 |
| Spleen | 1.3 | 4.5 | 10.3 | 14.9 | 16.2 |
| | 1.7 | 4.9 | 11.2 | 15.6 | 16.8 |
| | 2.1 | 5.2 | 12.4 | 16.1 | 17.3 |
| Lung | 1.4 | 3.8 | 7.9 | 11.2 | 14.2 |
| | 0.9 | 3.1 | 7.2 | 10.3 | 13.4 |
| | 1.1 | 2.6 | 6.8 | 10.1 | 13.1 |
| Kidney | 5.4 | 10.2 | 18.9 | 11.2 | 2.3 |
| | 5.1 | 9.6 | 17.8 | 10.3 | 1.9 |
| | 6.1 | 10.9 | 19.9 | 11.7 | 3.0 |
| Tumor | 23.6 | 39.1 | 49.2 | 60.6 | 78.6 |
| | 25.8 | 40.9 | 50.7 | 62.3 | 80.1 |
| | 26.3 | 41.0 | 52.1 | 64.1 | 81.2 |

Figure 22:
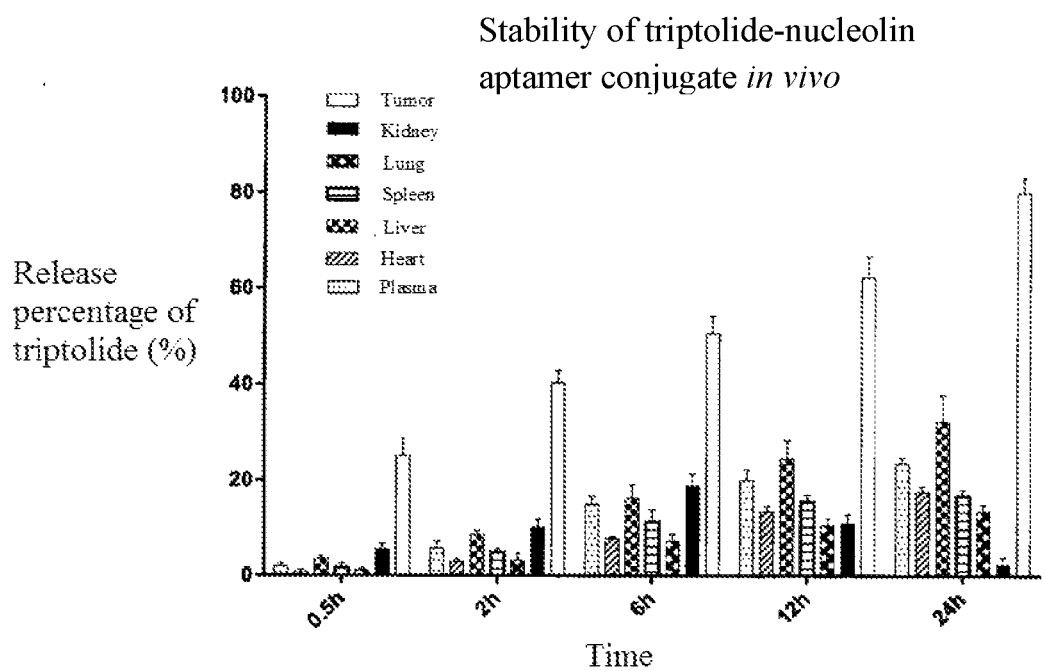
FIG. 22 is the study of the in vivo stability of A-3 (i.e. compound (1)) in Example 3.
Figure 23:
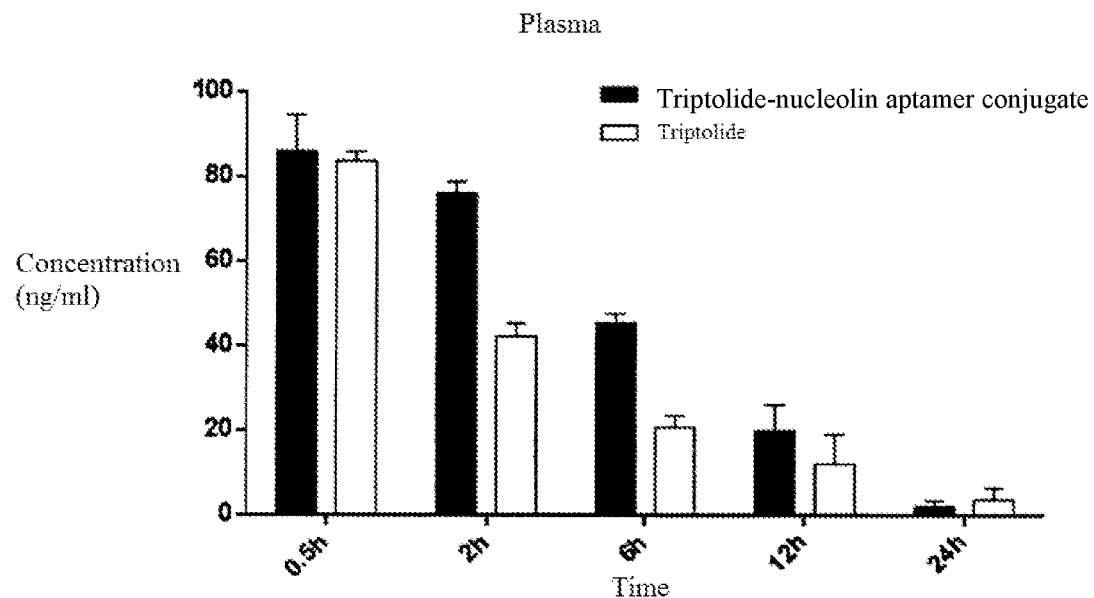
FIG. 23 is the study of the stability of A-3 (i.e. compound (1)) in plasma in Example 3.
Figure 24:
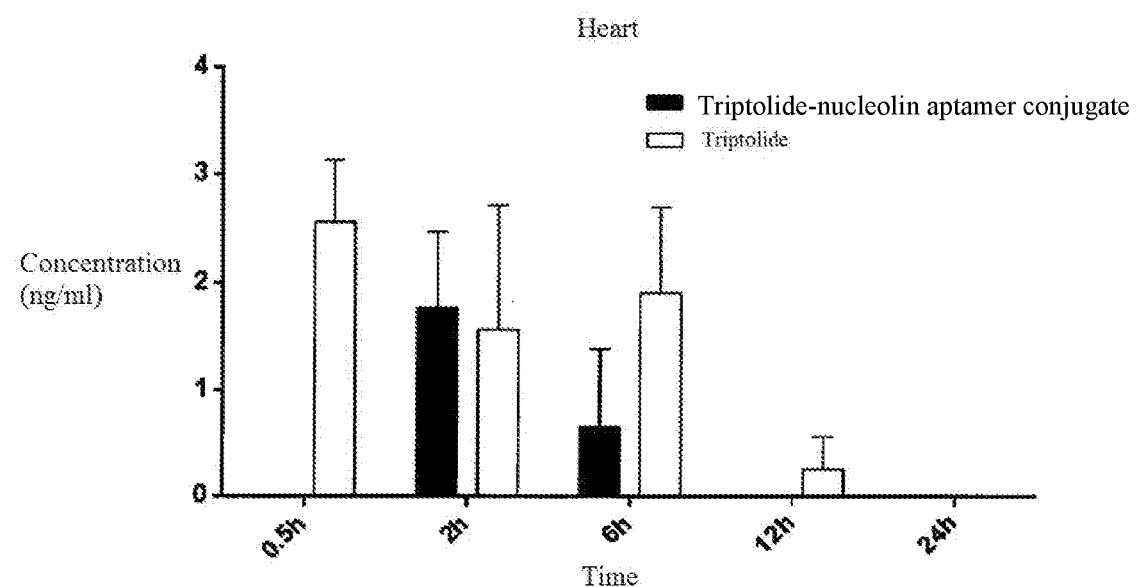
FIG. 24 is the study of the stability of A-3 (i.e. compound (1)) in heart in Example 3.
Figure 25:
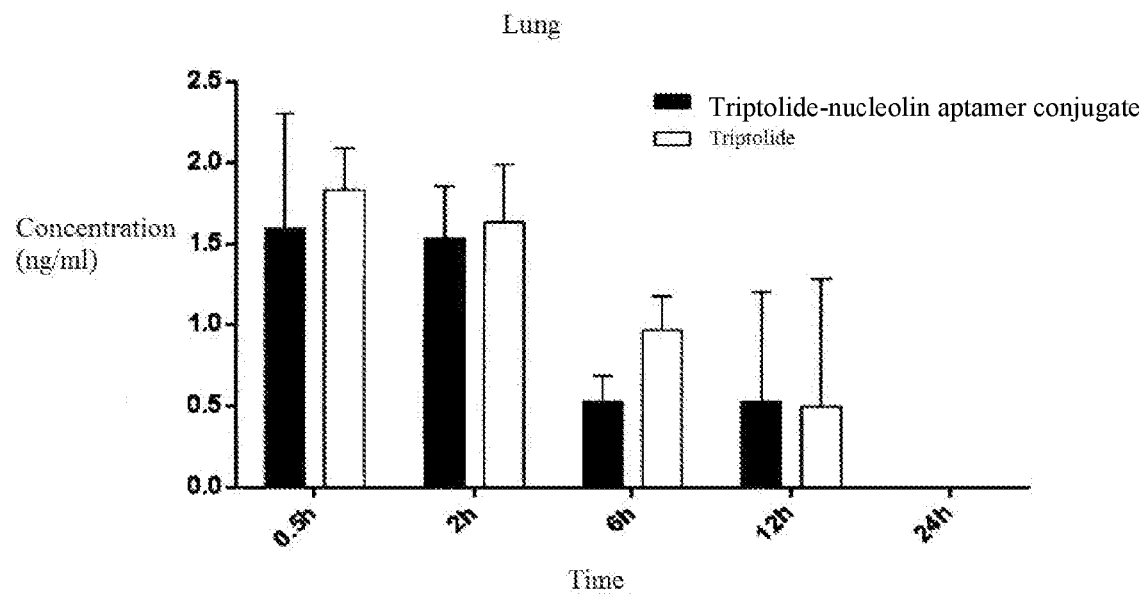
FIG. 25 is the study of the stability of A-3 (i.e. compound (1)) in lung in Example 3.
Figure 26:
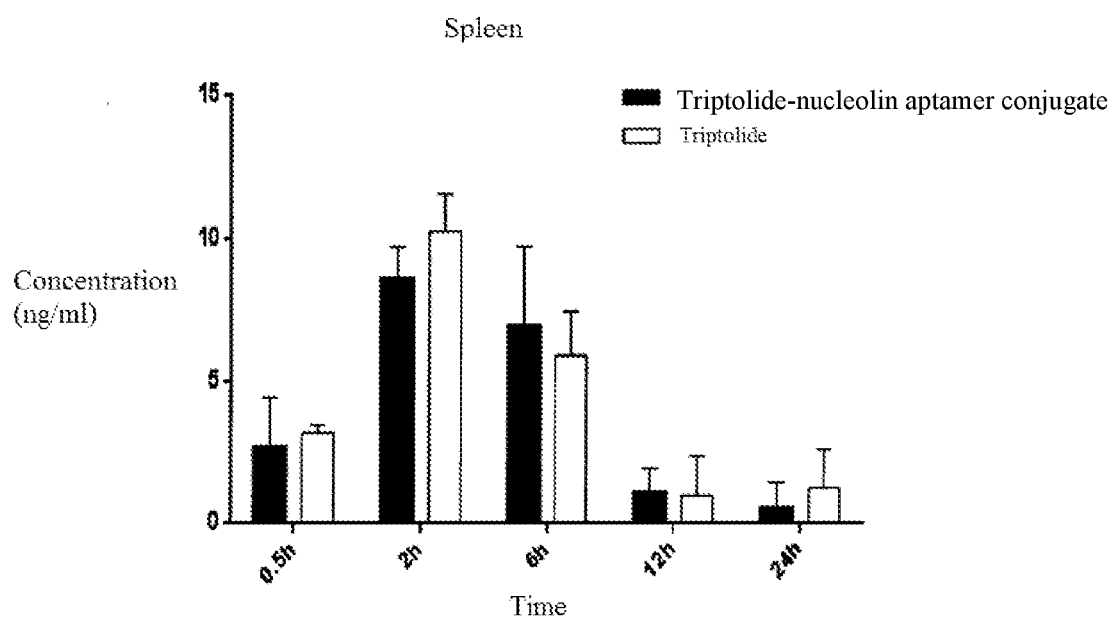
FIG. 26 is the study of the stability of A-3 (i.e. compound (1)) in spleen in Example 3.
Figure 27:
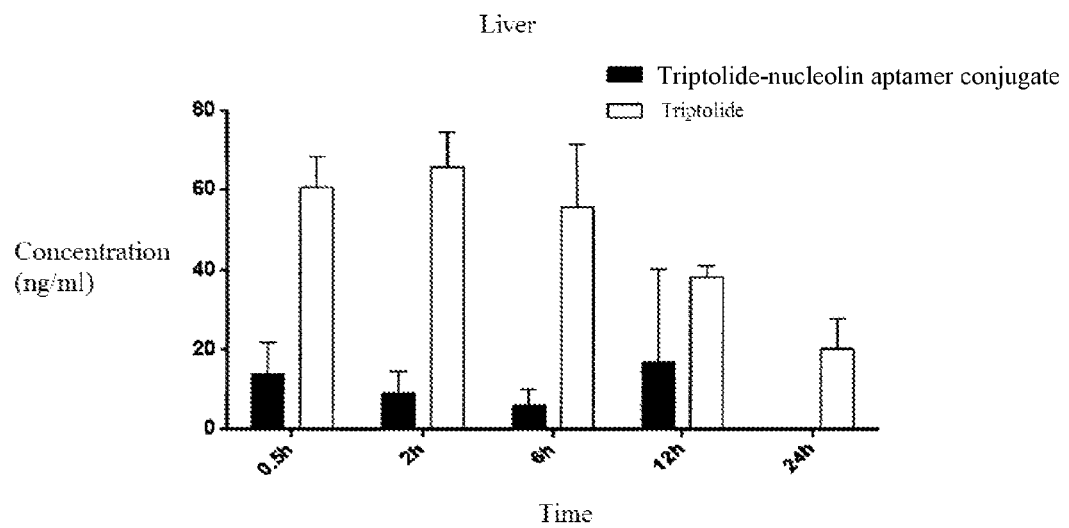
FIG. 27 is the study of the stability of A-3 (i.e. compound (1)) in liver in Example 3.
Figure 28:
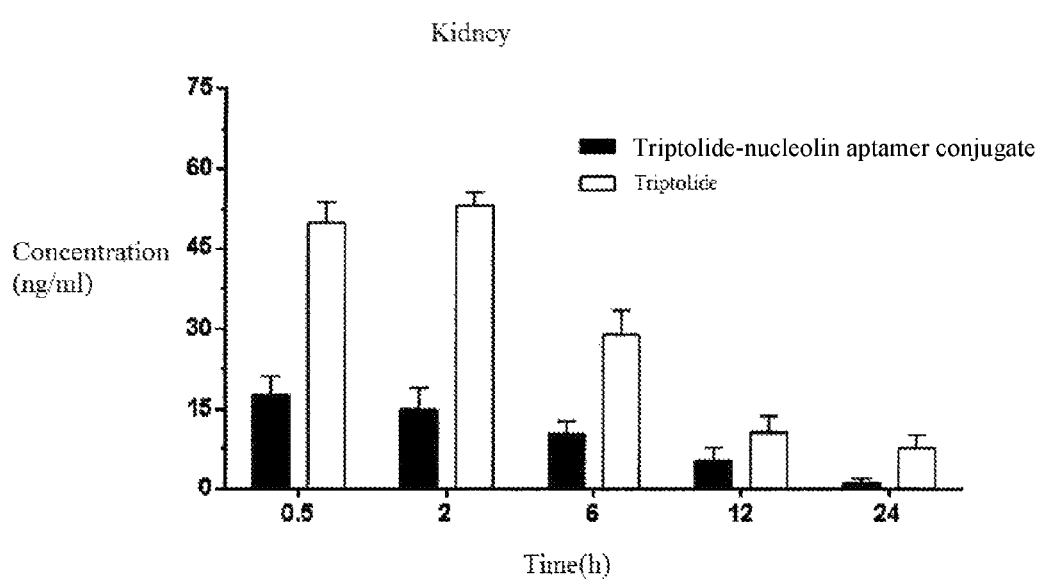
FIG. 28 is the study of the stability of A-3 (i.e. compound (1)) in kidney in Example 3.
Figure 29:
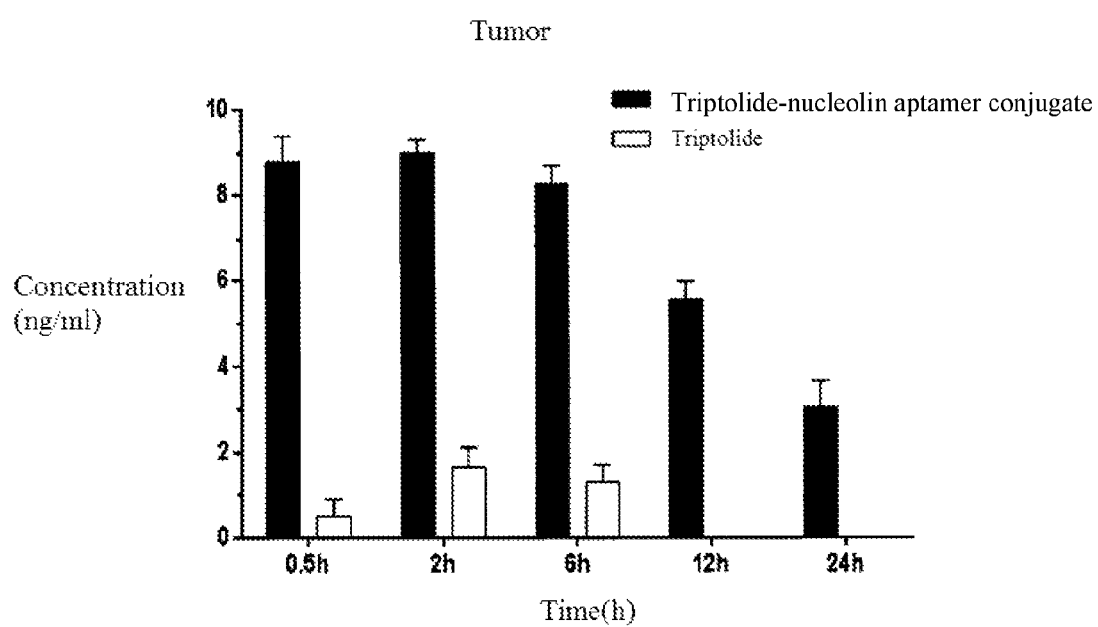
FIG. 29 is the study of the stability of A-3 (i.e. compound (1)) in cancer tissue in Example 3.

2. Selective biodistribution of triptolide-nucleolin aptamer conjugate in vivo: the biodistribution of the drug in normal organs and tumor tissues were measured by HPLC. The results are as shown in FIG. 22. 0.5 hour after administration, the drug concentrations in blood of experiment group A and the control group B rapidly increase to a maximum, however, the elimination rate of the drug in the experiment group A is slower than that of the control group B (FIG. 23). Comparing the experiment group A with the negative control group B, the distribution tendency of the drug in heart, spleen and lung are similar throughout the experimental period (all are converted to the concentration of triptolide). 0.5-2 hours after administration, triptolide was rapidly distributed to heart, spleen and lung issues, and it started to decrease 4 hours after administration (FIGS. 24-26). On the other hand, comparing the experiment group A with the negative control group B, the distribution tendency of the drug in liver, kidney and cancer are quite different throughout the experimental period (all are converted to the concentration of triptolide). In the experiment group A, the triptolide concentration in liver, kidney tissues was significantly lower than that in the control group B, and the triptolide concentration in tumor tissues was significantly higher than that in control group B (FIGS. 27-29). The above results indicate that the modifications of nucleolin aptamer can enhance the selectivity of triptolide to direct and accumulate at the cancer tissues so as to avoid accumulation in other tissues, especially in liver and kidney tissues. Please refer to Table 4 and FIGS. 23-29 for results of the experiment.

TABLE 4

| | Group A TP concentration (ng/ml) | | | Group B TP concentration (ng/ml) | | |
|---|---|---|---|---|---|---|
| Plasma | | | | | | |
| 0.5 h | 87.3 | 84.5 | 82.7 | 85.8 | 83.9 | 81.3 |
| 2 h | 76.7 | 78.4 | 73.2 | 38.8 | 43.9 | 44.3 |
| 6 h | 47.5 | 45.7 | 43.1 | 17.8 | 23.3 | 21.4 |
| 12 h | 20.1 | 13.9 | 26.2 | 10.7 | 19.8 | 6.3 |
| 24 h | 1.4 | 1.7 | 3.8 | 3.1 | 6.9 | 1.7 |
| Heart | | | | | | |
| 0.5 h | 0 | 0 | 0 | 3.2 | 2.1 | 2.4 |
| 2 h | 1.5 | 1.2 | 1.1 | 1.7 | 1.4 | 1.1 |
| 6 h | 0.5 | 0.3 | 0.2 | 1.9 | 2.7 | 1.1 |
| 12 h | 0 | 0 | 0 | 0.6 | 0.2 | 0 |
| 24 h | 0 | 0 | 0 | 0 | 0 | 0 |
| Lung | | | | | | |
| 0.5 h | 2.3 | 0.9 | 1.6 | 2.1 | 1.6 | 1.8 |
| 2 h | 1.9 | 1.3 | 1.4 | 2.0 | 1.6 | 1.3 |
| 6 h | 0.7 | 0.4 | 0.5 | 1.2 | 0.8 | 0.9 |
| 12 h | 1.3 | 0.1 | 0.2 | 1.4 | 0 | 0.1 |
| 24 h | 0 | 0 | 0 | 0 | 0 | 0 |
| Spleen | | | | | | |
| 0.5 h | 2.7 | 0.9 | 4.4 | 2.9 | 3.3 | 3.4 |
| 2 h | 8.7 | 7.3 | 9.6 | 11.7 | 9.7 | 9.3 |
| 6 h | 9.8 | 6.7 | 4.2 | 4.3 | 7.3 | 6.1 |
| 12 h | 0.5 | 2.1 | 0.7 | 0.1 | 0.3 | 2.6 |
| 24 h | 0 | 0 | 1.6 | 0.7 | 0.3 | 2.8 |
| Liver | | | | | | |
| 0.5 h | 22.6 | 12.3 | 6.9 | 69.3 | 58.2 | 54.4 |
| 2 h | 4.3 | 7.9 | 15.2 | 74.9 | 57.4 | 64.8 |
| 6 h | 10.2 | 5.7 | 2.4 | 68.3 | 37.9 | 60.7 |
| 12 h | 43.4 | 1.3 | 6.5 | 38.7 | 35.2 | 40.7 |
| 24 h | 0 | 0 | 0 | 28.9 | 15.3 | 16.4 |
| Kidney | | | | | | |
| 0.5 h | 18.7 | 13.9 | 24.3 | 52.7 | 65.3 | 44.8 |
| 2 h | 16.4 | 12.1 | 20.7 | 49.8 | 53.5 | 46.2 |
| 6 h | 9.3 | 16.4 | 4.2 | 34.5 | 28.8 | 32.3 |
| 12 h | 11.3 | 2.7 | 5.9 | 14.4 | 4.7 | 8.9 |
| 24 h | 7.5 | 8.4 | 7.1 | 0.9 | 6.7 | 1.3 |
| Tumor | | | | | | |
| 0.5 h | 9.6 | 10.5 | 8.3 | 0.5 | 0.7 | 0.33 |
| 2 h | 9.8 | 11.4 | 9.6 | 1.7 | 1.3 | 1.1 |
| 6 h | 8.3 | 9.5 | 8.7 | 1.5 | 1.2 | 1.4 |
| 12 h | 5.4 | 7.2 | 6.3 | 0 | 0 | 0 |
| 24 h | 3.3 | 2.4 | 3.9 | 0 | 0 | 0 |

In the novel anticancer compound, novel triptolide derivatives and the preparation thereof of the present invention, nucleic acid aptamers and triptolide are used as starting materials, special bonds are introduced through hydroxyl at $C_{14}$, epoxy and five-membered lactone ring of the triptolide so as to connect to the nucleic acid aptamer. The triptolide derivatives obtained by the modification have good performance in targeting, have strong anti-cancer activity, low toxicity and side effects, good water solubility and bioavailability. The techniques involved in the invention are scientific and rational, the quality is controllable; the preparation process is reproducible and suitable for production.

The invention claimed is:
1. A triptolide derivative, being a compound of the Formula (I):

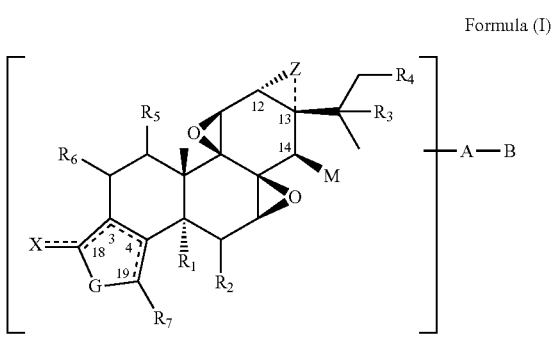

Formula (I)

$R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
A is —CO—, —CO—$(CH_2)_n$—CO—, —CH=CH—CO—, —CH=CH—$(CH_2)_n$—CO—, —CH(OH)-Ph-CO—, CH(OH)-Ph-$(CH_2)_n$—CO—, —$CH_2$-Ph-$(CH_2)_n$—CO—, —CO—NH—CO—, —CO—NH—$(CH_2)_n$—CO—, —$CH_2$—CH=CH—CO—, —$CH_2$—CH=CH—$(CH_2)_n$—CO—, —CO—$CH_2$—, —CO—O—$(CH_2)_n$—CO—, —$SO_2$-Ph-CO—, or —$SO_2$-Ph-$(CH_2)_n$—CO—; wherein 1≤n≤14; $(CH_2)_n$ further comprises a substituent selected from straight or branched alkyl, alkenyl, aralkyl, or alkyl aryalkyl, aryl, halogen, group with a heteroatom, heterocycle substituting one or more H in the $(CH_2)_n$, the alkyl is selected from methyl, ethyl, propyl, butyl, pentyl, hexyl or heptyl; the alkenyl is selected from vinyl, 1-propenyl, allyl, isopropenyl, 1-butenyl, 2-butenyl, 3-butenyl, 1,3-butadienyl, or the E, Z isomers thereof; the aralkyl and the alkyl aralkyl is selected from benzyl, diphenylmethyl, tolyl methyl, triphenylmethyl, cinnamyl, phenethyl, styryl, phenylbutyl and neophenyl; the aryl is selected from phenyl, diphenyl, tolyl, methylbenzyl, 4,2,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl and morpholino benzyl or phenyl; the halogen comprises fluorine, chlorine, bromine or iodine; the group with the heteroatom is selected from methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle is selected from pyridine, quinolone, thiophene, furan, oxazole, tetrazole, thiazole, imidazole, pyrazole, or indole;
B is an aptamer, and the aptamer is AS1411 or Sgc8c;
M is O or OH;
Z is O;
X is O;
wherein A is connected with M, Z or X.

2. The derivative according to claim 1, wherein A is
—CO—;
—CO—$CH_2$—CO—, —CO—$CH_2$—$CH_2$—CO—, —CO—$CH_2$—$CH_2$—$CH_2$—CO—, —CO—$CH_2$—$CH_2$—$CH_2$—$CH_2$—CO—;
—CH=CH—CO—;
—CH(OH)-Ph-CO—, —CH(OH)-Ph-$CH_2$—CO—, —CH(OH)-Ph-$CH_2$—$CH_2$—CO—, —CH(OH)-Ph-$CH_2$—$CH_2$—$CH_2$—CO—, —CH(OH)-Ph-$CH_2$—$CH_2$—$CH_2$—$CH_2$—CO—;
—$CH_2$-Ph-$CH_2$—CO—, —$CH_2$-Ph-$CH_2$—$CH_2$—CO—, —$CH_2$-Ph-$CH_2$—$CH_2$—$CH_2$—CO—, —$CH_2$-Ph-$CH_2$—$CH_2$—$CH_2$—$CH_2$—CO—;
—CO—NH—CO—, —CO—NH—$CH_2$—CO—, —CO—NH—$CH_2$—$CH_2$—CO—, —CO—NH—$CH_2$—$CH_2$—$CH_2$—CO—, —CO—NH—$CH_2$—$CH_2$—$CH_2$—$CH_2$—CO—;
—$CH_2$—CH=CH—CO—, —$CH_2$—CH=CH—$CH_2$—CO—, —$CH_2$—CH=CH—$CH_2$—$CH_2$—CO—, —$CH_2$—CH=CH—$CH_2$—$CH_2$—$CH_2$—CO—, —$CH_2$—CH=CH—$CH_2$—$CH_2$—$CH_2$—$CH_2$—CO;
—CO—$CH_2$—;
—CO—O—CO—, —CO—O—$CH_2$—CO—, —CO—O—$CH_2$—$CH_2$—CO—, —CO—O—$CH_2$—$CH_2$—$CH_2$—CO—, —CO—O—$CH_2$—$CH_2$—$CH_2$—$CH_2$—CO—;
—$SO_2$-Ph-CO—, —$SO_2$-Ph-$CH_2$—CO—, —$SO_2$-Ph-$CH_2$—$CH_2$—CO—, —$SO_2$-Ph-$CH_2$—$CH_2$—$CH_2$—CO—, or —$SO_2$-Ph-$CH_2$—$CH_2$—$CH_2$—$CH_2$—CO—.

3. The derivative according to claim 1, wherein the compound has the following structure:

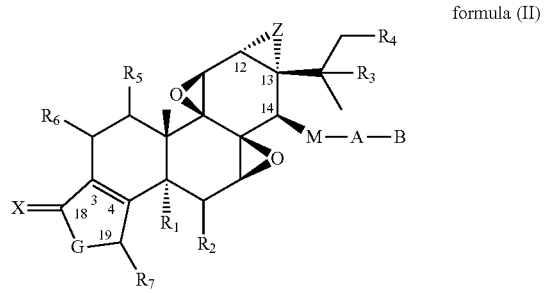

formula (II)

wherein, $R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
M is O;
Z is O;
X is O;
A is selected from —CO—, —CO—$(CH_2)_n$—CO—, —CH=CH—CO—, —CH=CH—$(CH_2)_n$—CO—, —CH(OH)—Ph-CO—, CH(OH)-Ph-$(CH_2)_n$—CO—, —$CH_2$-Ph-$(CH_2)_n$—CO—, —CO—NH—CO—, —CO—NH—$(CH_2)_n$—CO—, —$CH_2$—CH=CH—CO—, —$CH_2$—CH=CH—$(CH_2)_n$CO—, —CO—$CH_2$—, —CO—O—$(CH_2)_n$—CO—, —$SO_2$-Ph-CO— or —$SO_2$-Ph-$(CH_2)_n$—CO—; wherein $1 \leq n \leq 14$; $(CH_2)_n$ further comprises a substituent selected from straight or branched alkyl, alkenyl, aralkyl, alkyl aryalkyl, aryl, halogen, group with a heteroatom, heterocycle substituting one or more H in the $(CH_2)_n$, the alkyl is selected from methyl, ethyl, propyl, butyl, pentyl, hexyl or heptyl; the alkenyl is selected from vinyl, 1-propenyl, allyl, isopropenyl, 1-butenyl, 2-butenyl, 3-butenyl, 1,3-butadienyl, or the E, Z isomers thereof; the aralkyl and the alkyl aralkyl is selected from benzyl, diphenylmethyl, tolyl methyl, triphenylmethyl, cinnamyl, phenethyl, styryl, phenylbutyl or neophenyl; the aryl is selected from phenyl, diphenyl, tolyl, methylbenzyl, 4,2,6-trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl and morpholino benzyl or phenyl; the halogen comprises fluorine, chlorine, bromine and iodine; the group with the heteroatom is selected from methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle is selected from pyridine, quinolone, thiophene, furan, oxazole, tetrazole, thiazole, imidazole, pyrazole or indole;

B is an aptamer, and the aptamer is AS1411 or Sgc8c.

4. The derivative according to claim 3, wherein A is selected from —CO—;
—CO—$CH_2$—CO—, —CO—$CH_2$—$CH_2$—CO—, —CO—$CH_2$—$CH_2$—$CH_2$—CO—, —CO—$CH_2$—$CH_2$—$CH_2$—$CH_2$—CO—;
—CH=CH—CO—, —CH=CH—$CH_2$—CO—, —CH=CH—$CH_2$—$CH_2$—CO—, —CH=CH—$CH_2$—$CH_2$—$CH_2$—CO—, —CH=CH—$CH_2$—$CH_2$—$CH_2$—$CH_2$—CO—;
—CH(OH)-Ph-CO—, —CH(OH)-Ph-$CH_2$—CO—, —CH(OH)-Ph-$CH_2$—$CH_2$—CO—, —CH(OH)-Ph-$CH_2$—$CH_2$—$CH_2$—CO—, —CH(OH)-Ph-$CH_2$—$CH_2$—$CH_2$—$CH_2$—CO—;
—$CH_2$-Ph-$CH_2$—CO—, —$CH_2$-Ph-$CH_2$—$CH_2$—CO—, —$CH_2$-Ph-$CH_2$—$CH_2$—$CH_2$—CO—, —$CH_2$-Ph-$CH_2$—$CH_2$—$CH_2$—$CH_2$—CO—;
—CO—NH—CO—, —CO—NH—$CH_2$—CO—, —CO—NH—$CH_2$—$CH_2$—CO—, —CO—NH—$CH_2$—$CH_2$—$CH_2$—CO—, —CO—NH—$CH_2$—$CH_2$—$CH_2$—$CH_2$—CO—;
—$CH_2$—CH=CH—CO—, —$CH_2$—CH=CH—$CH_2$—CO—, —$CH_2$—CH=CH—$CH_2$—$CH_2$—CO—, —$CH_2$—CH=CH—$CH_2$—$CH_2$—$CH_2$—CO—, —$CH_2$—CH=CH—$CH_2$—$CH_2$—$CH_2$—$CH_2$—CO;
—CO—$CH_2$—;
—CO—O—CO—, —CO—O—$CH_2$—CO—, —CO—O—$CH_2$—$CH_2$—CO—, —CO—O—$CH_2$—$CH_2$—$CH_2$—CO—, —CO—O—$CH_2$—$CH_2$—$CH_2$—$CH_2$—CO—;
—$SO_2$-Ph-CO—, —$SO_2$-Ph-$CH_2$—CO—, —$SO_2$-Ph-$CH_2$—$CH_2$—CO—, —$SO_2$-Ph-$CH_2$—$CH_2$—$CH_2$—CO—, or —$SO_2$-Ph-$CH_2$—$CH_2$—$CH_2$—$CH_2$—CO—.

5. The triptolide derivative according to claim 3, wherein the compound is:

| | | | | | Substituent | | | | | | | | |
|---|---|---|---|---|---|---|---|---|---|---|---|---|---|
| No. | $R_1$ | $R_2$ | $R_3$ | $R_4$ | $R_5$ | $R_6$ | $R_7$ | G | M | Z | X | A | B |
| (1) | H | H | H | H | H | H | H | O | O | O | O | —CO—$CH_2$—$CH_2$—CO— | AS1411 |
| (2) | H | H | H | H | H | H | H | O | O | O | O | —CO— | AS1411 |
| (3) | H | H | H | H | H | H | H | O | O | O | O | —CH=CH—CO— | AS1411 |
| (4) | H | H | H | H | H | H | H | O | O | O | O | —CH($OCH_3$)—Ph—CO— | AS1411 |
| (5) | H | H | H | H | H | H | H | O | O | O | O | —$CH_2$—Ph—$CH_2$—CO— | AS1411 |
| (6) | H | H | H | H | H | H | H | O | O | O | O | —CO—NH—$CH_2$—CO— | AS1411 |
| (7) | H | H | H | H | H | H | H | O | O | O | O | —$CH_2$—CH=CH—CO— | AS1411 |
| (8) | H | H | H | H | H | H | H | O | O | O | O | —CO—$CH_2$— | AS1411 |
| (9) | H | H | H | H | H | H | H | O | O | O | O | —CO—O—$(CH_2)_2$—CO— | AS1411 |
| (10) | H | H | H | H | H | H | H | O | O | O | O | —CO—$CH_2$—CO— | AS1411 |
| (11) | H | H | H | H | H | H | H | O | O | O | O | —CH=CH—$CH_2$—CO— | AS1411 |

-continued

| No. | R₁ | R₂ | R₃ | R₄ | R₅ | R₆ | R₇ | G | M | Z | X | A | B |
|---|---|---|---|---|---|---|---|---|---|---|---|---|---|
| (12) | H | H | H | H | H | H | H | O | O | O | O | —CH₂—CH=CH—CH₂—CO— | AS1411 |
| (13) | H | H | H | H | H | H | H | O | O | O | O | —CO—O—CH₂—CO— | AS1411 |
| (14) | H | H | H | H | H | H | H | O | O | O | O | —SO₂—Ph—CH₂—CO— | AS1411 |
| (15) | H | H | H | H | H | H | H | O | O | O | O | —CH=CH—CH₂—CH₂—CO— | AS1411 |
| (16) | H | H | H | H | H | H | H | O | O | O | O | —CH₂—Ph—CH₂—CH₂—CO— | AS1411 |
| (17) | H | H | H | H | H | H | H | O | O | O | O | —CO—NH—CH2—CH₂—CO— | AS1411 |
| (18) | H | H | H | H | H | H | H | O | O | O | O | —CH₂—CH=CH—CH₂—CH₂—CO | AS1411 |
| (19) | H | H | H | H | H | H | H | O | O | O | O | —CO—O—CH₂—CH₂—CO | AS1411 |
| (20) | H | H | H | H | H | H | H | O | O | O | O | —CO—CH₂—CO— | Sgc8c |
| (21) | H | H | H | H | H | H | H | O | O | O | O | —CH=CH—CH₂—CO— | Sgc8c |
| (22) | H | H | H | H | H | H | H | O | O | O | O | —CH=CH—CO— | Sgc8c |
| (23) | H | H | H | H | H | H | H | O | O | O | O | —CH₂—Ph—CH₂—CO— | Sgc8c |
| (24) | H | H | H | H | H | H | H | O | O | O | O | —CO—NH—CH₂—CO— | Sgc8c |
| (25) | H | H | H | H | H | H | H | O | O | O | O | —CH₂—CH=CH—CH₂—CO— | Sgc8c |
| (26) | H | H | H | H | H | H | H | O | O | O | O | —CO—O—CH₂—CO— | Sgc8c |
| (27) | H | H | H | H | H | H | H | O | O | O | O | —SO₂—Ph—CH₂—CO— | Sgc8c |
| (28) | H | H | H | H | H | H | H | O | O | O | O | —CO—CH₂—CH₂—CO— | Sgc8c |
| (29) | H | H | H | H | H | H | H | O | O | O | O | —CH=CH—CH₂—CH₂—CO— | Sgc8c |
| (30) | H | H | H | H | H | H | H | O | O | O | O | CH₂—Ph—CH₂—CH₂—CO— | Sgc8c |
| (31) | H | H | H | H | H | H | H | O | O | O | O | —CO—NH—CH₂—CH₂—CO | Sgc8c |
| (32) | H | H | H | H | H | H | H | O | O | O | O | —CH₂—CH=CH—CH₂—CH₂—CO— | Sgc8c |
| (33) | H | H | H | H | H | H | H | O | O | O | O | —CO—O—CH₂—CH₂—CO— | Sgc8c |
| (34) | OH | H | H | H | H | H | H | O | O | O | O | —CH=CH—CO— | AS1411 |
| (35) | H | OH | H | H | H | H | H | O | O | O | O | —CH=CH—CO— | AS1411 |
| (36) | H | H | OH | H | H | H | H | O | O | O | O | —CH=CH—CO— | AS1411 |
| (37) | H | H | H | OH | H | H | H | O | O | O | O | —CH=CH—CO— | AS1411 |
| (38) | H | H | H | H | OH | H | H | O | O | O | O | —CH=CH—CO— | AS1411 |
| (39) | H | H | H | H | H | OH | H | O | O | O | O | —CH=CH—CO— | AS1411 |
| (40) | H | H | H | H | H | H | OH | O | O | O | O | —CH=CH—CO— | AS1411 |
| (41) | H | H | H | H | H | H | H | NH | O | O | O | —CH=CH—CO— | AS1411 |
| (42) | OH | H | H | H | H | H | H | O | O | O | O | —CH=CH—CO— | Sgc8c |
| (43) | H | OH | H | H | H | H | H | O | O | O | O | —CH=CH—CO— | Sgc8c |
| (44) | H | H | OH | H | H | H | H | O | O | O | O | —CH=CH—CO— | Sgc8c |
| (45) | H | H | H | OH | H | H | H | O | O | O | O | —CH=CH—CO— | Sgc8c |
| (46) | H | H | H | H | OH | H | H | O | O | O | O | —CH=CH—CO— | Sgc8c |
| (47) | H | H | H | H | H | OH | H | O | O | O | O | —CH=CH—CO— | Sgc8c |
| (48) | H | H | H | H | H | H | OH | O | O | O | O | —CH=CH—CO— | Sgc8c |
| (49) | H | H | H | H | H | H | H | NH | O | O | O | —CH=CH—CO— | Sgc8c. |

6. The derivative according to claim 1, wherein the compound has the following structure:

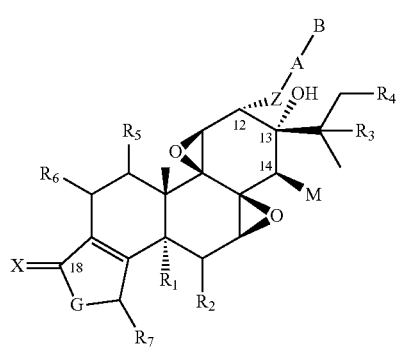

Formula (III)

wherein, R₁=H or OH;
R₂=H or OH;
R₃=H or OH;
R₄=H or OH;
R₅=H or OH;
R₆=H or OH;
R₇=H or OH;
G is O or NH;
M is OH;
Z is O;
X is O;

A is —SO₂-Ph-CO— or SO₂-Ph-(CH₂)ₙ—CO—; wherein 1≤n≤14; (CH₂)ₙ comprises a substituent selected from straight or branched alkyl, alkenyl, aralkyl, alkyl aryalkyl, aryl, halogen, a group with a heteroatom, heterocycle substituting one or more H in the (CH₂), the alkyl is selected from methyl, ethyl, propyl, butyl, pentyl, hexyl or heptyl; the alkenyl is selected from vinyl, 1-propenyl, allyl, isopropenyl, 1-butenyl, 2-butenyl, 3-butenyl, 1,3-butadienyl, or the E, Z isomers thereof; the aralkyl and the alkyl aralkyl is selected from benzyl, diphenylmethyl, tolyl methyl, triphenylmethyl, cinnamyl, phenethyl, styryl, phenylbutyl or neophenyl; the aryl is selected from phenyl, diphenyl, tolyl, methylbenzyl, 4,2,6- trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl, methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl and morpholino benzyl or phenyl; the halogen comprises fluorine, chlorine, bromine and iodine; the group with the heteroatom is selected from methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle is selected from pyridine, quinolone, thiophene, furan, oxazole, tetrazole, thiazole, imidazole, pyrazole or indole;

B is an aptamer, and the aptamer is AS1411 or Sgc8c.

7. The derivative according to claim 6, wherein A is selected from —$SO_2$-Ph-CO—, —$SO_2$-Ph-$CH_2$—CO—, —$SO_2$-Ph-$CH_2$—$CH_2$—CO—, —$SO_2$-Ph-$CH_2$—$CH_2$—$CH_2$—CO—, or —$SO_2$-Ph-$CH_2$—$CH_2$—$CH_2$—$CH_2$—CO—.

8. The triptolide derivative according to claim 6, wherein the compound is:

A is -CO—, —CO—$(CH_2)_n$—CO—, —CH=CH—CO—, —CH=CH—$(CH_2)_n$—CO—, —CH(OH)-Ph-CO—, —CH(OH)-Ph-$(CH_2)$—CO—, —$CH_2$-Ph-$(CH_2)$—CO—, —CO—NH—CO—, —CO—NH—$(CH_2)_n$—CO—, —$CH_2$—CH=CH—CO—, —$CH_2$—CH=CH—$(CH_2)_n$—CO—, —CO—$CH_2$—; —CO—O—$(CH_2)_n$—CO—, —$SO_2$-Ph-CO— or $SO_2$-Ph-$(CH_2)_n$—CO—; wherein $1 \le n \le 14$; $(CH_2)_n$ comprises a substituent selected from straight or branched alkyl, alkenyl, aralkyl, alkyl aryalkyl, aryl, halogen, a group with a heteroatom, heterocycle substituting one or more H in the $(CH_2)_n$, the alkyl is selected from methyl, ethyl, propyl, butyl, pentyl, hexyl or heptyl; the alkenyl is selected from vinyl, 1-propenyl, allyl, isopropenyl, 1-butenyl, 2-butenyl, 3-butenyl, 1,3-butadienyl, or the E, Z isomers thereof; the aralkyl and the alkyl aralkyl is selected from benzyl, diphenylmethyl, tolyl methyl, triphenylmethyl, cinnamyl, phenethyl, styryl, phenylbutyl or neophenyl; the aryl is selected from phenyl, diphenyl, tolyl, methylbenzyl, 4,2,6- trimethylphenyl, cumenyl, di(tert-butyl) phenyl, anthryl, indenyl, naphthyl, haloaryl, haloaryl alkylphenoxy, tolyloxy, xylyl alkoxy, 2,4,6-tris tolyloxy and cumene oxy, diphenyl, anilino, toluidino, tosyl, allyl benzyl or phenyl, furanyl, pyridyl, 2-pyridyl (pyridin-2-yl), indol-1-yl, chloromethylbenzyl or phenyl, trifluoromethylbenzyl or phenyl, hydroxybenzyl or phenyl,

| No. | $R_1$ | $R_2$ | $R_3$ | $R_4$ | $R_5$ | $R_6$ | $R_7$ | G | M | Z | X | A | B |
|---|---|---|---|---|---|---|---|---|---|---|---|---|---|
| (50) | H | H | H | H | H | H | H | O | OH | O | O | —$SO_2$—Ph—$CH_2$—CO— | AS1411 |
| (51) | H | H | H | H | H | H | H | O | OH | O | O | —$SO_2$—Ph—$CH_2$—$CH_2$—CO— | AS1411 |
| (52) | H | H | H | H | H | H | H | O | OH | O | O | —$SO_2$—Ph—$CH_2$—$CH_2$—$CH_2$—CO— | AS1411 |
| (53) | H | H | H | H | H | H | H | O | OH | O | O | —$SO_2$—Ph—$CH_2$—CO— | Sgc8c |
| (54) | H | H | H | H | H | H | H | O | OH | O | O | —$SO_2$—Ph—$CH_2$—$CH_2$—CO— | Sgc8c |
| (55) | H | H | H | H | H | H | H | O | OH | O | O | —$SO_2$—Ph—$CH_2$—$CH_2$—CO— | Sgc8c. |

9. The derivative according to claim 1, wherein the compound has the following structure:

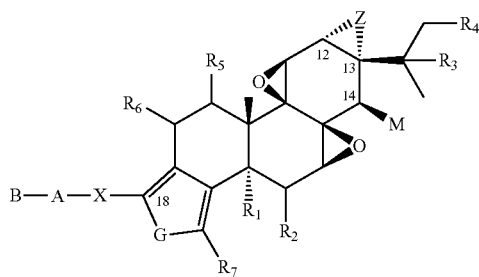

Formula (IV)

wherein, $R_1$=H or OH;
$R_2$=H or OH;
$R_3$=H or OH;
$R_4$=H or OH;
$R_5$=H or OH;
$R_6$=H or OH;
$R_7$=H or OH;
G is O or NH;
M is OH;
Z is O;
X is O;

methoxybenzyl or phenyl, ethoxybenzyl or phenyl, ethoxymethoxybenzyl or phenyl, allyloxybenzyl or phenyl, phenoxybenzyl or phenyl, acetoxybenzyl or phenyl, benzoyloxy benzyl or phenyl, methylthiobenzyl or phenyl, phenylthio benzyl or phenyl, tolylthio benzyl or phenyl, methylaminobenzyl or phenyl, dimethylaminobenzyl or phenyl, ethylaminobenzyl or phenyl, diethylaminobenzyl or phenyl, acetamidobenzyl or phenyl, carboxybenzyl or phenyl, methoxycarbonyl benzyl or phenyl, ethoxycarbonyl benzyl or phenyl, phenoxycarbonyl benzyl or phenyl, chlorophenoxycarbonyl benzyl or phenyl, N-cyclohexylcarbamoyloxy benzyl or phenyl, allyloxycarbonyl benzyl or phenyl, carbamoyl benzyl or phenyl, N-methylcarbamoyl benzyl or phenyl, N,N-dipropyl carbamoyl benzyl or phenyl, N-phenyl-carbamoyl-benzyl or phenyl, nitrobenzyl or phenyl, cyanobenzyl or phenyl, S-benzyl or phenyl, sulfate benzyl or phenyl, phosphonyl benzyl or phenyl, phosphate benzyl or phenyl and morpholino benzyl or phenyl; the halogen comprises fluorine, chlorine, bromine or iodine; the group with the heteroatom is selected from methoxy, ethoxy, propoxy, isopropoxy, n-butoxy, isobutoxy, tert-butoxy, methylthio, ethylthio, n-propylthio, iso-propylthio, n-butylthio, isobutylthio, tert-butylthio, methylsulfinyl, ethylsulfinyl, isopropyl sulfinyl, methylsulfonyl, ethylsulfonyl, isopropyl sulfonyl; the heterocycle is selected from pyridine, quinolone, thiophene, furan, oxazole, tetrazole, thiazole, imidazole, pyrazole or indole;

B is an aptamer, and the aptamer is AS1411 or Sgc8c.

10. The derivative according to claim 9, wherein A is selected from —CO—;
—CO—$CH_2$—CO—,  —CO—$CH_2$—$CH_2$—CO—,
—CO—$CH_2$—$CH_2$—$CH_2$—CO—,
—CO—$CH_2$—$CH_2$—$CH_2$—$CH_2$—CO—;
—CH═CH—CO—,  —CH═CH—$CH_2$—CO—,
—CH═CH—$CH_2$—$CH_2$—CO—,  —CH═CH—$CH_2$—$CH_2$—$CH_2$—CO—,  —CH═CH—$CH_2$—$CH_2$—$CH_2$—$CH_2$—CO—;
—CH(OH)-Ph-CO—, —CH(OH)-Ph-$CH_2$—CO—,
—CH(OH)-Ph-$CH_2$—$CH_2$—CO—,  —CH(OH)-Ph-$CH_2$—$CH_2$—$CH_2$—CO—,
—CH(OH)-Ph-$CH_2$—$CH_2$—$CH_2$—$CH_2$—CO—;
—$CH_2$-Ph-$CH_2$—CO—, —$CH_2$-Ph-$CH_2$—$CH_2$—CO—, —$CH_2$-Ph-$CH_2$—$CH_2$—$CH_2$—CO—, —$CH_2$-Ph-$CH_2$—$CH_2$—$CH_2$—$CH_2$—CO—;
—CO—NH—CO—,  —CO—NH—$CH_2$—CO—, —CO—NH—$CH_2$—$CH_2$—CO—,  —CO—NH—$CH_2$—$CH_2$—$CH_2$—CO—,  —CO—NH—$CH_2$—$CH_2$—$CH_2$—$CH_2$—CO—;
—$CH_2$—CH═CH—CO—, —$CH_2$—CH═CH—$CH_2$—CO—, —$CH_2$—CH═CH—$CH_2$—$CH_2$—CO—,  —$CH_2$—CH═CH—$CH_2$—$CH_2$—$CH_2$—CO—,
—$CH_2$—CH═CH—$CH_2$—$CH_2$—$CH_2$—$CH_2$—CO;
—CO—$CH_2$-;
—CO—O—CO—, —CO—O—$CH_2$—CO—, —CO—O—$CH_2$—$CH_2$—CO—,
—CO—O—$CH_2$—$CH_2$—$CH_2$—CO—, —CO—O—$CH_2$—$CH_2$—$CH_2$—$CH_2$—CO—;
—$SO_2$-Ph-CO—,  —$SO_2$-Ph-$CH_2$—CO—, —$SO_2$-Ph-$CH_2$—$CH_2$—CO—,
—$SO_2$-Ph-$CH_2$—$CH_2$—$CH_2$—CO—, or —$SO_2$-Ph-$CH_2$—$CH_2$—$CH_2$—$CH_2$—CO—.

11. The triptolide derivative according to claim 9, wherein the compound is:

12. A method for treating cancer comprising administering the triptolide derivative according to claim 1 to a subject in need thereof, wherein said cancer is selected from pancreatic cancer, renal cancer, small cell lung cancer, brain cancer, neural cancer, bone cancer, leukemia, lymphoma, intestinal cancer, uterine cancer, breast cancer, liver cancer, prostate cancer, skin cancer, and melanoma.

13. A method for preparing the triptolide derivative according to claim 1, comprising:
1) reacting triptolide or a modified compound thereof with a linking intermediate in an organic solvent at a temperature of from −20° C. to 100° C. and optionally in the presence of a catalyst;
2) reacting an aptamer in an alkaline solution with the product obtained from step 1) in an organic solvent at a temperature of from 0° C. to room temperature.

14. The method according to claim 13, characterized in that, where the aptamer is conjugated to $C_{18}$ or $C_{12}$, the method further comprises performing a protection reaction for the hydroxyl at $C_{14}$, wherein the protection agent is selected from tert-butyldimethylsilyl triflate or benzyl bromide.

15. The method according to claim 13, wherein the organic solvent in step 1) is selected from pyridine, dichloromethane, acetonitrile, N-methyl morpholine, dimethylsulfoxide, triethylamine or N, N-dimethyl pyridine, or combinations thereof.

16. The method according to claim 13, wherein the catalyst in step 1) is silver oxide.

17. The method according to claim 13, wherein the alkaline solution in step 2) is selected from a buffer of sodium carbonate/ sodium bicarbonate, triethylamine or potassium carbonate, or combinations thereof.

18. The method according to claim 13, characterized by, the organic solvent in step 2) is selected from dichloromethane, dimethylsulfoxide, acetonitrile or DMT-MM, or combinations thereof.

19. The method according to claim 13, wherein the linking intermediate in step 2) is selected from: succinic anhydride, phosgene, allyl bromide, propiolic acid, 4-bromomethyl benzoic acid, isocyanate, acyl chloride, chloroformate, benzenesulfonyl chloride or an analog thereof; and
wherein said analog is selected from malonic anhydride, glutaric anhydride, heptanoic anhydride, butynoic acid, pentynoic acid, heptynoic acid, ethyl 4-bromo (methoxy)methyl benzoate, ethyl 4-bromomethyl benzoate, methyl isocyanate, methyl 4-bromo-2-butene, 2-bromine acyl chloride, methyl 4- sulfonyl chlorobenzoate, methyl 4-bromo (methoxy) methylbenzoate,

| | | | | | | | | Substituent | | | | | |
|---|---|---|---|---|---|---|---|---|---|---|---|---|---|
| No. | $R_1$ | $R_2$ | $R_3$ | $R_4$ | $R_5$ | $R_6$ | $R_7$ | G | M | Z | X | A | B |
| (56) | H | H | H | H | H | H | H | O | OH | O | O | —CO—$CH_2$—CO— | AS1411 |
| (57) | H | H | H | H | H | H | H | O | OH | O | O | —CH═CH—$CH_2$—CO— | AS1411 |
| (58) | H | H | H | H | H | H | H | O | OH | O | O | —CH═CH—CO— | AS1411 |
| (59) | H | H | H | H | H | H | H | O | OH | O | O | —$CH_2$—Ph—$CH_2$—CO— | AS1411 |
| (60) | H | H | H | H | H | H | H | O | OH | O | O | —CO—NH—$CH_2$—CO— | AS1411 |
| (61) | H | H | H | H | H | H | H | O | OH | O | O | —$CH_2$—CH═CH—$CH_2$—CO— | AS1411 |
| (62) | H | H | H | H | H | H | H | O | OH | O | O | —CO—O—$CH_2$—CO— | AS1411 |
| (63) | H | H | H | H | H | H | H | O | OH | O | O | —$SO_2$—Ph—$CH_2$—CO— | AS1411 |
| (64) | H | H | H | H | H | H | H | O | OH | O | O | —CO—$CH_2$—$CH_2$—CO— | AS1411 |
| (70) | H | H | H | H | H | H | H | O | OH | O | O | —CO—$CH_2$—CO— | Sgc8c |
| (71) | H | H | H | H | H | H | H | O | OH | O | O | —CH═CH—$CH_2$—CO— | Sgc8c |
| (72) | H | H | H | H | H | H | H | O | OH | O | O | —CH═CH—CO— | Sgc8c |
| (73) | H | H | H | H | H | H | H | O | OH | O | O | —$CH_2$—Ph—$CH_2$—CO— | Sgc8c |
| (74) | H | H | H | H | H | H | H | O | OH | O | O | —CO—NH—$CH_2$—CO— | Sgc8c |
| (75) | H | H | H | H | H | H | H | O | OH | O | O | —$CH_2$—CH═CH—$CH_2$—CO— | Sgc8c |
| (76) | H | H | H | H | H | H | H | O | OH | O | O | —CO—O—$CH_2$—CO— | Sgc8c |
| (77) | H | H | H | H | H | H | H | O | OH | O | O | —$SO_2$—Ph—$CH_2$—CO— | Sgc8c |
| (78) | H | H | H | H | H | H | H | O | OH | O | O | —CO—$CH_2$—$CH_2$—CO— | Sgc8c. | methyl 4-bromo (methoxy) methylphenylacetate, methyl 4-bromo (methoxy) methylphenylpropionate, methyl 4-bromo (methoxy) methylphenylbutyrate, methyl 4-bromomethyl benzoate, methyl 4-bromomethyl phenylacetate, methyl 4-bromomethyl phenylpropionate, methyl 4-bromomethyl phenylbutyrate, methyl isocyanate, methyl isocyanatoformate, methyl isocyanatopropionate, methyl isocyanatobutyrate, methyl 4-bromo-2-butenoate, methyl 4-bromo-2-pentenoate, methyl 4-bromo-2-hexenoate, methyl 4-bromo-2-heptenoate, methyl 4-bromo-2-octenoate, 3-(chlorocarbonyl) propionate, benzyl 3-(chlorocarbonyl) acetate, benzyl 3-(chlorocarbonyl) butyrate, benzyl 3-(chlorocarbonyl) pentanoate, benzyl 3-(chlorocarbonyl) hexanoate, benzyl 3-(chlorocarbonyl) heptanoate, 2-bromoacetyl chloride, 2-bromoformyl chloride, 2-bromopropionyl chloride, 2-bromobutyryl chloride, 2-bromopentanoyl chloride, 2-bromohexanoyl chloride, 2-bromoheptanoyl chloride, methyl-4-(chlorosulfonyl)-phenylacetate, methyl-4-(chlorosulfonyl)-phenylpropionate, methyl-4-(chlorosulfonyl)-phenylbutyrate, methyl-4-(chlorosulfonyl)-pentanoate, methyl-4-(chlorosulfonyl)-hexanoate, methyl-4-(chlorosulfonyl)-heptanoate, methyl-4-(chlorosulfonyl)-octanoate, or the ethyl ester, propyl ester, butyl ester, methylphenyl ester, or ethylphenyl ester thereof.

\* \* \* \* \*

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: DNA aptamer

<400> SEQUENCE: 1
ggtggtggtg gttgtggtgg tggtgg                                    26

<210> SEQ ID NO 2
<211> LENGTH: 41
<212> TYPE: DNA
<213> ORGANISM: Artificial Sequence
<220> FEATURE:
<223> OTHER INFORMATION: DNA aptamer

<400> SEQUENCE: 2
atctaactgc tgcgccgccg ggaaaatact gtacggttag a                   41